United States Patent
Van Delft et al.

(10) Patent No.: US 10,745,488 B2
(45) Date of Patent: Aug. 18, 2020

(54) MODIFIED ANTIBODY, ANTIBODY-CONJUGATE AND PROCESS FOR THE PREPARATION THEREOF

(71) Applicant: SynAffix B.V., Oss (NL)

(72) Inventors: Floris Louis Van Delft, Nijmegen (NL); Remon Van Geel, Oss (NL); Maria Antonia Wijdeven, Lent (NL)

(73) Assignee: SYNAFFIX B.V., Oss (NL)

( * ) Notice: Subject to any disclaimer, the term of this patent is extended or adjusted under 35 U.S.C. 154(b) by 150 days.

(21) Appl. No.: 14/437,808

(22) PCT Filed: Oct. 23, 2013

(86) PCT No.: PCT/NL2013/050744
§ 371 (c)(1),
(2) Date: Apr. 22, 2015

(87) PCT Pub. No.: WO2014/065661
PCT Pub. Date: May 1, 2014

(65) Prior Publication Data
US 2015/0258210 A1   Sep. 17, 2015

Related U.S. Application Data

(60) Provisional application No. 61/717,187, filed on Oct. 23, 2012.

(30) Foreign Application Priority Data

Oct. 23, 2012 (EP) ..................... 12189604
Oct. 14, 2013 (EP) ..................... 13188607

(51) Int. Cl.
*A61K 47/68* (2017.01)
*A61K 47/54* (2017.01)
(Continued)

(52) U.S. Cl.
CPC .......... *C07K 16/3015* (2013.01); *A61K 47/61* (2017.08); *A61K 47/65* (2017.08);
(Continued)

(58) Field of Classification Search
None
See application file for complete search history.

(56) References Cited

U.S. PATENT DOCUMENTS 8,008,252 B2   8/2011   DeFrees et al.
8,697,061 B2   4/2014   Natunen et al.
(Continued)

FOREIGN PATENT DOCUMENTS

WO   WO 2004/063344 A2   7/2004
WO   WO 2005/051249 A1   6/2005
(Continued)

OTHER PUBLICATIONS

Alley et al., "Antibody-drug conjugates: targeted drug delivery for cancer," Current Opinion in Chemical Biology, vol. 14, 2010, pp. 529-537.

(Continued)

*Primary Examiner* — Karl J Puttlitz
*Assistant Examiner* — Kauser M Akhoon
(74) *Attorney, Agent, or Firm* — Foley & Lardner LLP

(57) ABSTRACT

The present invention relates to an antibody comprising a GlcNAc-S(A)$_x$ substituent, wherein S(A)$_x$ is a sugar derivative comprising x functional groups A wherein A is independently selected from the group consisting of an azido group, a keto group and an alkynyl group and x is 1, 2, 3 or 4, wherein said GlcNAc-S(A)$_x$ substituent is bonded to the antibody via CI of the N-acetylglucosamine of said GlcNAc-S(A)$_x$ substituent, and wherein said N-acetylglucosamine is optionally fucosylated. The invention also relates to an antibody-conjugate, in particular to an antibody-conjugate according to the Formula (20) or (20b), wherein AB is an antibody, S is a sugar or a sugar derivative, D is a molecule of interest, and wherein said N-acetylglucosamine is optionally fucosylated (b is 0 or 1). The invention further relates to a process for the preparation of a modified antibody, to a process for the preparation of an antibody-conjugate, and to said antibody-conjugate for use as a medicament. In addition, the invention relates to a kit of parts comprising an azide-modified antibody and a linker-conjugate, wherein said linker-conjugate comprises a (hetero)cycloalkynyl group and one or more molecules of interest.

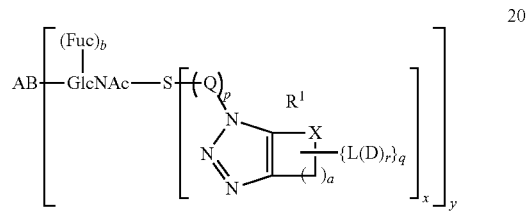

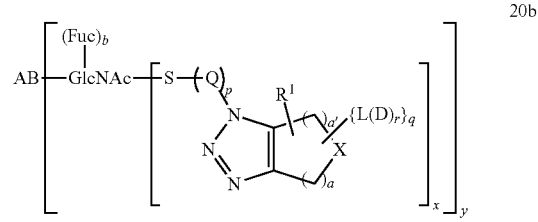

35 Claims, 27 Drawing Sheets
Specification includes a Sequence Listing.

(51) Int. Cl.
| | |
|---|---|
| C07K 16/30 | (2006.01) |
| C07K 16/32 | (2006.01) |
| C07K 16/22 | (2006.01) |
| C07K 16/28 | (2006.01) |
| C12P 21/02 | (2006.01) |
| A61K 47/61 | (2017.01) |
| A61K 47/65 | (2017.01) |
| A61K 39/00 | (2006.01) |

(52) U.S. Cl.
CPC .......... *A61K 47/68* (2017.08); *A61K 47/6803* (2017.08); *A61K 47/6809* (2017.08); *A61K 47/6845* (2017.08); *A61K 47/6849* (2017.08); *A61K 47/6855* (2017.08); *A61K 47/6869* (2017.08); *A61K 47/6889* (2017.08); *C07K 16/22* (2013.01); *C07K 16/2863* (2013.01); *C07K 16/2887* (2013.01); *C07K 16/32* (2013.01); *C12P 21/02* (2013.01); *A61K 2039/505* (2013.01); *C07K 2317/41* (2013.01); *C07K 2317/94* (2013.01)

(56) References Cited

U.S. PATENT DOCUMENTS

| | | | |
|---|---|---|---|
| 2005/0130235 | A1 | 6/2005 | Hsieh-Wilson et al. |
| 2005/0256030 | A1 | 11/2005 | Feng |
| 2007/0059275 | A1 | 3/2007 | DeFrees et al. |
| 2007/0190597 | A1 | 8/2007 | Agnew et al. |
| 2009/0068738 | A1 | 3/2009 | Bertozzi et al. |
| 2011/0207147 | A1 | 8/2011 | Jewett et al. |
| 2012/0076727 | A1 | 3/2012 | McBride et al. |

FOREIGN PATENT DOCUMENTS

| | | |
|---|---|---|
| WO | WO-2005/051429 A2 | 6/2005 |
| WO | WO-2005/056783 A1 | 6/2005 |
| WO | WO 2007/095506 A1 | 8/2007 |
| WO | WO-2007/133855 A1 | 11/2007 |
| WO | WO 2007/133855 A2 | 11/2007 |
| WO | WO 2008/029281 A2 | 3/2008 |
| WO | WO-2008/143944 A2 | 11/2008 |
| WO | WO-2009/025645 A1 | 2/2009 |
| WO | WO 2009/025645 A1 | 2/2009 |
| WO | WO 2009/067663 A1 | 5/2009 |
| WO | WO-2009/102820 A2 | 8/2009 |
| WO | WO 2009/102820 A2 | 8/2009 |
| WO | WO 2011/136645 A1 | 11/2011 |
| WO | WO-2011/136645 A1 | 11/2011 |
| WO | WO 2012/121973 A1 | 9/2012 |
| WO | WO 2012/134925 A1 | 10/2012 |
| WO | WO 2013/037824 A1 | 3/2013 |

OTHER PUBLICATIONS

Bross et al., "Approval Summary: Gemtuzumab ozogamicin in relapsed acute myeloid leukemia," Clinical Cancer Research, vol. 7, Jun. 2001, pp. 1490-1496.
Goodfellow et al., "An edoglycosidase with alternative glycan specificity allows broadened glycoprotein remodeling," Journal of the American Chemical Society, vol. 134, 2012, pp. 8030-8033.
Huang et al., "Chemoenzymatic glycoengineering of intact IgG antibodies for gain of functions," Journal of the American Chemical Society, vol. 134, 2012, pp. 12308-12318.
Labrijn et al., "Therapeutic IgG4 antibodies engage in Fab-arm exchange with endogenous human IgG4 in vivo," Nature Biotechnology, vol. 27, No. 8, Aug. 2009, pp. 767-773.
Ochiai et al., "Expeditious chemoenzymatic synthesis of homogeneous N-Glycoproteins carrying defined oligosaccharide ligands," Journal of the American Chemical Society, vol. 130, 2008, pp. 13790-13903.

Bertozzi et al., "Bioorthogonal Chemistry: Fishing for selectivity in a sea of functionality," Angew. Chem. Int. Ed., vol. 48, 2009, pp. 6974-6998.
van Delft et al., "Protein modification by strain-promoted alkyne-azide cycloaddition," ChemBioChem, vol. 12, 2011, pp. 1309-1312.
Boeggeman, E. et al., "Direct identification of nonreducing GlcNAc residues on N-glycans of glycoproteins using a novel chemoenzymatie method", Bioconjugate Chemistry, ACS, Washington, DC, US, vol. 18, No. 3, May 1, 2007, pp. 806-814.
Boeggeman, E. et al., "Site specific conjugation of fluoroprobes to the remodeled Fe N-Glycans of monoclonal antibodies using mutant glycosyltransferases: Application for cell surface antigen detection", Bioconjugate Chemistry, vol. 20, No. 6, Jun. 17, 2009, pp. 1228-1236.
Brockhausen, I. et al., "UDP-Gal: GlcNAc-R [beta]1,4-galactosyltransferase-a target enzyme for drug design, Acceptor specificity and inhibition of the enzyme", Glycoconjugate Journal, Kluwer Academic Publishers, BO, vol. 23, No. 7-8, Nov. 1, 2006, pp. 525-541.
European Search Report of EP 12189604.7 dated May 8, 2013.
International Search Report of PCT/NL2013/050744 dated Dec. 8, 2013.
Khidekel, N. et al., "A chemoenzymatic approach toward the rapid and sensitive detection of O-GLCNAC posttranslational modifications", Journal of the American Chemical Society, ACS Publications, US, vol. 125, No. 52, Dec. 31, 2003.
Pasek, M. et al., "The N-acetyl-binding pocket of N-acetylglucosaminyltransferases also accommodates a sugar analog with a chemical handle at C2", Glycobiology, vol. 22, No. 3, Mar. 1, 2012, pp. 379-388.
Qasba, P. K. et al., "Mutant glycosyltransferases assist in the development of a targeted drug delivery system and contrast agents for MRI", AAPS Journal, American Association of Pharmaceutical Scientists, US, vol. 8, No. 1, Jan. 1, 2006, pp. E190-E195.
Qasba, P. K. et al., "Site-specific linking of biomolecules via glycan residues using glycosyltransferases", Biotechnology Progress, vol. 24, No. 3, Apr. 22, 2008, pp. 520-526.
Ramakrishnan, B. et al., "Structure-based design of beta1, 4-galactosyltransferase 1(beta4Gal-T1) with equally efficient N-acetylgalactosaminyltransferase activity, Point mutation broadens beta4Gal-T1 donor specificity", Journal of Biological Chemistry, American Society for Biochemistry and Biology, US, vol. 277, No. 23, Jun. 7, 2002, pp. 20833-20839.
Van Wijk, X. M. R. et al., "A 4-deoxy analogue of N-acetyl-d-glucosamine inhibits heparin sulphate expression and growth factor binding in vitro", Experimental Cell Research, Academic Press, US, vol. 316, No. 15, Sep. 10, 2010, pp. 2504-2512.
Goff et al., (114) and Agnew et al. (115), Scientific Poster Abstracts: "Implementing label-free biomolecular interaction analyses in an antibody and protein core setting", and "Site-specific labeling of antibody N-glycans using a click chemistry-mediated chemoenzymatic approach", Journal of Biomolecular Techniques, vol. 23, supplemental, 2012.
Qasba, et al., "Site-Specific Linking of Biomolecules via Glycan Residues Using Glycosyltransferases", Biotechnology Progress, vol. 24(3), pp. 520-526, 2008.
Boeggeman et al., "Site Specific Conjugation of Fluoroprobes to the Remodeled Fc N-Glycans of Monoclonal Antibodies Using Mutant Glycosyltransferases: Application for Cell Surface Antigen Detection", Bioconjugate Chem., vol. 20(6), pp. 1228-1236, 2009.
Boeggeman et al., Direct Identification of Nonreducing GlcNac Residues on N-Glycans of Glycoproteins Using a Novel Chemoenzymatic Method, Bioconjugate Chem., vol. 18(3), pp. 806-814, 2007.
Qasba, et al., "Mutant Glycosyltransferases Assist in the Development of a Targeted Drug Delivery System and Contrast Agents for MRI", The AAPS Journal, vol. 8(1), pp. E190-E195, 2006.
Debets et al., "Aza-dibenzocyclooctynes for fast and efficient enzyme PEGylation via copper-free (3+2) cycloaddition", ChemComm, vol. 46, pp. 97-99, 2010.
Debets et al., "Bioconjugation with Strained Alkenes and Alkynes", Accounts of Chemical Research, vol. 44(9), pp. 805-815, 2011.

(56) References Cited

OTHER PUBLICATIONS

Lallana, et al., "Reliable and Efficient Procedures for the Conjugation of Biomolecules through Huisgen Azide-Alkyne Cycloadditions", Angew. Chem. Int. Ed. Engl., vol. 50, pp. 8794-8804, 2011.
Sharkey et al., "Use of antibodies and immunoconjugates for the therapy of more accessible cancers", Adv. Drug Deliv. Rev., vol. 60(12), pp. 1407-1420, 2008.
Dommerhold et al., "Strain-Promoted 1,3-Dipolar Cycloaddition of Cycloalkynes and Organic Azides", To Curr Chem (Z), 374:16, 2016.
"Cycloalkyne", Wikipedia; downloaded on Jan. 9, 2019.
Agard et al., "A Straom-Promoted [3+2] Azide-Alkyne Cycloaddition for Covalent Modification of Biomolecules in Living Systems", J.Am. Chem. Soc., vol. 126, pp. 15046-15047, 2004.
Ning et al., Visualizing Metabolically Labeled Glycoconjugates of Living Cells by Copper-Free and Fast Huisgen Cycloadditions, Angew. Chem. Int. Ed., vol. 47, pp. 2253-2255, 2008.
Huang et al., Chemoenzymatic Glycoengineering of Intact IgG Antibodies for Gain of Functions, J. Am. Chem. Soc., vol. 134, pp. 12308-12318, 2012.
Goodfellow et al., "An Endoglycosidase with Alternative Glycan Specificity Allows Broadened Glycoprotein Remodelling", J. Am. Chem. Soc., vol. 134, pp. 8080-8033, 2012.
Lugovskoy et al., "7$^{th}$ Annual European Antibody Congress 2011", mAbs 4:2, pp. 134-152, 2012.
Ramakrishnan et al., "Bioconjugation Using Mutant Glycosyltransferases for the Site-Specific Labeling of Biomolecules with Sugars Carrying Chemical Handles", Methods in Molecular Biology, vol. 751, pp. 281-296, 2011.
Van Geel et al., "Chemoenzymatic Conjugation of Toxic Payloads to the Globally Conserved N-Glycan of Native mAbs Provides Homogeneous and Highly Efficacious Antibody-Drug Conjugates", Bioconjug Chem., vol. 26(11), pp. 2233-2242, 2015.
Ramakrishnan et al., Structure-based Design of β1, 4-Galactosyltransferase I (β4Gal-T1) with Equally Efficient N-Acetylgalactosaminyltransferase Activity, J. Biol. Chem., 277:23, pp. 20833-20839, 2002.
Trimble et al., "Identification of Distinct Endoglycosidase (Endo) Activities in Flavobacterium meningosepticum: Endo $F_1$, Endo $F_2$, and Endo $F_3$", Biol. Chem., vol. 266(3), pp. 1646-1652, 1991.
Tarentino et al., "Enzymatic Deglycosylation of Asparagine-Linked Glycans: Purification, Properties, and Specificity of Oligosaccharide-Cleaving Enzymes from Flavobacterium meningosepticum", Methods in Enzymology, vol. 230, pp. 44-57, 1994.
Debets et al., "Azide: A Unique Dipole for Metal-Free Bioorthogonal Ligations", Chem Bio Chem, vol. 11, pp. 1168-1184, 2010.
Collin et al., "EndoS, a novel secreted protein from *Streptococcus pyogenes* with endoglycosidase activity on human IgG", The EMBO Journal, vol. 20, No. 12, pp. 3046-3055, 2001.
Collin et al., "Extracellular Enzymes with Immunomodulating Activities: Variations on a Theme in *Streptococcus pyogenes*", Infection and Immunity, pp. 2983-2992, 2003.
Allhorn et al., "Human IgG/FcyR Interactions Are Modulated by Streptococcal IgG Glycan Hydrolysis", PLoS One, vol. 3(1), e1413, 2008.
Baruah et al., "Selective Deactivation of Serum IgG: A General Strategy for the Enhancement of Monoclonal Antibody Receptor Interactions", vol. 420(1-2), pp. 1-7, 2012.
Juntula et al., "Engineered Thio-Trastuzumab-DM1 Conjugate with an Improved Therapeutic Index to Target Human Epidermal Growth Factor Receptor 2-Positive Breast Cancer", Clinical Cancer Research, vol. 16(19), pp. 4469-4768, 2010.
European Unpublished Patent Application No. 12189604.7, dated Oct. 23, 2012.
European Unpublished Patent Application No. 13188607.9, dated Oct. 14, 2013.
Aggeler et al., "Site-specific labeling of antibody N-glycans using a click chemistry-mediated chemoenzymatic approach", Poster, Annual Meeting of the Association of Biomolecular Resource Facilities (ABRF), Mar. 17-20, 2012.
Aggeler et al, "Site-specific Labeling of Antibody N-glycans using a Click Chemistry-mediated Chemoenzymatic Approach", Journal of Biomolecular Techniques, vol. 23 (Supplement), 528 2012.
Aggeler et al., "Site-specific click chemistry-mediated labeling of antibody glycans using metabolic and enzymatic approaches" Poster published at the Essential Protein Engineering Summit, 9-13.5. 2011, Boston, MA, USA.

mixture of mAb with
GlcNAc and GlcNAc(Fuc);
b = 0 or 1 mixture of mAb with
GlcNAc and GlcNAc(Fuc);
b = 0 or 1

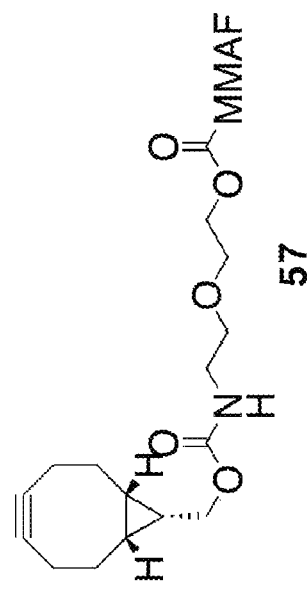
*Fig. 10b*
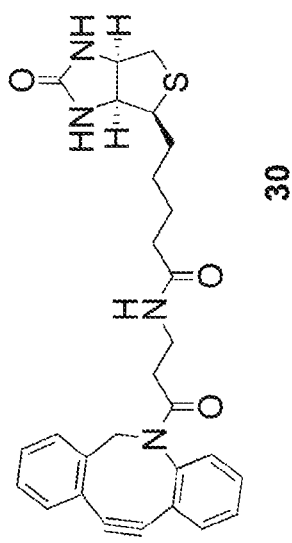
30
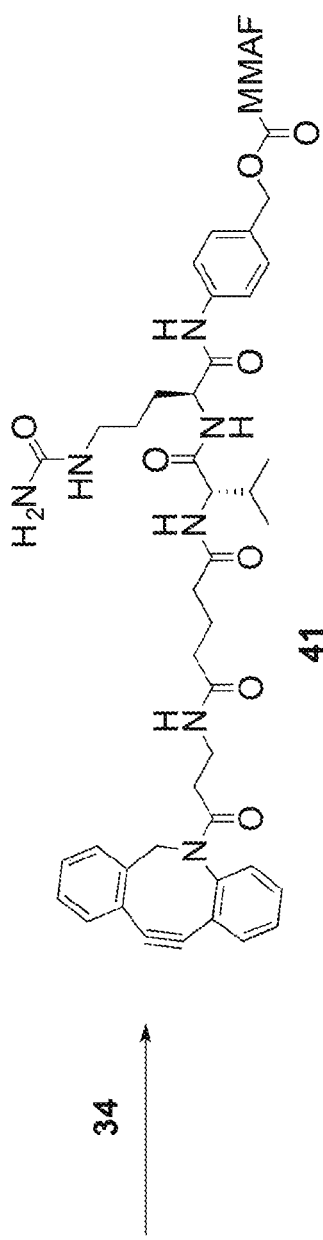
41
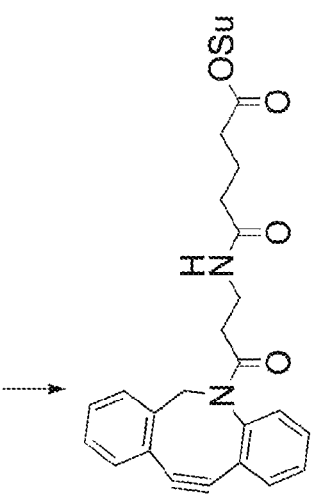
34
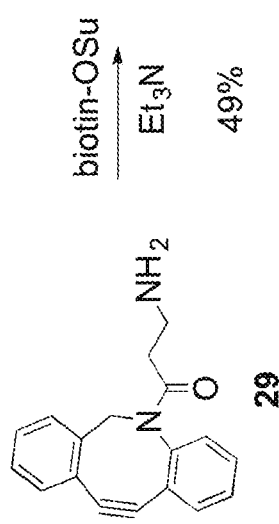
29
biotin-OSu
Et$_3$N
49%
*Fig. 11*

Fig. 13
A
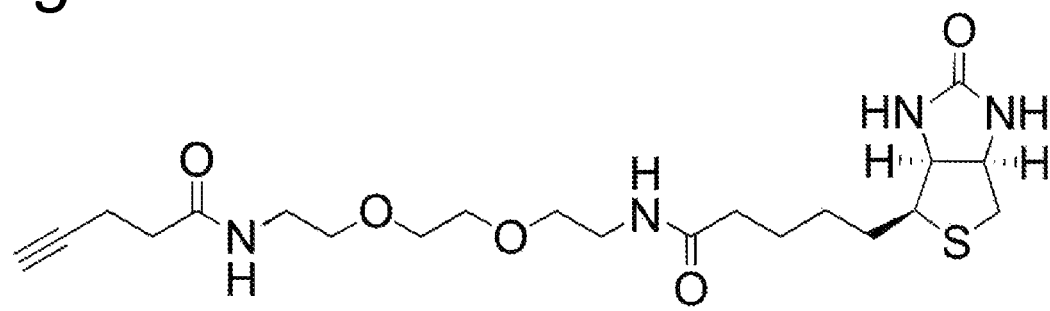
45
B
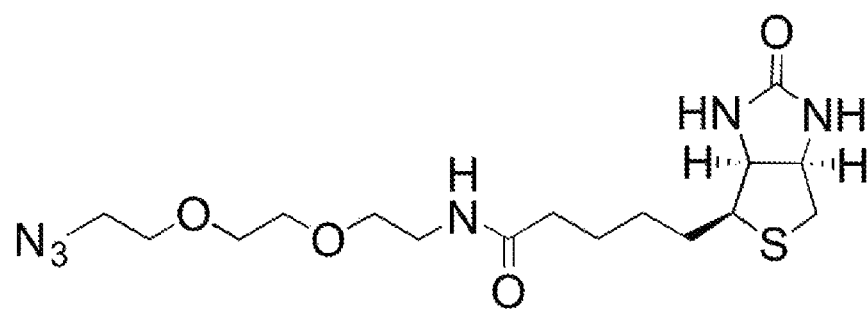
46
C
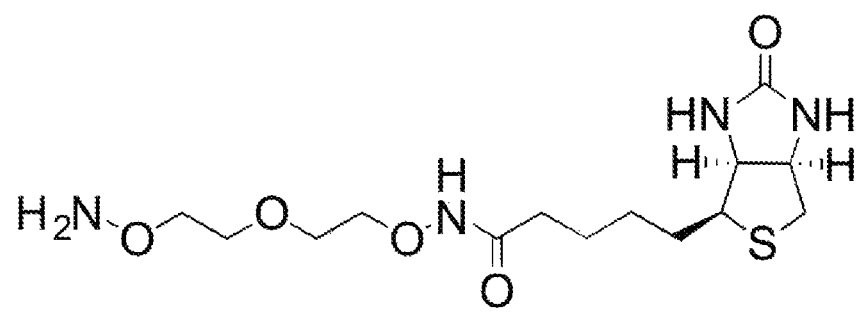
47

MODIFIED ANTIBODY, ANTIBODY-CONJUGATE AND PROCESS FOR THE PREPARATION THEREOF

TECHNICAL FIELD OF THE INVENTION

The present invention relates to modified antibodies, in particular to antibodies modified with one or more azide, alkyne and/or ketone functional groups. The modified antibodies according to the invention may be conjugated to a molecule of interest, to form an antibody-conjugate. Said molecule of interest may for example be an active substance. The invention therefore also relates to antibody-drug conjugates (ADCs). The invention further relates to a method for the preparation of the modified antibodies according to the invention, and to a method for the preparation of an antibody-conjugate according to the invention.

BACKGROUND OF THE INVENTION

Antibody-conjugates, i.e. antibodies conjugated to a molecule of interest via a linker, are known in the art. There is great interest in antibody-conjugates wherein the molecule of interest is a drug, for example a cytotoxic chemical. Antibody-drug-conjugates are known in the art, and consist of a recombinant antibody covalently bound to a cytotoxic chemical via a synthetic linker (S. C. Alley et al, *Curr. Opin. Chem. Biol.* 2010, 14, 529-537, incorporated by reference). The main objective of an antibody-drug-conjugate (ADC), also called immunotoxin, is to combine the high specificity of a monoclonal antibody for a tumor-associated antigen with the pharmacological potency of a "small" cytotoxic drug (typically 300 to 1,000 Da). Examples of ADCs include gemtuzumab ozogamicin (Mylotarg; anti-CD33 mAb conjugated to calicheamycin, Pfizer/Wyeth); brentuximab vedotin (SGN-35, Adcetris, a CD30-targeting ADC consisting of brentuximab, covalently linked to MMAE (monomethylauristatin), Seattle Genetics); trastuzumab-DM1 conjugate (T-DM1).

One advance in the field includes the emergence of extremely potent toxins, in particular taxanes, calicheamycins, maytansins, pyrrolobenzodiazepines, duocarmycins and auristatins. The low nanomolar to picomolar toxicity of these substances is a principal driver improvement over the earlier applied toxins. Another important technological advance involves the use of optimized linkers that are hydrolysable in the cytoplasm, resistant or susceptible to proteases, or resistant to multi-drug resistance efflux pumps that are associated with highly cytotoxic drugs.

ADCs known from the prior art are commonly prepared by conjugation of the linker-toxin to the side chain of antibody amino acid lysine or cysteine, by acylation or alkylation, respectively.

For lysines, conjugation takes place preferentially at lysine side chains with highest steric accessibility, the lowest pKa, or a combination thereof. Disadvantage of this method is that site-control of conjugation is low.

Better control of site-specificity is obtained by alkylation of cysteines, based on the fact that typically no free cysteines are present in an antibody, thereby offering the option of alkylating only those cysteines that are selectively liberated by a reductive step or specifically engineered into the antibody as free cysteines (as in so-called Thiomabs). Selective cysteine liberation by reduction is typically performed by treatment of whole antibody with a reducing agent (e.g. TCEP or DTT), leading to conversion of a disulfide bond into two free thiols (mostly in the antibody's hinge region). The liberated thiols are then alkylated with an electrophilic reagent, typically based on a maleimide attached to a linker-toxin, which generally proceeds fast and with high selectivity. With respect to engineering of an additional (free) cysteine into an antibody, enhanced site-control is attained with respect to the location of the added cysteine(s) and no reductive step is required, thereby ideally avoiding multiple disulfide bond cleavages and multiple alkylation. Also in this strategy alkylation of free cysteines is effected with maleimide chemistry, but full homogeneity is not attained.

At the same time, a disadvantage of ADCs obtained via alkylation with maleimides is that in general the resulting conjugates are unstable due to the reverse of alkylation, i.e. a retro-Michael reaction, thereby leading to release of linker-toxin from the antibody. Conjugation based on cysteine-maleimide alkylation is clearly not an ideal technology for developments of ADCs that preferably should not show premature release of toxin.

It is known in the art that azides ($N_3$ groups, also referred to as azido groups) can undergo selective cycloaddition with terminal alkynes (copper-catalyzed) or with cyclic alkynes (by virtue of ring strain). The triazoles resulting from reaction with alkynes are not susceptible to hydrolysis or other degradation pathways. It is also known in the art that ketones can undergo selective conjugation with hydroxylamines or hydrazines, resulting in respectively oximes or hydrazones. Oximes and hydrazones are also relatively inert at neutral conditions but may undergo hydrolysis at lower pH.

Several methods for the introduction of an azide into a protein have been reviewed recently by van Delft et al., *ChemBioChem.* 2011, 12, 1309 (incorporated by reference): (a) chemoselective diazo transfer reaction, (b) enzymatic conversion, (c) expression in auxotrophic bacteria and (d) genetic encoding. Chemoselective diazo transfer reactions (a) have limited applicability for antibodies since these typically take place on a protein's N-terminus, whereas in an antibody the N-termini of both heavy and light chain are in the binding region of the antibody. Expression in auxotrophic bacteria (c) and genetic encoding (d) are, albeit powerful, very complex strategies for non-specialized laboratories and furthermore cannot be used for straightforward post-modification of existing recombinant antibodies and are therefore not generally applicable.

With respect to enzymatic conversion of proteins (b), several enzymes have been reported over the years capable of achieving such transformation with unnatural, azide-containing substrates, e.g. transglutaminase, lipoic acid ligase, sortase, FGE and others (reviewed in Bertozzi et al., *Angew. Chem. Int. Ed.* 2009, 48, 6974, incorporated by reference). Without exception, however, these enzymes require specific recognition sequences in the protein, which need to be specifically engineered, and conjugation may be restricted to the protein's termini.

A potentially versatile strategy that may be generally applicable to all monoclonal antibodies involves the specific enzymatic conjugation to the Fc-attached glycan, which is naturally present in all antibodies expressed in mammalian (or yeast) cell cultures. Several strategies based on this concept are known in the art, such as via oxidation of the terminal galactose or via transfer of (unnatural) sialic acid to the same galactose moiety. However, for ADC purpose such a strategy is suboptimal because glycans are always formed as a complex mixture of isoforms, which may contain different levels of galactosylation (G0, G1, G2) and therefore would afford ADCs with poor control of drug-antibody ratio (DAR, see below).

FIG. 1 shows an antibody comprising a glycan on each heavy chain. These glycans are present in different isoforms with respect to galactosylation (G0, G1 and G2) and fucosylation (G0F, G1F and G2F).

In WO 2007/133855 (University of Maryland Biotechnology Institute), incorporated by reference herein, a chemoenzymatic method for the preparation of a homogeneous glycoprotein or glycopeptide is disclosed, involving a two-stage strategy entailing first trimming of the near-complete glycan tree (under the action of endo A or endo H) leaving only the core N-acetylglucosamine (GlcNAc) moiety (the so-called GlcNAc-protein), followed by a reglycosylation event wherein, in the presence of a catalyst comprising endoglycosidase (ENGase), an oligosaccharide moiety is transferred to the GlcNAc-protein to yield a homogeneous glycoprotein or glycopeptide. A strategy for azide-functionalized glycoproteins is disclosed, wherein a GlcNAc-protein is reacted in the presence of ENGase with a tetrasaccharide oxazoline containing two 6-azidomannose moieties, thereby introducing two azides simultaneously in the glycan. The azide-functionalized glycoprotein may then be catalytically reacted in a "click chemistry" cycloaddition reaction, in the presence of a catalyst (e.g. a Cu(I) catalyst) with a terminal alkyne bearing a functional moiety X of interest. No actual examples of said click chemistry are disclosed.

In *J. Am. Chem. Soc.* 2008, 130, 13790, incorporated by reference herein, Wang et al. disclose an efficient double attachment of a terminal alkyne-modified trisaccharide to bis-azidomodified ribonuclease B by copper-catalyzed click chemistry.

In *J. Am. Chem. Soc.* 2012, 134, 8030, incorporated by reference herein, Davis et al. disclose the transfer of oligosaccharide oxazolines on a core-fucosylated as well as nonfucosylated core-GlcNAc-Fc domain of intact antibodies, in the presence of glycosynthase EndoS.

In *J. Am. Chem. Soc.* 2012, 134, 12308, incorporated by reference herein, Wang et al. disclose the transfer of a tetrasaccharide oxazoline containing two 6-azidomannose moieties on core-fucosylated as well as nonfucosylated core-GlcNAc-Fc domain of intact antibodies (Rituximab) in the presence of glycosynthase mutants EndoS-D233A and EndoS-D233Q. This process is shown schematically in FIG. 2, and results in an antibody comprising four azido groups. The subsequent conjugation of the azido-modified IgG with click chemistry is mentioned but not disclosed.

However, a disadvantage of the glycosynthase strategies disclosed in WO 2007/133855, *J. Am. Chem. Soc.* 2012, 134, 8030 and *J. Am. Chem. Soc.* 2012, 134, 12308 is the lengthy and complex synthesis of the required azido-containing oligosaccharide oxazolines. In addition, the azido-containing oligosaccharide oxazolines comprise two azido groups. To date, it has not been shown whether this process may be suitable for the introduction of only one azido group on an antibody glycan.

Qasba et al. disclose in *J. Biol. Chem.* 2002, 277, 20833, incorporated by reference herein, that mutant galactosyltransferases GalT(Y289L), GalT(Y289I) and GalT(Y289N) can enzymatically attach GalNAc to a non-reducing GlcNAc sugar (β-benzyl-GlcNAc).

WO 2004/063344 (National Institutes of Health), incorporated by reference herein, discloses mutant galactosyltransferases GalT(Y289L), GalT(Y289I) and GalT(Y289N). A process is disclosed wherein complex glycans such as those on monoclonal antibodies (Rituxan, Remicade, Herceptin) are first converted into G0 glycans on antibodies by treatment with galactosidase, in order to remove all chain-terminal galactose. These G0 antibodies are subsequently subjected to GalNAc-UDP in the presence of GalT(Y289L), leading to antibodies with significantly more homogeneous glycan structures.

Qasba et al. disclose in *Bioconjugate Chem.* 2009, 20, 1228, incorporated by reference herein, that the process disclosed in WO 2004/063344 also proceeds for non-natural GalNAc-UDP variants substituted on the N-acetyl group. β-Galactosidase treated monoclonal antibodies having a G0 glycoform are fully galactosylated to the G2 glycoform after transfer of a galactose moiety comprising a C2-substituted azidoacetamido moiety (GalNAz) to the terminal GlcNAc residues of the glycan, leading to tetraazido-substituted antibodies, i.e. two GalNAz moieties per heavy chain. This process is shown schematically in FIG. 3. The conjugation of said tetraazido-substituted antibodies to a molecule of interest was not disclosed. The transfer of a galactose moiety comprising a C2-substituted keto group (C2-keto-Gal) to the terminal GlcNAc residues of a G0 glycoform glycan, as well as the linking of C2-keto-Gal to aminooxy biotin, is also disclosed. In all cases, GalT(Y289L) mutant is used for the transfer of GalNAc-UDP (or GalNAz-UDP) to the antibodies, but the use of mutants GalT(Y289N) or GalT(Y289I) is not disclosed.

A disadvantage of the method disclosed in WO 2004/063344 and *Bioconjugate Chem.* 2009, 20, 1228 is that conjugation of the tetraazido-substituted antibodies to a molecule of interest would lead to an antibody-conjugate with typically two molecules of interest per glycan (provided that said conjugation would proceed with complete conversion). In some cases, for example when the molecule of interest is a lipophilic toxin, the presence of too many molecules of interest per antibody is undesired since this may lead to aggregate formation (*BioProcess International* 2006, 4, 42-43, incorporated by reference).

WO 2007/095506 and WO 2008/029281 (Invitrogen Corporation), incorporated by reference herein, disclose a method of forming a glycoprotein conjugate wherein the glycoprotein is contacted with UDP-GalNAz in the presence of GalT(Y289L) mutant, leading to the incorporation of GalNAz at a terminal non-reducing GlcNAc of an antibody carbohydrate. Subsequent copper-catalyzed click chemistry with a terminal alkyne or Staudinger ligation can then be used to conjugate a reporter molecule, solid support or carrier molecule to the attached azide moiety. WO 2007/095506 and WO 2008/029281 further disclose that if no terminal GlcNAc sugars are present on the antibody, Endo H, Endo A or Endo M enzyme may be used to generate a truncated chain which terminates with one N-acetylglucosamine residue.

Antibody-conjugates known in the art generally suffer from several disadvantages. For antibody drug-conjugates, a measure for the loading of the antibody with a toxin is given by the drug-antibody ratio (DAR), which gives the average number of active substance molecules per antibody. However, the DAR does not give any indication regarding the homogeneity of such ADC.

Processes for the preparation of an antibody-conjugate known from the prior art generally result in a product with a DAR between 1.5 and 4, but in fact such a product comprises a mixture of antibody-conjugates with a number of molecules of interest varying from 0 to 8 or higher. In other words, antibody-conjugates known from the prior art generally are formed with a DAR with high standard deviation.

For example, gemtuzumab ozogamicin is a heterogeneous mixture of 50% conjugates (0 to 8 calicheamycin moieties per IgG molecules with an average of 2 or 3, randomly linked to solvent exposed lysyl residues of the antibody) and 50% unconjugated antibody (Bross et al., *Clin. Cancer Res.* 2001, 7, 1490; Labrijn et al., *Nat. Biotechnol.* 2009 27, 767, both incorporated by reference). But also for brentuximab vedotin, T-DM1, and other ADCs in the clinic, it is still uncontrollable exactly how many drugs are attaching to any given antibody (drug-antibody ratio, DAR) and the ADC is obtained as a statistical distribution of conjugates. Whether the optimal number of drugs per antibody is for example two, four or more, attaching them in a predictable number and in predictable locations through site-specific conjugation with a narrow standard deviation is still problematic.

SUMMARY OF THE INVENTION

The present invention relates to a process for the preparation of a modified antibody, comprising contacting an antibody comprising a core N-acetylglucosamine (GlcNAc) substituent with a compound of the formula $S(A)_x$-P in the presence of a suitable catalyst, wherein said core N-acetylglucosamine substituent is optionally fucosylated, wherein said catalyst comprises a mutant catalytic domain from a galactosyltransferase, wherein $S(A)_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP), and wherein a modified antibody is defined as an antibody comprising a GlcNAc-$S(A)_x$ substituent bonded to the antibody via C1 of the N-acetylglucosamine of said GlcNAc-$S(A)_x$ substituent. Optionally, the GlcNAc of said GlcNAc-$S(A)_x$ substituent is fucosylated.

The invention also relates to a modified antibody comprising a GlcNAc-$S(A)_x$ substituent, wherein GlcNAc is an N-acetylglucosamine, wherein $S(A)_x$ is a sugar derivative comprising x functional groups A wherein A is selected from the group consisting of an azido group, a keto group and an alkynyl group and x is 1, 2, 3 or 4, wherein said GlcNAc-$S(A)_x$ substituent is bonded to the antibody via C1 of the N-acetylglucosamine of said GlcNAc-$S(A)_x$ substituent, and wherein said N-acetylglucosamine is optionally fucosylated.

The invention also relates to a process for the preparation of an antibody-conjugate, comprising reacting the modified antibody according to the invention with a linker-conjugate, wherein said linker-conjugate comprises a functional group B and one or more molecules of interest, wherein said functional group B is a functional group that is capable of reacting with a functional group A of a GlcNAc-$S(A)_x$ substituent on said modified antibody.

In addition, the invention relates to a process for the preparation of an antibody-conjugate, comprising reacting the modified antibody according to the invention with a linker-conjugate, wherein said linker-conjugate comprises a (hetero)cycloalkynyl group or a terminal alkynyl group and one or more molecule of interest.

The invention further relates to an antibody-conjugate obtainable by the process for the preparation of an antibody-conjugate according to the invention.

The modified antibody, the antibody-conjugate and the processes for the preparation thereof according to the invention have several advantages over the processes, modified antibodies and antibody-conjugates known in the art.

As was described above, the known processes for conjugation of a linker-toxin entities to antibodies still needs to be improved, in terms of control of both site-specificity and stoichiometry. Despite the ability of ADCs to home in on their targets, the amount of drug estimated to get inside tumors cells is typically <2% of an administered dose. This problem is amplified by the unpredictable conjugation results of ADCs known in the art. It is important to avoid underconjugated antibodies, which decrease the potency, as well as highly conjugated species, which may have markedly decreased circulating half-lives, impaired binding to the target protein, and increased toxicity.

For antibody-drug conjugates, a measure for the loading of molecules of interest (e.g. drugs, active substances) onto the antibody is the so-called Drug to Antibody Ratio (DAR), which gives the average number of active substance molecules per antibody, calculated from a statistical distribution. The theoretical maximum value of DAR for a certain type of ADC is equal to the number of anchoring sites. As was described above, processes for the preparation of ADCs known from the prior art generally result in a product comprising a mixture of antibody-conjugates with a varying number of molecules of interest present in each antibody-conjugate, and in a DAR with a high standard deviation.

One of the advantages of the modified antibodies and the antibody-conjugates according to the invention is that these antibodies and antibody-conjugates are homogeneous, both in site-specificity and stoichiometry. Said modified antibodies and antibody-conjugates are obtained with a DAR very near to the theoretical value, and with a very low standard deviation. This also means that the antibody-conjugates according to the invention result in a more consistent product for preclinical testing.

In a preferred embodiment, the modified antibody and antibody-conjugate according to the invention are homogeneous, both in site-specificity and stoichiometry. Herein, an antibody or an antibody-conjugate is considered homogeneous when conjugation is effected only at a predetermined site and with predetermined drug-antibody ratio. An antibody-conjugate is heterogeneous when conjugation of the antibody takes place at different sites in the antibody, leading to a mixture of products with unpredictable drug-antibody ratio. In the latter case, the drug-antibody ratio will be an average of the whole group of antibody-drug conjugates.

In another preferred embodiment, the antibody-conjugate according to the invention has a DAR that is within 10% of its theoretical value.

Another advantage of the processes and antibodies according to the invention involves the reduction of waste in manufacturing, thereby enhancing companies' cost-of-goods.

Furthermore, when an azide-modified antibody according to the invention is coupled to a linker-conjugate comprising an alkynyl group, or when an alkyne-modified antibody according to the invention is coupled to a linker-conjugate comprising an azide moiety, via a cycloaddition reaction, the resulting triazoles are not susceptible to hydrolysis or other degradation pathways. When a ketone-modified antibody according to the invention is coupled to a linker-conjugate comprising a hydroxylamine or a hydrazine, the resulting oximes or hydrazones are also relatively inert at neutral conditions.

Additional advantages are thus the stability of antibody-conjugates according to the invention, as well as the straightforward and generally applicable process for the introduction of an azido group, a keto group or an alkynyl group into an antibody.

As was described above, enzymatic conjugation of an unnatural sugar to the terminal GlcNAc of an oligomeric glycan attached to an antibody, in the presence of mutant galactosyltransferase Y289L, as was shown in FIG. 3, is known in the art.

To date, however, the suitability of mutant galactosyltransferases known in the art for the transfer of sugar nucleotides or sugar derivative nucleotides to a core-GlcNAc-substituent on an antibody, and the suitability of such a strategy for the generation of antibody-conjugates, had not been demonstrated yet. In the processes known in the prior art, a sugar nucleotide or sugar derivative nucleotide is transferred to a terminal GlcNAc of an oligo- or polysaccharide glycan bonded to an antibody.

In addition, to date the suitability of mutant galactosyltransferases known in the art for the transfer of sugar nucleotides or sugar derivative nucleotides to internal sugars and sugar derivatives had not been demonstrated. With the processes according to the invention, it is now possible to transfer a sugar derivative comprising functional groups such as one or more azido, keto and/or alkyne groups, to a core-GlcNAc substituent present on an antibody, irrespective of whether said GlcNAc is fucosylated or not. Advantageously, removal of fucose prior to the process according to the invention is therefore not necessary, since an antibody mixture comprising both core-GlcNAc and core-GlcNAc (Fuc) substituents may be used in the process.

DESCRIPTION OF THE FIGURES

FIG. 10b shows the structure of non-cleavable BCN-MMAF conjugate 57.

FIG. 11 shows the reaction scheme for the synthesis of cleavable DIBAC-vc-PABA-MMAF 41.

FIG. 13 shows the structures of three functionalized biotinylating reagents 45-47.

DETAILED DESCRIPTION OF THE INVENTION

Definitions

Figure 1:
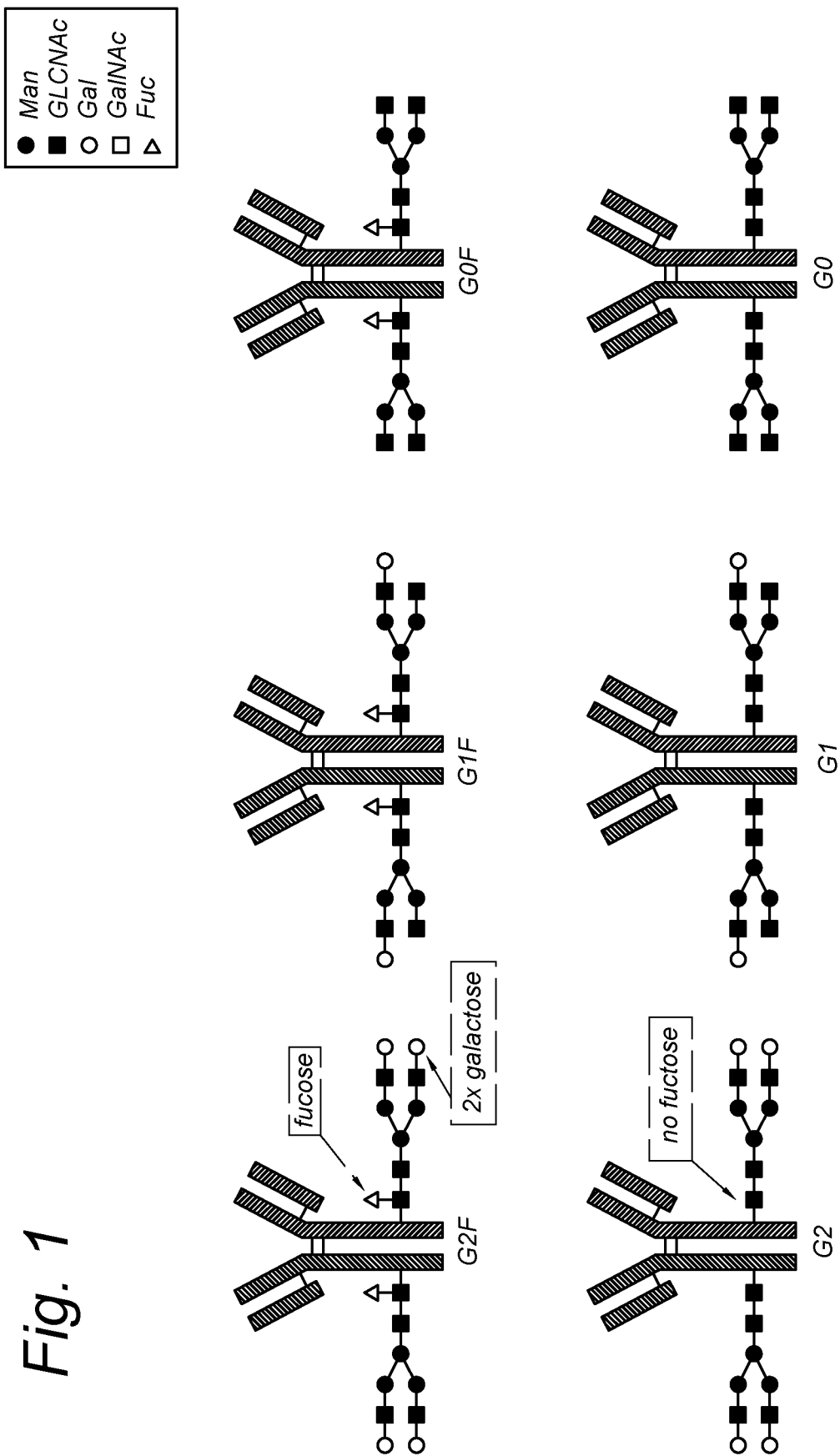
FIG. 1 shows different glycoforms of antibody glycans G2F, G1F, G0F, G2, G1 and G0.
Figure 2:
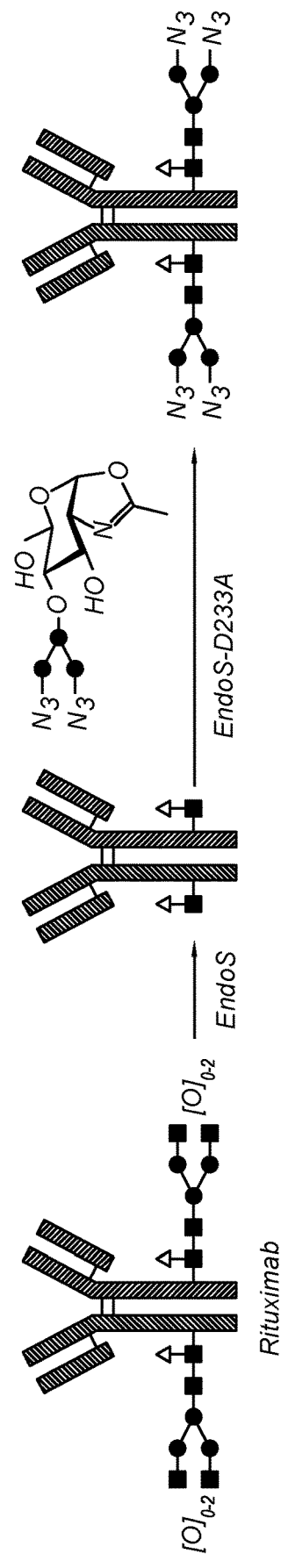
FIG. 2 shows a process for the transfer of a tetrasaccharide comprising two azido groups to a core-GlcNAc substituent in the presence of mutant EndoS-D233A, resulting in a modified antibody comprising four azido groups, as disclosed in *J. Am. Chem. Soc.* 2012, 134, 12308.
Figure 3:
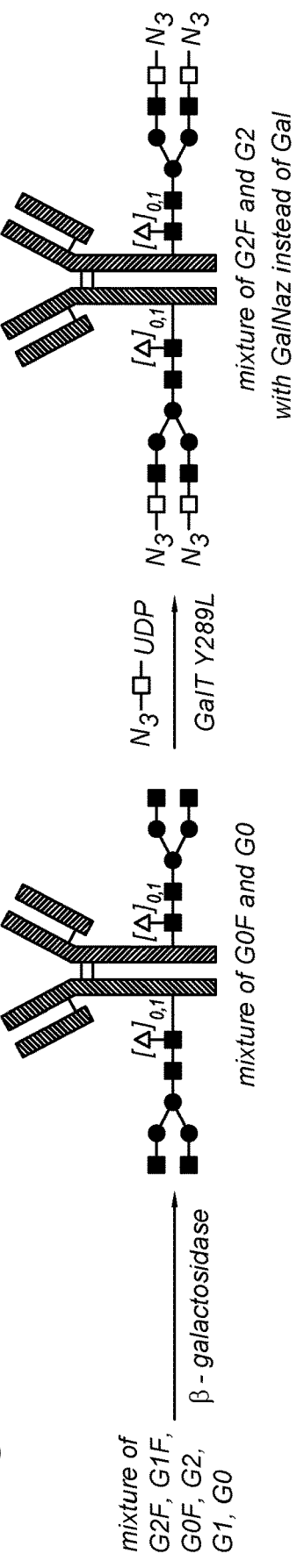
FIG. 3 shows a process for the transfer of GalNAz to the terminal GlcNAc residues of an antibody glycan, leading to a modified antibody comprising four azido groups, as disclosed in *Bioconjugate Chem.* 2009, 20, 1228.

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds disclosed in this description and in the claims may further exist as exo and endo diastereoisomers. Unless stated otherwise, the description of any compound in the description and in the claims is meant to include both the individual exo and the individual endo diastereoisomers of a compound, as well as mixtures thereof. When the structure of a compound is depicted as a specific endo or exo diastereomer, it is to be understood that the invention of the present application is not limited to that specific endo or exo diastereomer.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application. When the structure of a compound is depicted as a specific cis or trans isomer, it is to be understood that the invention of the present application is not limited to that specific cis or trans isomer.

The compounds disclosed in this description and in the claims may further exist as regioisomers. Unless stated otherwise, the description of any compound in the description and in the claims is meant to include both regioisomers of a compound, as well as mixtures thereof. When the structure of a compound is depicted as a specific regioisomer, it is to be understood that the invention of the present application is not limited to that specific regioisomer.

Unsubstituted alkyl groups have the general formula $C_nH_{2n+1}$ and may be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of alkyl groups include methyl, ethyl, propyl, 2-propyl, t-butyl, 1-hexyl, 1-dodecyl, etc.

An aryl group comprises six to twelve carbon atoms and may include monocyclic and bicyclic structures. Optionally, the aryl group may be substituted by one or more substituents further specified in this document. Examples of aryl groups are phenyl and naphthyl.

A heteroaryl group comprises five to twelve carbon atoms wherein one to four carbon atoms are replaced by heteroatoms selected from the group consisting of oxygen, nitrogen, phosphorus and sulphur. A heteroaryl group may have a monocyclic or a bicyclic structure. Optionally, the heteroaryl group may be substituted by one or more substituents further specified in this document. Examples of suitable heteroaryl groups include pyridinyl, quinolinyl, pyrimidinyl, pyrazinyl, pyrazolyl, pyrrolyl, furanyl, benzofuranyl, indolyl, purinyl, benzoxazolyl, thienyl, phospholyl and oxazolyl.

Arylalkyl groups and alkylaryl groups comprise at least seven carbon atoms and may include monocyclic and bicyclic structures. Optionally, the arylalkyl groups and alkylaryl may be substituted by one or more substituents further specified in this document. An arylalkyl group is for example benzyl. An alkylaryl group is for example 4-t-butylphenyl.

An alkynyl group comprises one or more carbon-carbon triple bonds. An unsubstituted alkynyl group comprising one triple bond has the general formula $C_nH_{2n-3}$. A terminal alkynyl is an alkynyl group wherein the triple bond is located at a terminal position of the alkynyl group. Optionally, the alkynyl group is substituted by one or more substituents further specified in this document, and/or interrupted by heteroatoms selected from the group of oxygen, nitrogen and sulphur. Examples of alkynyl groups include ethynyl, propynyl, butynyl, octynyl, etc.

A cycloalkynyl group is a cyclic alkynyl group. An unsubstituted cycloalkynyl group comprising one triple bond has the general formula $C_nH_{2n-5}$. Optionally, a cycloalkynyl group is substituted by one or more substituents further specified in this document. An example of a cycloalkynyl group is cyclooctynyl.

A heterocycloalkynyl group is a cycloalkynyl group interrupted by heteroatoms selected from the group of oxygen, nitrogen and sulphur. Optionally, a heterocycloalkynyl group is substituted by one or more substituents further specified in this document. An example of a heterocycloalkynyl group is azacyclooctynyl.

A (hetero)aryl group comprises an aryl group and a heteroaryl group. An alkyl(hetero)aryl group comprises an alkylaryl group and an alkylheteroaryl group. A (hetero)arylalkyl group comprises a arylalkyl group and a heteroarylalkyl groups. A (hetero)alkynyl group comprises an alkynyl group and a heteroalkynyl group. A (hetero)cycloalkynyl group comprises an cycloalkynyl group and a heterocycloalkynyl group.

A (hetero)cycloalkyne compound is herein defined as a compound comprising a (hetero)cycloalkynyl group.

Several of the compounds disclosed in this description and in the claims may be described as fused (hetero)cycloalkyne compounds, i.e. (hetero)cycloalkyne compounds wherein a second ring structure is fused, i.e. annelated, to the (hetero)cycloalkynyl group. For example in a fused (hetero)cyclooctyne compound, a cycloalkyl (e.g. a cyclopropyl) or an arene (e.g. benzene) may be annelated to the (hetero)cyclooctynyl group. The triple bond of the (hetero)cyclooctynyl group in a fused (hetero)cyclooctyne compound may be located on either one of the three possible locations, i.e. on the 2, 3 or 4 position of the cyclooctyne moiety (numbering according to "IUPAC Nomenclature of Organic Chemistry", Rule A31.2). The description of any fused (hetero)cyclooctyne compound in this description and in the claims is meant to include all three individual regioisomers of the cyclooctyne moiety.

When an alkyl group, a (hetero)aryl group, alkyl(hetero)aryl group, a (hetero)arylalkyl group, a (hetero)cycloalkynyl group is optionally substituted, said groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R^6)_3Si$—, wherein $R^6$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S.

An antibody is a protein generated by the immune system that is capable of recognizing and binding to a specific antigen. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, $F(ab')_2$, Fv fragment or Fc fragment from a cleaved antibody, a scFv-Fc fragment, a minibody, a diabody or a scFv. Furthermore, the term includes genetically engineered derivatives of an antibody. Antibodies, fragments of antibodies and genetically engineered antibodies may be obtained by methods that are known in the art. Suitable marketed antibodies include, amongst others, abciximab, rituximab, basiliximab, palivizumab, infliximab, trastuzumab, alemtuzumab, adalimumab, tositumomab-I131, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

The general term "sugar" is herein used to indicate a monosaccharide, for example glucose (Glc), galactose (Gal), mannose (Man) and fucose (Fuc). The term "sugar derivative" is herein used to indicate a derivative of a monosaccharide sugar, i.e. a monosaccharide sugar comprising substituents and/or functional groups. Examples of a sugar derivative include amino sugars and sugar acids, e.g. glucosamine (GlcN), galactosamine (GalN) N-acetylglucosamine (GlcNAc), N-acetylgalactosamine (GalNAc), N-acetylneuraminic acid (NeuNAc) and N-acetylmuramic acid (MurNAc), glucuronic acid (GlcA) and iduronic acid (IdoA). Examples of a sugar derivative also include compounds herein denoted $S(A)_x$, wherein S is a sugar or a sugar derivative, and wherein S comprises x functional groups A.

A core-N-acetylglucosamine substituent (core-GlcNAc substituent) is herein defined as a GlcNAc that is bonded via C1 to an antibody, preferably via an N-glycosidic bond to the amide nitrogen atom in the side chain of an asparagine amino acid of the antibody. The core-GlcNAc substituent may be present at a native glycosylation site of an antibody, but it may also be introduced on a different site on the antibody. Herein, a core-N-acetylglucosamine substituent is a monosaccharide substituent, or if said core-GlcNAc substituent is fucosylated, a disaccharide core-(Fucα1-6)GlcNAc substituent, further referred to as GlcNAc(Fuc). Herein, a "core-GlcNAc substituent" is not to be confused with a "core-GlcNAc". A core-GlcNAc is herein defined as the inner GlcNAc that is part of a poly- or an oligosaccharide comprising more than two saccharides, i.e. the GlcNAc via which the poly- or oligosaccharide is bonded to an antibody.

An antibody comprising a core-N-acetylglucosamine substituent as defined herein is thus an antibody, comprising a monosaccharide core-GlcNAc substituent as defined above, or if said core-GlcNAc substituent is fucosylated, a disaccharide core-GlcNAc(Fuc) substituent.

If a core-GlcNAc substituent or the GlcNAc in a GlcNAc-$S(A)_x$ substituent is fucosylated, fucose is most commonly linked α-1,6 to C6 of the core-GlcNAc substituent. A fucosylated core-GlcNAc substituent is denoted core-Glc-NAc(Fuc), a fucosylated GlcNAc-S(A)$_x$ substituent is denoted GlcNAc(Fuc)-S(A)$_x$.

The terms "treatment," "treating," and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes preventing the disease from occurring in a subject which may be predisposed to the disease but has not yet been diagnosed as having it; inhibiting the disease, i.e., arresting its development; relieving the disease, i.e., causing regression of the disease.

Process for the Preparation of a Modified Antibody

The present invention relates to a process for the preparation of a modified antibody, comprising contacting an antibody comprising a core N-acetylglucosamine substituent (a core-GlcNAc substituent) with a compound of the formula S(A)$_x$-P in the presence of a suitable catalyst, wherein said core-GlcNAc substituent is optionally fucosylated, wherein said catalyst comprises a mutant catalytic domain from a galactosyltransferase, wherein S(A)$_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP), and wherein a modified antibody is defined as an antibody comprising a GlcNAc-S(A)$_x$ substituent bonded to the antibody via C1 of the N-acetylglucosamine of said GlcNAc-S(A)$_x$ substituent.

In a preferred embodiment, the antibody comprising a core-N-acetylglucosamine substituent (core-GlcNAc substituent) is a monoclonal antibody (mAb). Preferably, said antibody is selected from the group consisting of IgA, IgD, IgE, IgG and IgM antibodies. More preferably, said antibody is an IgG antibody, and most preferably said antibody is an IgG1 antibody. When said antibody is a whole antibody, the antibody preferably comprises one or more, more preferably one, core-GlcNAc substituent on each heavy chain, said core-GlcNAc substituent being optionally fucosylated. Said whole antibody thus preferably comprises two or more, preferably two, optionally fucosylated, core-GlcNAc substituents. When said antibody is a single chain antibody or an antibody fragment, e.g. a Fab fragment, the antibody preferably comprises one or more core-GlcNAc substituent, which is optionally fucosylated.

In the antibody comprising a core-GlcNAc substituent (i.e. the starting material of the process), said core-GlcNAc substituent may be situated anywhere on the antibody, provided that said substituent does not hinder the antigen-binding site of the antibody. In one embodiment, said core-GlcNAc substituent is situated in the Fc fragment of the antibody, more preferably in the C$_H$2 domain. In another embodiment, said core-GlcNAc substituent is situated on the Fab fragment of the antibody.

In one embodiment, the antibody comprising a core-GlcNAc substituent, wherein said core-GlcNAc substituent is optionally fucosylated, is of the Formula (1), wherein AB represents an antibody, GlcNAc is N-acetylglucosamine, Fuc is fucose, b is 0 or 1 and y is 1 to 20.

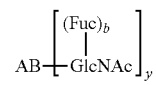

In a preferred embodiment, y is 1 to 10, more preferably y is 1, 2, 3, 4, 5, 6, 7 or 8, even more preferably y is 1, 2, 3 or 4 and most preferably y is 1 or 2.

An embodiment of the process according to the invention wherein the starting material of the process is an antibody comprising one optionally fucosylated core-GlcNAc substituent (1a, y is 1) and an embodiment wherein said starting material is an antibody comprising two optionally fucosylated core-GlcNAc substituents (1b, y is 2) are shown in Scheme 1, wherein AB represents an antibody and wherein b is 0 or 1. S(A)$_x$ and P are as defined above.

Modification of antibody (1a) leads to a modified antibody comprising one GlcNAc-S(A)$_x$ substituent (2) and modification of antibody (1b) leads to a modified antibody comprising two GlcNAc-S(A)$_x$ substituents (3).

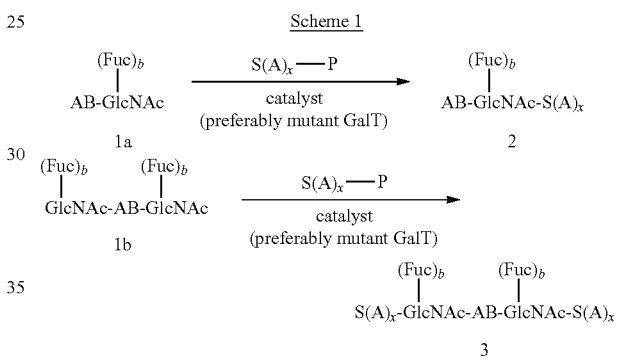

Several suitable catalysts for the process according to the invention are known in the art. A suitable catalyst for a specific process is a catalyst wherefore the specific sugar derivative nucleotide S(A)$_x$-P in that specific process is a substrate. Preferably, the catalyst is selected from the group of galactosyltransferases, more preferably from the group of β(1,4)-galactosyltransferases or α(1,3)-N-galactosyltransferases, even more preferably from the group of β(1,4)-galactosyltransferases or α(1,3)-N-galactosyltransferases comprising a mutant catalytic domain.

A suitable catalyst is for example a catalyst that comprises a mutant catalytic domain from a β(1,4)-galactosyltransferase I. A catalytic domain herein refers to an amino acid segment that folds into a domain that is able to catalyze the linkage of the specific sugar derivative nucleotide S(A)$_x$-P to the core-GlcNAc substituent in a specific process according to the invention. A catalytic domain may have an amino acid sequence as found in a wild-type enzyme, or have an amino acid sequence that is different from a wild-type sequence. A catalytic domain having an amino acid sequence that is different from a wild-type sequence is herein referred to as a mutant catalytic domain. The mutation may e.g. comprise a single amino acid change (a point mutation), but also a multiple amino acid change (e.g of 1 to 10, preferably of 1 to 6, more preferably of 1, 2, 3 or 4, even more preferably of 1 or 2 amino acids), or a deletion or insertion of one or more (e.g of 1 to 10, preferably 1 to 6, more preferably of 1, 2, 3 or 4, even more preferably of 1 or 2) amino acids.

Said mutant catalytic domain may be present in a full-length enzyme, e.g. a β(1,4)-galactosyltransferase I enzyme, but also in e.g. a polypeptide fragment or a recombinant polypeptide comprising said mutant catalytic domain, optionally linked to additional amino acids.

β(1,4)-galactosyltransferase I is herein further referred to as GalT. Such mutant GalT catalytic domains are for example disclosed in WO 2004/063344 (National Institutes of Health), incorporated by reference herein. WO 2004/063344 discloses Tyr-289 mutants of GalT, which are referred to as Y289L, Y289N and Y289I. The method of preparation of said mutant catalytic domains Y289L, Y289N and Y289I is disclosed in detail in WO 2004/063344, p. 34, l. 6-p. 36, l. 2, incorporated by reference herein.

Mutant GalT domains that catalyze the formation of a glucose-β(1,4)-N-acetylglucosamine bond are disclosed in WO 2004/063344 on p. 10, l, 25-p. 12, l. 4 (incorporated by reference herein). Mutant GalT domains that catalyze the formation of an N-acetylgalactosamine-β(1,4)-N-acetylglucosamine bond are disclosed in WO 2004/063344 on p. 12, l, 6-p. 13, l. 2 (incorporated by reference herein). Mutant GalT domains that catalyze the formation of a N-acetylglucosamine-β(1,4)-N-acetylglucosamine bond and a mannose-β(1,4)-N-acetylglucosamine bond are disclosed in WO 2004/063344 on p. 12, l, 19-p. 14, l. 6 (incorporated by reference herein). The disclosed mutant GalT domains may be included within full-length GalT enzymes, or in recombinant molecules containing the catalytic domains, as is disclosed in WO 2004/063344 on p. 14, l, 31-p. 16, l. 28, incorporated by reference herein.

Another mutant GalT domain is for example Y284L, disclosed by Bojarová et al., *Glycobiology* 2009, 19, 509, incorporated by reference herein. The mutation in position 284 concerns a tyrosine residue.

Another mutant GalT domain is for example R228K, disclosed by Qasba et al., *Glycobiology* 2002, 12, 691, incorporated by reference herein, wherein Arg228 is replaced by lysine.

In a preferred embodiment of the process for the preparation of a modified antibody according to the invention, said catalyst is a catalyst comprising a mutant catalytic domain from a β(1,4)-galactosyltransferase, preferably a bovine β(1,4)-galactosyltransferase. In a further preferred embodiment, said catalyst is a catalyst comprising a GalT mutant catalytic domain selected from the group consisting of Y289L, Y289N, Y289I, Y284L and R228K, preferably Y289L. In a specific embodiment, the catalyst is a catalyst comprising a mutant catalytic domain from a β(1,4)-galactosyltransferase, preferably selected from the group consisting of GalT Y289L, GalT Y289N and GalT Y289I, more preferably GalT Y289L or GalT Y289N, and most preferably GalT Y289L.

In another embodiment, the catalyst is a catalyst comprising a mutant catalytic domain from a bovine β(1,4)-galactosyltransferase, selected from the group consisting of GalT Y289F, GalT Y289M, GalT Y289V, GalT Y289G, GalT Y289I and GalT Y289A, preferably selected from the group consisting of GalT Y289F and GalT Y289M. GalT Y289F, GalT Y289M, GalT Y289V, GalT Y289G, GalT Y289I and GalT Y289A may be provided via site-directed mutagenesis processes, in a similar manner as disclosed in WO 2004/063344, in Qasba et al., *Prot. Expr. Pur.* 2003, 30, 219 and in Qasba et al., *J. Biol. Chem.* 2002, 277, 20833 (all incorporated by reference) for Y289L, Y289N and Y289I. In GalT Y289F the tyrosine amino acid (Y) at position 289 is replaced by a phenyl alanine (F) amino acid, in GalT Y289M said tyrosine is replaced by a methionine (M) amino acid, in GalT Y289V by a valine (V) amino acid, in GalT Y289G by a glycine (G) amino acid, in GalT Y289I by an isoleucine (I) amino acid and in Y289A by an analine (A) amino acid.

Another type of suitable catalysts is a catalyst based on α(1,3)-N-galactosyltransferase (further referred to as a3Gal-T), preferably α(1,3)-N-acetylgalactosaminyltransferase (further referred to as a3GalNAc-T), as disclosed in WO 2009/025646, incorporated by reference herein. Mutation of a3Gal-T can broaden donor specificity of the enzyme, and make it an a3GalNAc-T. Mutation of a3GalNAc-T can broaden donor specificity of the enzyme. Polypeptide fragments and catalytic domains of α(1,3)-N-acetylgalactosaminyltransferases are disclosed in WO 2009/025646 on p. 26, l. 18-p. 47, l. 15 and p. 77, l. 21-p. 82, l. 4 (both incorporated by reference herein).

In one embodiment, the catalyst is a wild-type galactosyltransferase, more preferably a wild-type β(1,4)-galactosyltransferase or a wild-type β(1,3)-N-galactosyltransferase, and even more preferably a wild-type β(1,4)-galactosyltransferase I. β(1,4)-Galactosyltransferase is herein further referred to as GalT. Even more preferably, the β(1,4)-galactosyltransferase is selected from the group consisting of a bovine β(1,4)-Gal-T1, a human β(1,4)-Gal-T1, a human β(1,4)-Gal-T2, a human β(1,4)-Gal-T3 and a human β(1,4)-Gal-T4. Even more preferably, the β(1,4)-galactosyltransferase is a β(1,4)-Gal-T1. When the catalyst is a wild-type β(1,3)-N-galactosyltransferase, a human β(1,3)-Gal-T5 is preferred.

This embodiment wherein the catalyst is a wild-type galactosyltransferase is particularly preferred when a functional group A in sugar derivative $S(A)_x$ is present on C2 or C6, preferably C6, of said sugar derivative. In this embodiment, it is further preferred that $Su(A)_x$ comprises one functional group A, i.e. preferably x is 1. P, $Su(A)_x$ and $Su(A)_x$-P are described in more detail below.

Accordingly, the invention therefore also relates to a process for the preparation of a modified glycoprotein, the process comprising contacting an antibody comprising a core N-acetylglucosamine (GlcNAc) substituent with a compound of the formula $S(A)_x$-P in the presence of a suitable catalyst, wherein said catalyst is a wild-type galactosyltransferase, wherein $S(A)_x$ is a sugar derivative comprising x functional groups A wherein A is independently selected from the group consisting of an azido group, a keto group and an alkynyl group and wherein x is 1, wherein P is selected from the group consisting of uridine diphosphate (UDP), guanosine diphosphate (GDP) and cytidine diphosphate (CDP), and wherein a modified antibody is defined as an antibody comprising a GlcNAc-$S(A)_x$ substituent bonded to the antibody via C1 of the N-acetylglucosamine of said GlcNAc-$S(A)_x$ substituent.

The process for the preparation of a modified antibody according to the invention is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer.

The process is preferably performed at a temperature in the range of about 4 to about 50° C., more preferably in the range of about 10 to about 45° C., even more preferably in the range of about 20 to about 40° C., and most preferably in the range of about 30 to about 37° C.

The process is preferably performed a pH in the range of about 5 to about 9, preferably in the range of about 5.5 to about 8.5, more preferably in the range of about 6 to about 8. Most preferably, the process is performed at a pH in the range of about 7 to about 8.

In the process according to the invention, an antibody mixture may be used as the starting antibody, said mixture comprising antibodies comprising one or more core-GlcNAc substituents and/or one or more core-GlcNAc(Fuc) substituents. For example when the starting antibody mixture comprises a whole antibody with one optionally fucosylated core-GlcNAc substituent on each heavy chain, the whole antibody may comprise two core-GlcNAc substituents, or two core-GlcNAc(Fuc) substituents, or one core-GlcNAc substituent and one core-GlcNAc(Fuc) substituent.

The GlcNAc in the monosaccharide core-GlcNAc substituent is on the terminal position, whereas the GlcNAc in the disaccharide core-GlcNAc(Fuc) substituent is on an internal position, bonded to the antibody via C1 and to Fuc via C6. Since, as was described above, said galactosyltransferases mutant enzyme catalysts are also able to recognize internal sugars and sugar derivatives as an acceptor, sugar derivative $S(A)_x$ is linked to the core-GlcNAc substituent in the process according to the invention, irrespective of whether said GlcNAc is fucosylated or not. Advantageously, removal of fucose prior to the process according to the invention is therefore not necessary, since an antibody mixture comprising both core-GlcNAc and core-GlcNAc (Fuc) substituents may be used in the process. However, if desired, fucose may be removed from any core-GlcNAc (Fuc) substituents prior to the process according to the invention, for example by defucosylation in the presence of α-fucosidase as is known in the art.

$S(A)_x$ is defined as a sugar derivative comprising x functional groups A, wherein A is independently selected from the group consisting of an azido group, a keto group and an alkynyl group, and wherein x is 1, 2, 3 or 4.

An azido group is an azide functional group $—N_3$. A keto group is a $—[C(R^7)_2]_oC(O)R^6$ group, wherein $R^6$ is a methyl group or an optionally substituted $C_2$-$C_{24}$ alkyl group, $R^7$ is independently selected from the group consisting of hydrogen, halogen and $R^6$, and o is 0-24, preferably 0-10, and more preferably 0, 1, 2, 3, 4, 5 or 6. Preferably, $R^7$ is hydrogen. An alkynyl group is preferably a terminal alkynyl group or a (hetero)cycloalkynyl group as defined above. In one embodiment the alkynyl group is a $—[C(R^7)_2]_oC\equiv C—R^7$ group, wherein $R^7$ and o are as defined above; $R^7$ is preferably hydrogen.

The sugar derivative $S(A)_x$ may comprise one or more functional groups A. When $S(A)_x$ comprises two or more functional groups A, each functional group A is independently selected, i.e. one $S(A)_x$ may comprise different functional groups A, e.g. an azido group and a keto group, etc. In a preferred embodiment, x is 1 or 2, more preferably x is 1. In another preferred embodiment, functional group A is an azido group or a keto group, more preferably an azido group.

Sugar derivative $S(A)_x$ is derived from a sugar or a sugar derivative S, e.g. an amino sugar or an otherwise derivatized sugar. Examples of sugars and sugar derivatives include galactose (Gal), mannose (Man), glucose (Glc), glucuronic acid (Gcu) and fucose (Fuc). An amino sugar is a sugar wherein a hydroxyl (OH) group is replaced by an amine group and examples include N-acetylglucosamine (GlcNAc) and N-acetylgalactosamine (GalNAc). Examples of an otherwise derivatized sugar include glucuronic acid (Gcu) and N-acetylneuraminic acid (sialic acid).

Sugar derivative $S(A)_x$ is preferably derived from galactose (Gal), mannose (Man), N-acetylglucosamine (GlcNAc), glucose (Glc), N-acetylgalactosamine (GalNAc), glucuronic acid (Gcu), fucose (Fuc) and N-acetylneuraminic acid (sialic acid), preferably from the group consisting of GlcNAc, Glc, Gal and GalNAc. More preferably $S(A)_x$ is derived from Gal or GalNAc, and most preferably $S(A)_x$ is derived from GalNAc.

The one or more functional groups A in $S(A)_x$ may be linked to the sugar or sugar derivative S in several ways. The one or more functional groups A may be bonded to C2, C3, C4 and/or C6 of the sugar or sugar derivative, instead of a hydroxyl (OH) group. It should be noted that, since fucose lacks an OH-group on C6, if A is bonded to C6 of Fuc, then A takes the place of an H-atom.

When A is an azido group, it is preferred that A is bonded to C2, C4 or C6. As was described above, the one or more azide substituents in $S(A)_x$ may be bonded to C2, C3, C4 or C6 of the sugar or sugar derivative S, instead of a hydroxyl (OH) group or, in case of 6-azidofucose (6-AzFuc), instead of a hydrogen atom. Alternatively or additionally, the N-acetyl substituent of an amino sugar derivative may be substituted by an azidoacetyl substituent. In a preferred embodiment $S(A)_x$ is selected from the group consisting of 2-azidoacetamidogalactose (GalNAz), 6-azido-6-deoxygalactose (6-AzGal), 6-azido-6-deoxy-2-acetamidogalactose (6-AzGalNAc), 4-azido-4-deoxy-2-acetamidogalactose (4-AzGalNAc), 6-azido-6-deoxy-2-azidoacetamidogalactose (6-AzGalNAz), 2-azidoacetamidoglucose (GlcNAz), 6-azido-6-deoxyglucose (6-AzGlc), 6-azido-6-deoxy-2-acetamidoglucose (6-AzGlcNAc), 4-azido-4-deoxy-2-acetamidoglucose (4-AzGlcNAc) and 6-azido-6-deoxy-2-azidoacetamidoglucose (6-AzGlcNAz), more preferably from the group consisting of GalNAz, 4-AzGalNAc, GlcNAz and 6-AzGlcNAc. Examples of $S(A)_x$-P wherein A is an azido group are shown below.

When A is a keto group, it is preferred that A is bonded to C2 instead of the OH-group of S. Alternatively A may be bonded to the N-atom of an amino sugar derivative, preferably a 2-amino sugar derivative. The sugar derivative then comprises an $—NC(O)R^6$ substituent. $R^6$ is preferably a $C_2$-$C_{24}$ alkyl group, optionally substituted. More preferably, $R^6$ is an ethyl group. In a preferred embodiment $S(A)_x$ is selected from the group consisting of 2-deoxy-(2-oxopropyl)galactose (2-ketoGal), 2-N-propionylgalactosamine (2-N-propionylGalNAc), 2-N-(4-oxopentanoyl)galactosamine (2-N-LevGal) and 2-N-butyrylgalactosamine (2-N-butyrylGalNAc), more preferably 2-ketoGalNAc and 2-N-propionylGalNAc. Examples of $S(A)_x$-P wherein A is a keto group are shown below.

When A is an alkynyl group, preferably a terminal alkynyl group or a (hetero)cycloalkynyl group, it is preferred that said alkynyl group is present on a 2-amino sugar derivative. An example of S(A)x wherein A is an alkynyl group is 2-(but-3-yonic acid amido)-2-deoxy-galactose. An example of $S(A)_x$-P wherein A is an alkynyl group is shown below.

Compounds of the formula $S(A)_x$-P, wherein a nucleoside monophosphate or a nucleoside diphosphate P is linked to a sugar derivative $S(A)_x$, are known in the art. For example Wang et al., *Chem. Eur. 1* 2010, 16, 13343-13345, Piller et al., *ACS Chem. Biol.* 2012, 7, 753, Piller et al., *Bioorg. Med. Chem. Lett.* 2005, 15, 5459-5462 and WO 2009/102820, all incorporated by reference herein, disclose a number of compounds $S(A)_x$-P and their syntheses.

In a preferred embodiment nucleoside mono- or diphosphate P in $S(A)_x$-P is selected from the group consisting of uridine diphosphate (UDP), guanosine diphosphate (GDP), thymidine diphosphate (TDP), cytidine diphosphate (CDP) and cytidine monophosphate (CMP), preferably UDP.

Several examples (5-10) of uridine diphosphates linked to azido-, keto- and alkynyl-substituted sugars and sugar derivatives, S(A)$_x$-UDP, are shown below.

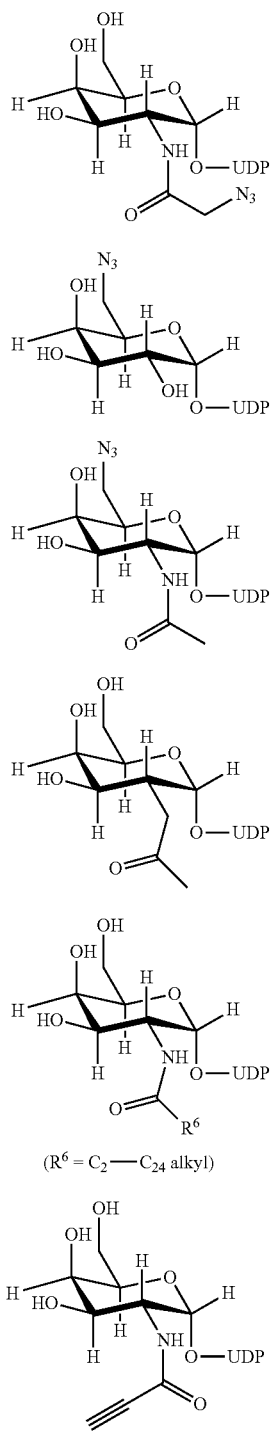

Preferably, S(A)$_x$-P is selected from the group consisting of GalNAz-UDP (5), 6-AzGal-UDP (6), 6-AzGalNAc-UDP (7), 4-AzGalNAz-UDP, 6-AzGalNAz-UDP, 6-AzGlc-UDP, 6-AzGlcNAz-UDP, 2-ketoGal-UDP (8), 2-N-propionylGalNAc-UDP (9, wherein R$^6$ is ethyl) and 2-(but-3-yonic acid amido)-2-deoxy-galactose-UDP (10).

Most preferably, S(A)$_x$-P is GalNAz-UDP (5) or 4-AzGalNAc-UDP (7). The syntheses of GalNAz-UDP (5) and 6-AzGalNAc-UDP (7) are disclosed in Piller et al., *Bioorg. Med. Chem. Lett.* 2005, 15, 5459-5462 and Wang et al., *Chem. Eur. J.* 2010, 16, 13343-13345, both incorporated by reference herein.

The synthesis of 2-ketoGal-UDP (8) is disclosed in Qasba et al., *J. Am. Chem. Soc.* 2003, 125, 16162, in particular in the Supporting Information, both incorporated by reference herein.

The synthesis of 2-(but-3-ynoic acid amido)-2-deoxy-galactose-UDP is disclosed in WO 2009/102820, incorporated by reference herein.

As was described above, in the process for the modification of an antibody according to the invention, S(A)$_x$-P may be any sugar derivative nucleotide that is a substrate for a suitable galactosyltransferase catalyst.

Figure 4:
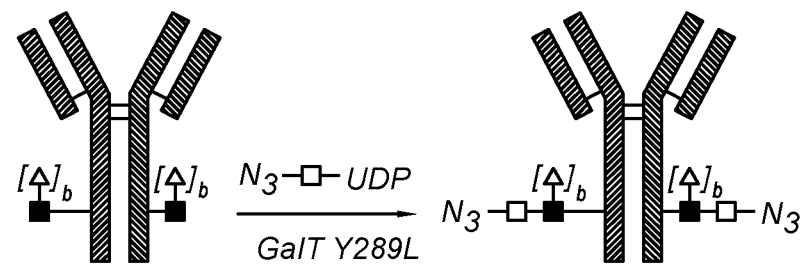
FIG. 4 shows a preferred embodiment of the process for the preparation of an azide-modified antibody, wherein an optionally substituted antibody comprising a core-GlcNAc substituent is reacted with GalNAz-UDP in the presence of GalT Y289L as a catalyst.

A preferred embodiment of the process according to the invention is shown in FIG. 4. FIG. 4 shows a monoclonal antibody (mAb) comprising an, optionally fucosylated (b=0 or 1), core-GlcNAc substituent on each heavy chain of the antibody. These core-GlcNAc (b=0) and core-GlcNAc(Fuc) (b=1) substituents are converted into GlcNAc-GalNAz and GlcNAc(Fuc)-GalNAz substituents, respectively. Said conversion is executed via reaction with GalNAz-UDP (5) in the presence of a mutant GalT Y289L enzyme as a catalyst.

The present invention generally relates to a process for the preparation of a modified antibody, the process comprising:
(a) providing an antibody comprising an, optionally fucosylated, core N-acetylglucosamine substituent (core-GlcNAc substituent), followed by
(b) contacting said antibody with a compound of the formula S(A)$_x$-P in the presence of a suitable catalyst, wherein said catalyst comprises a mutant catalytic domain from a galactosyltransferase, wherein S(A)$_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP), and wherein a modified antibody is defined as an antibody comprising a GlcNAc-S(A)$_x$ substituent bonded to the antibody via C1 of the N-acetylglucosamine of said GlcNAc-S(A)$_x$ substituent.

The antibody comprising an optionally fucosylated core-GlcNAc substituent may be provided in various ways. Said antibodies, e.g. whole antibodies, antibody fragments, genetically engineered antibodies, etc. may be provided by methods that are known to the person skilled in the art. For example Fab or Fc fragments may be prepared by proteolytic digestion of substantially intact immunoglobulin molecules with papain, or by recombinant expression of the desired portions of an immunoglobulin heavy and light chain.

In one embodiment, the process according to the invention further comprises the deglycosylation of an antibody glycan having a core N-acetylglucosamine, in the presence of an endoglycosidase, in order to obtain an antibody comprising a core N-acetylglucosamine substituent, wherein said core N-acetylglucosamine and said core N-acetylglucosamine substituent are optionally fucosylated. Depending on the nature of the glycan, a suitable endoglycosidase may be selected. The endoglycosidase is preferably selected from the group consisting of Endo S, Endo A, Endo F, Endo M, Endo D and Endo H enzymes and/or a combination thereof, the selection of which depends on the nature of the glycan. In a further preferred embodiment, the endoglycosidase is Endo S, Endo S49, Endo F or a combination thereof. In a further preferred embodiment, the endoglycosidase is Endo S, Endo F or a combination thereof. In a further preferred embodiment, the endoglycosidase is Endo S. In another preferred embodiment the endoglycosidase is Endo S49.

An antibody glycan having a core N-acetylglucosamine is herein defined as an antibody comprising a glycan that is bonded to the antibody via C1 of an, optionally fucosylated, GlcNAc (the core-GlcNAc). Apart from said core-GlcNAc and the optional Fuc, said glycan comprises at least one more sugar or sugar derivative.

Figure 5:
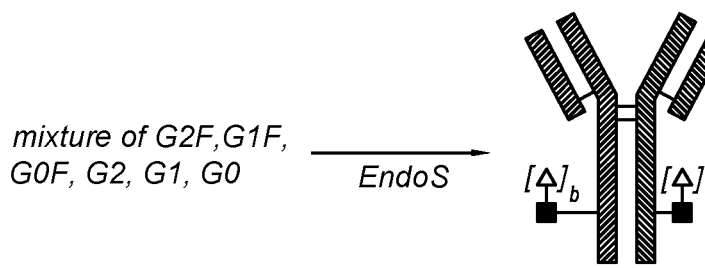
FIG. 5 shows the deglycosylation of a mixture of glycoforms in the presence of EndoS as a catalyst.

A preferred embodiment of said deglycosylation step of the process is shown in FIG. 5, where a mixture of antibody glycoforms G2F, G1F, G0F, G2, G1 and G0, and possibly more glycoforms such as triantennary glycans, is converted into antibodies comprising an, optionally fucosylated (b is 0 or 1), core N-acetylglucosamine substituent. Glycoforms G2F, G1F, G0F, G2, G1 and G0 are shown in FIG. 1.

The present invention therefore also relates to a process for the preparation of a modified antibody, the process comprising:
(a) deglycosylation of an antibody glycan having a core N-acetylglucosamine, in the presence of an endoglycosidase, in order to obtain an antibody comprising a core N-acetylglucosamine substituent, wherein said core N-acetylglucosamine substituent is optionally fucosylated, followed by
(b) contacting said antibody with a compound of the formula $S(A)_x$-P in the presence of a suitable catalyst, wherein said catalyst comprises a mutant catalytic domain from a galactosyltransferase, wherein $S(A)_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP), and wherein a modified antibody is defined as an antibody comprising a GlcNAc-$S(A)_x$ substituent bonded to the antibody via C1 of the N-acetylglucosamine of said GlcNAc-$S(A)_x$ substituent.

The present invention also relates to a process for the preparation of a modified antibody, the process comprising:
(a) deglycosylation of an antibody glycan having a core N-acetylglucosamine, in the presence of an endoglycosidase, in order to obtain an antibody comprising a core N-acetylglucosamine substituent, wherein said core N-acetylglucosamine substituent is optionally fucosylated, wherein said core N-acetylglucosamine substituent is bonded via an N-glycosidic bond to the amide nitrogen atom in the side chain of an asparagine amino acid of the antibody, and wherein said endoglycosidase is Endo S, Endo S49, Endo F, or a combination thereof; followed by
(b) contacting said antibody with a compound of the formula $S(A)_x$-P in the presence of a suitable catalyst, wherein said catalyst comprises a mutant catalytic domain from a galactosyltransferase, wherein $S(A)_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP),
wherein a modified antibody is defined as an antibody comprising a GlcNAc-$S(A)_x$ substituent bonded to the antibody via C1 of the N-acetylglucosamine of said GlcNAc-S$(A)_x$ substituent.

In a preferred embodiment, said endoglycosidase is selected from the group consisting of Endo S, Endo F, or a combination thereof. In a further preferred embodiment, the endoglycosidase is Endo S, Endo F or a combination thereof. In an even more preferred embodiment, said endoglycosidase is Endo S. In another preferred embodiment, said endoglycosidase is Endo S49. In another preferred embodiment, said endoglycosidase is selected from the group consisting of Endo S, Endo S49, Endo F and/or a combination thereof. More preferably, said endoglycosidase is Endo S or Endo S49. Most preferably, said endoglycosidase is Endo S or Endo F.

Endo S, Endo A, Endo F, Endo M, Endo D and Endo H are known to the person skilled in the art. Endo S49 is described in WO 2013/037824 (Genovis AB), incorporated by reference herein. Endo S49 is isolated from *Streptococcus pyogenes* NZ131 and is a homologue of Endo S. Endo S49 has a specific endoglycosidase activity on native IgG and cleaves a larger variety of Fc glycans than Endo S.

In a preferred embodiment, said core N-acetylglucosamine is present at a native N-glycosylation site of the antibody. In a further preferred embodiment, the antibody is IgG and said core N-acetylglucosamine is present at a native N-glycosylation site of the IgG. In a further preferred embodiment, the antibody is IgG, said core N-acetylglucosamine is present at a native N-glycosylation site of the IgG, and the native site is the N297 N-glycosylation site of IgG. The N297 N-glycosylation site is present in the Fc region of the heavy chain of an IgG antibody.

When said core N-acetylglucosamine is present at a native N-glycosylation site of an IgG antibody, it is preferred that the endoglycosidase is selected from the group consisting of Endo S, Endo S49 and Endo F, and a combination thereof. More preferably, the endoglycosidase is Endo S, Endo S49 or Endo F, even more preferably Endo S or Endo F, and most preferably Endo S. As is known in the art, Endo H, Endo M, Endo F1 are less suitable for the deglycosylation of a glycan that is present at the native site of an IgG antibody. In particular, they are less suitable for the deglycosylation of a glycan that is present at N297.

Modified Antibody

The invention also relates to an antibody obtainable by the process for the preparation of an modified antibody according to the invention. Said process for the preparation of a modified antibody, as well as preferred embodiments thereof, is described in detail above.

The invention further relates to an antibody comprising a GlcNAc-$S(A)_x$ substituent, wherein GlcNAc is an N-acetylglucosamine, wherein $S(A)_x$ is a sugar derivative comprising x functional groups A wherein A is independently selected from the group consisting of an azido group, a keto group and an alkynyl group and x is 1, 2, 3 or 4, wherein said GlcNAc-$S(A)_x$ substituent is bonded to the antibody via C1 of the N-acetylglucosamine of said GlcNAc-$S(A)_x$ substituent, and wherein said N-acetylglucosamine is optionally fucosylated. Such an antibody is herein referred to as a modified antibody.

In one embodiment the modified antibody according to the invention is of the Formula (4), wherein AB represents an antibody, GlcNAc is N-acetylglucosamine, Fuc is fucose, b is 0 or 1 and y is 1 to 20, and wherein S(A)$_x$ is a sugar derivative comprising x functional groups A wherein A is independently selected from the group consisting of an azido group, a keto group and an alkynyl group and x is 1, 2, 3 or 4. In a preferred embodiment, y is 1 to 10, more preferably y is 1, 2, 3, 4, 5, 6, 7 or 8, even more preferably y is 1, 2, 3 or 4 and most preferably y is 1 or 2.

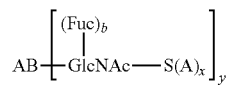

The sugar derivative S(A)$_x$ in the GlcNAc-S(A)$_x$ substituent of the modified antibody may for example be bonded to C4 of the GlcNAc via a β(1,4)-glycosidic bond or to C3 of said GlcNAc via an α(1,3)-glycosidic bond. The N-acetylglucosamine of said GlcNAc-S(A)$_x$ substituent is bonded via C1 to the antibody, preferably via an N-glycosidic bond to the amide nitrogen atom in the side chain of an asparagine amino acid of the antibody (GlcNAcβ1-Asn). The GlcNAc in said GlcNAc-S(A)$_x$ substituent is optionally fucosylated. Whether the sugar derivative S(A)$_x$ in the GlcNAc-S(A)$_x$ substituent of the modified antibody is bonded to C4 of the GlcNAc via a β(1,4)-glycosidic bond or to C3 of said GlcNAc via an α(1,3)-glycosidic bond depends on the catalyst that was used in the process for the preparation of the modified antibody. When the process is performed in the presence of a β(1,4)-galactosyltransferase catalyst then binding occurs via C1 of S(A)$_x$ and C4 of GlcNAc via a β(1,4)-glycosidic bond. When the process is performed in the presence of a α(1,3)-galactosyltransferase catalyst then binding occurs via C1 of S(A)$_x$ and C3 of GlcNAc via an α(1,3)-glycosidic bond.

When A is an azido functional group, the modified antibody is referred to as an azide-modified antibody. When A is a keto functional group, the modified antibody is referred to as a keto-modified antibody. When A is an alkynyl functional group, the modified antibody is referred to as an alkyne-modified antibody. Preferably, the modified antibody is an azide- or a keto-modified antibody, more preferably an azide-modified antibody.

In a preferred embodiment, said S(A)$_x$ is derived from a sugar or sugar derivative selected from the group consisting of galactose (Gal), mannose (Man), N-acetylglucosamine (GlcNAc), glucose (Glc), N-acetylgalactosamine (GalNAc), glucuronic acid (Gcu), fucose (Fuc) and N-acetylneuraminic acid (sialic acid), preferably Gal, GlcNAc, glucose and GalNAc.

In another preferred embodiment S(A)$_x$ is selected from the group consisting of GalNAz, 6-AzGal, 6-AzGalNAc, 4-AzGalNAz, 6-AzGalNAz, 6-AzGlc, 6-AzGlcNAz, 2-ketoGal, 2-N-propionylGalNAc and 2-(but-3-yonic acid amido)-2-deoxy-galactose. Most preferably, S(A)$_x$ is GalNAz or 4-AzGalNAc.

In another preferred embodiment, the modified-antibody according to the invention is an azide-modified antibody, i.e a functional group A in S(A)$_x$ is an azido group. An azide-modified antibody may have the structure shown below, wherein S(A)$_x$, with A is azido, is depicted as S[(Q)$_p$-N$_3$]$_x$:

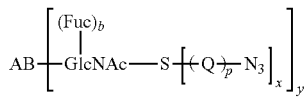

wherein:
b is 0 or 1;
x is 1, 2, 3 or 4;
S is a sugar derivative;
p is 0 or 1;
Q is —N(H)C(O)CH$_2$— or —CH$_2$—;
y is 1-20;
and wherein AB is an antibody, S is a sugar or a sugar derivative, GlcNAc is N-acetylglucosamine. GlcNAc is optionally fucosylated (b is 0 or 1).

The azide-modified antibody may comprise 1 to 20 optionally fucosylated substituents GlcNAc-S(A)$_x$ (y is 1 to 20). Preferably, y is 1 to 10, more preferably y is 1, 2, 3, 4, 5, 6, 7 or 8, even more preferably y is 1, 2, 3 or 4 and most preferably y is 1 or 2.

The value of p and the nature of Q depend on the azide-substituted sugar derivative S(A)$_x$ that is present in the azide-modified antibody. If an azido group in S(A)$_x$ is present on the C2, C3, or C4 position of the sugar or the sugar derivative, i.e. instead of the sugar-OH-group, then p is 0. If an azido group in S(A)$_x$ is a 2-azidoacetamido group, i.e. S(A)$_x$ is e.g. GalNAz or GlcNAz, then p is 1 and Q is —N(H)C(O)CH$_2$—. If an azido group in S(A)$_x$ is present on the C6 position of the sugar or the sugar derivative, i.e. instead of a sugar-OH-group or in case of 6-AzFuc instead of a H-atom, then p is 1 and Q is —CH$_2$—.

Preferably the modified antibody according to the invention is a monoclonal antibody, more preferably selected from the group consisting of IgA, IgD, IgE, IgG and IgM antibodies. Even more preferably said antibody is an IgG antibody, and most preferably said antibody is an IgG1 antibody. When the modified antibody is a whole antibody, the antibody preferably comprises two or more, more preferably two, GlcNAc-S(A)$_x$ substituents, said GlcNAc-S(A)$_x$ substituents being optionally fucosylated. However, if the modified antibody is an antibody fragment, e.g. a Fab or Fc fragment, the antibody may have only GlcNAc-S(A)$_x$ substituent, which is optionally fucosylated.

In the modified antibody according to the invention, the GlcNAc-S(A)$_x$ substituent may be situated anywhere on the antibody, provided that said substituent does not hinder the binding of an antigen the antigen-binding site of the antibody. In one embodiment, said GlcNAc-S(A)$_x$ substituent is situated in the Fc domain of the antibody, more preferably in the C$_H$2 domain. In another embodiment, said GlcNAc-S(A)$_x$ substituent is situated on the Fab domain of the antibody. In another embodiment, said GlcNAc-S(A)$_x$ substituent is situated on an antibody Fab or Fc fragment.

As was described above, the process for the preparation of the modified-antibody may provide modified antibodies comprising more than one GlcNAc-S(A)$_x$ substituent. The number of substituents on the antibodies depends not only on the nature of the antibody to be modified (e.g. whole antibody, single chain, fragment, etc.) but also on the number of core-GlcNAc substituents that is present on the antibody to be modified.

Process for the Preparation of an Antibody-Conjugate

The present invention also relates to the use of the modified antibody according to the invention in the preparation of an antibody-conjugate (AC). An antibody-conjugate (AC) is herein defined as an antibody that is conjugated to a molecule of interest (D) via a linker (L). The antibody-conjugate according to the invention may be conjugated to one or to more than one molecule of interest (D) via said linker (L).

A molecule of interest may for example be a reporter molecule, an active substance, an enzyme, a (non-catalytic)

protein, a peptide, an oligonucleotide, a glycan, an azide or a (hetero)cycloalkynyl moiety, preferably a bivalent or bifunctional (hetero)cycloalkynyl moiety. Further examples of a molecule of interest include a diagnostic compound, an amino acid (including an unnatural amino acid), a polypeptide, a (poly)ethylene glycol diamine (e.g. 1,8-diamino-3,6-dioxaoctane or equivalents comprising longer ethylene glycol chains), a polyethylene glycol chain, a polyethylene oxide chain, a polypropylene glycol chain, a polypropylene oxide chain and 1,x-diaminoalkane (wherein x is the number of carbon atoms in the alkane). In a preferred embodiment, the molecule of interest is selected from the group consisting of an amino acid (in particular lysine), an active substance, a reporter molecule, an azide and a (hetero)cycloalkynyl moiety. In a further preferred embodiment, the molecule of interest is selected from the group consisting of an active substance, a reporter molecule, an azide and a (hetero) cycloalkynyl moiety.

An active substance is a pharmacological and/or biological substance, i.e. a substance that is biologically and/or pharmaceutically active, for example a drug or a prodrug, a diagnostic agent, a protein, a peptide, an amino acid, a glycan, a lipid, a vitamin, a steroid, a nucleotide, a nucleoside, a polynucleotide, RNA or DNA. Examples of suitable peptide tags include a cell-penetrating peptides like human lactoferrin or polyarginine. An example of a suitable glycan is oligomannose.

In a preferred embodiment, the active substance is selected from the group consisting of drugs and prodrugs. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include camptothecins, staurosporin, doxorubicin, daunorubicin, colchicine, methotrexate, taxanes, calicheamycins, duocarmycins, maytansines and maytansinoids (i.e. maytansine derivatives), auristatins, tubulysin M, cryptophycin or pyrrolobenzodiazepines (PBDs). Examples of auristatins include dolastatin 10, auristatin F, monomethyl auristatin F (MMAF), auristatin E, monomethyl auristatin E (MMAE), auristatin PE, auristatin TP and auristatin AQ. Examples of maytansines and maytansinoids include mertansine and ansamitocin.

A reporter molecule is a molecule whose presence is readily detected, for example a diagnostic agent, a dye, a fluorophore, a radioactive isotope label, a contrast agent, a magnetic resonance imaging agent or a mass label. Examples of a fluorophore include all kinds of Alexa Fluor (e.g. Alexa Fluor 555), cyanine dyes (e.g. Cy3 or Cy5), coumarin derivatives, fluorescein, rhodamine, allophycocyanin and chromomycin.

Example of radioactive isotope label include $^{99m}$Tc, $^{111}$In, $^{18}$F, $^{14}$C, $^{64}$Cu, $^{131}$I or $^{123}$I, which may or may not be connected via a chelating moiety such as DTPA, DOTA, NOTA or HYNIC.

In the antibody-conjugate (AC) according to the invention, the molecule of interest is conjugated to the antibody via a linker (L). Linkers or linking units are well known in the art, and are described in more detail below.

The invention also relates to a process for the preparation of an antibody-conjugate, comprising reacting the modified antibody according to the invention with a linker-conjugate, wherein said linker-conjugate comprises a functional group B and one or more molecules of interest, wherein said functional group B is a functional group that is capable of reacting with a functional group A of a GlcNAc-S(A)$_x$ substituent on said modified antibody. Said linker-conjugate preferably is of the formula B-L(D)$_r$, wherein B, L and D are as defined above, and r is 1-20, preferably r is 1-10, more preferably r is 1-8, even more preferably r is 1, 2, 3, 4, 5 or 6, even more preferably r is 1, 2, 3 or 4 and most preferably r is 1 or 2.

Complementary functional groups B for the functional group A on the modified antibody (A is an azido group, a keto group or an alkynyl group) are known in the art.

When A is an azido group, linking of the azide-modified antibody and the linker-conjugate preferably takes place via a cycloaddition reaction. Functional group B is then preferably selected from the group consisting of alkynyl groups, preferably terminal alkynyl groups, and (hetero)cycloalkynyl groups.

When A is a keto group, linking of the keto-modified antibody with the linker-conjugate preferably takes place via selective conjugation with hydroxylamine derivatives or hydrazines, resulting in respectively oximes or hydrazones. Functional group B is then preferably a primary amino group, e.g. an —NH$_2$ group, an aminooxy group, e.g. —O—NH$_2$, or a hydrazinyl group, e.g. —N(H)NH$_2$. The linker-conjugate is then preferably H$_2$N-L(D)$_r$, H$_2$N—O-L (D)$_r$ or H$_2$N—N(H)-L(D)$_r$ respectively, wherein L, D and r are as defined above.

When A is an alkynyl group, linking of the alkyne-modified antibody with the linker-conjugate preferably takes place via a cycloaddition reaction, preferably a 1,3-dipolar cycoaddition. Functional group B is then preferably a 1,3-dipole, such as an azide, a nitrone or a nitrile oxide. The linker-conjugate is then preferably N$_3$-L(D)$_r$, wherein L, D and r are as defined above.

The invention thus also relates to a process for the preparation of an antibody-conjugate, comprising reacting the modified antibody according to the invention with a linker-conjugate, wherein:
a. when said modified antibody is an azide-modified antibody, said linker-conjugate comprises a (hetero) cycloalkynyl group or an alkynyl group, and one or more molecules of interest; or
b. when said modified antibody is a keto-modified antibody, said linker-conjugate comprises a primary amine group, an aminooxy group or a hydrazinyl group, and one or more molecules of interest; or
c. when said modified antibody is an alkyne-modified antibody, said linker-conjugate comprises an azido group, and one or more molecules of interest.

In a preferred embodiment, the present invention relates to a process for the preparation of an antibody-conjugate, comprising reacting an azide-modified antibody according to the invention with a linker-conjugate, wherein said linker-conjugate comprises a (hetero)cycloalkynyl group or a terminal alkynyl group, and one or more molecules of interest.

In said process, an azide on the azide-modified antibody according to the invention reacts with an alkynyl group, preferably a terminal alkynyl group, or a (heter)cycloalkynyl group of the linker-conjugate via a cycloaddition reaction. This cycloaddition reaction of a molecule comprising an azide with a molecule comprising a terminal alkynyl group or a (hetero)cycloalkynyl group is one of the reactions that is known in the art as "click chemistry". In the case of a linker-conjugate comprising a terminal alkynyl group, said cycloaddition reaction needs to be performed in the presence of a suitable catalyst, preferably a Cu(I) catalyst. However, in a preferred embodiment, the linker-conjugate comprises a (hetero)cycloalkynyl group, more preferably a strained (hetero)cycloalkynyl group. When the (hetero)cycloalkynyl is a strained (hetero)cycloalkynyl group, the presence of a catalyst is not necessary, and said reaction may even occur spontaneously by a reaction called strain-promoted azide-alkyne cycloaddition (SPAAC). This is one of the reactions known in the art as "metal-free click chemistry". Strained (hetero)cycloalkynyl groups are known in the art and are described in more detail below.

Therefore, in a preferred embodiment, the process for the preparation of an antibody-conjugate comprises reacting a modified antibody with a linker-conjugate, wherein said linker-conjugate comprises a (hetero)cycloalkynyl group and one or more molecules of interest, wherein said modified antibody is an antibody comprising a GlcNAc-S(A)$_x$ substituent, wherein GlcNAc is an N-acetylglucosamine, wherein S(A)$_x$ is a sugar derivative comprising x functional groups A wherein A is an azido group and x is 1, 2, 3 or 4, wherein said GlcNAc-S(A)$_x$ substituent is bonded to the antibody via C1 of the N-acetylglucosamine of said GlcNAc-S(A)$_x$ substituent, and wherein said GlcNAc is optionally fucosylated. In a further preferred embodiment, said (hetero)cycloalkynyl group is a strained (hetero)cycloalkynyl group.

In a further preferred embodiment, said process for the preparation of an antibody-conjugate comprises the steps of:
(i) contacting an antibody comprising a core N-acetylglucosamine (GlcNAc) substituent with a compound of the formula S(A)$_x$-P in the presence of a suitable catalyst, wherein said core N-acetylglucosamine substituent is optionally fucosylated, wherein said catalyst comprises a mutant catalytic domain from a galactosyltransferase, wherein S(A)$_x$ is a sugar derivative comprising x functional groups A wherein A is an azido group and x is 1, 2, 3 or 4, wherein P is selected from the group consisting of uridine diphosphate (UDP), guanosine diphosphate (GDP) and cytidine diphosphate (CDP),
to obtain a modified antibody, wherein a modified antibody is defined as an antibody comprising a GlcNAc-S(A)$_x$ substituent bonded to the antibody via C1 of the N-acetylglucosamine of said GlcNAc-S(A)$_x$ substituent, and wherein said modified antibody is according to Formula (4):

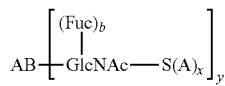

(4)

wherein:
S(A)$_x$ and x are as defined above; AB represents an antibody; GlcNAc is N-acetylglucosamine; Fuc is fucose; b is 0 or 1; and y is 1 to 20; and
(ii) reacting said modified antibody with a linker-conjugate, wherein said linker-conjugate comprises a (hetero)cycloalkynyl group and one or more molecules of interest.

Figure 31:
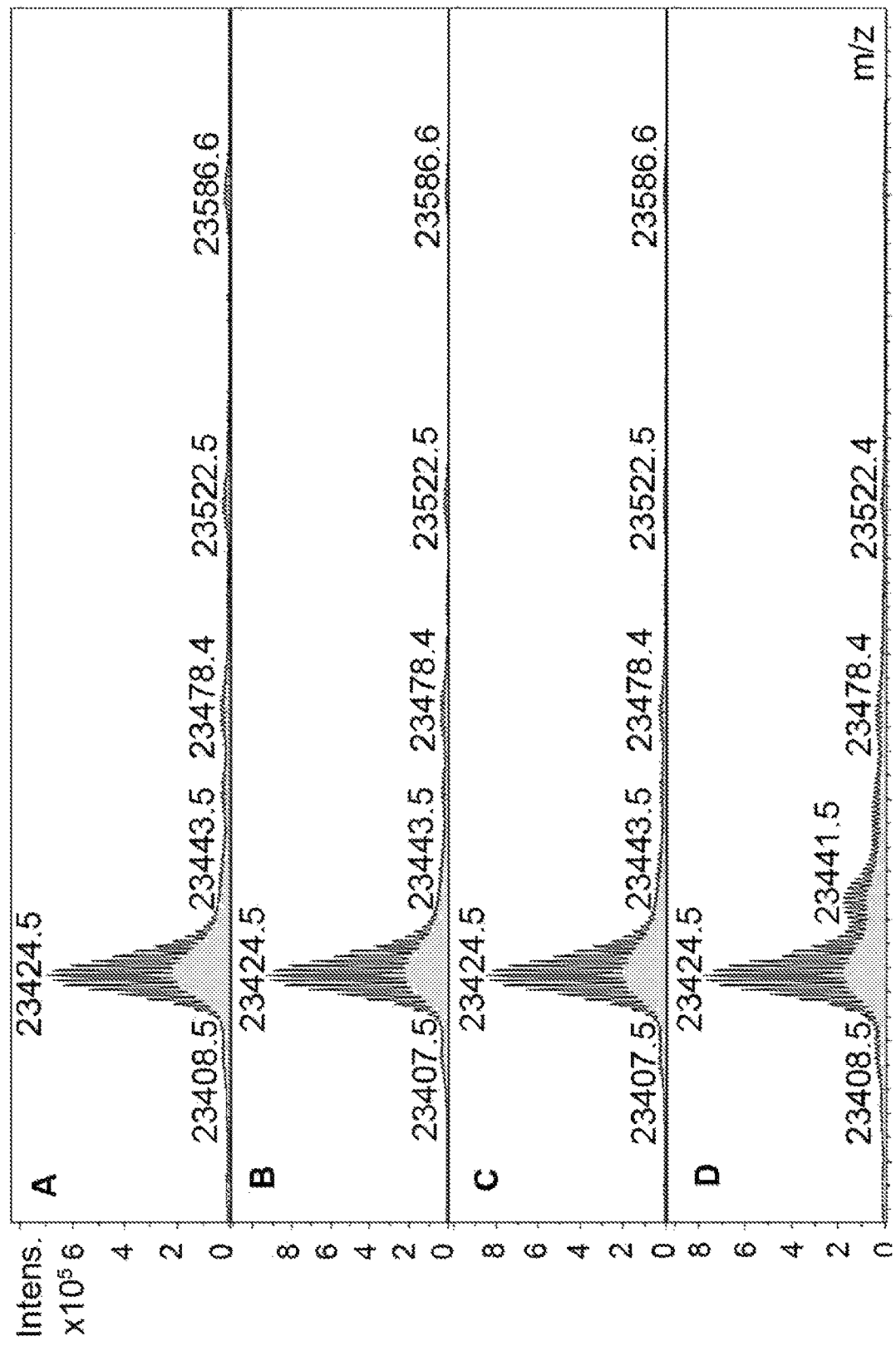
FIG. 31 shows the detailed mass spectral analysis of intact protein species (nanoLC-MS) using nanoLC coupled to ultra high resolution QTOF MS (maXis 4G) of the light chain (LC) of (A) native trastuzumab, (B) trast(GalNAz)$_2$, (C) trast(GalNAz)$_2$ after conjugation with BCN-biotin 25 and (D) trast(GalNAz)$_2$ after copper-catalyzed conjugation with alkyne-biotin 45. Whereas the base peak is identical for (A)-(C), trastuzumab conjugate formed under copper-catalysis (D) shows a clear shoulder at 23441.5 and another one at 23459.5, which indicates the formation of significant amounts (>20%) of oxidized and/or deamidated side-products.

An advantage of this embodiment of the process for the preparation of an antibody-conjugate according to the invention is that the presence of a copper catalyst is not necessary. Said process thus proceeds in the absence of a copper catalyst. The presence of a copper catalyst in said process has several disadvantages, however. Generally, the most convenient procedure for conjugation of azide to terminal alkynes requires the presence of Cu(I). Copper(I) is typically generated in situ from Cu(II), which requires the addition of a proper reducing agent, e.g. DTT, sodium ascorbate or hydrazine and the addition of a suitable ligand to maintain the copper in the Cu(I) oxidation state. However, extensive optimization and fine-tuning of conditions may be required to find the optimal parameters for efficient conversion. Nevertheless even under such conditions, the concomitant formation of reactive oxygen species cannot always be fully avoided, which in turn may induce oxidative damage to the protein, for example oxidation of methionine, histidine, cysteine or disulfide bonds. Other protocols have employed copper(I) sources such as CuBr for labeling fixed cells and synthesizing glycoproteins. In these cases, the instability of CuI in air imposes a requirement for large excesses of Cu (greater than 4 mm) and ligand for efficient reactions, which also raises concerns about protein damage or precipitation, plus the presence of residual metal after purification. It was found that the conjugation of azide-containing antibodies to terminal alkynes in the presence of copper leads to extensive side-product formation by undesired amino acid oxidation. For example, high-resolution mass spectral analysis of the trastuzumab light chain (LC) after copper-catalyzed conjugation indicates the formation of >20% of species with molecular weights+16/+18 (see FIG. 31). Detailed analysis of the trastuzumab heavy chain (HC) peptide fragments after tryptic digest indicates the oxidation of at least one particular histidine for as much as 69%, as exemplified in Example 39. Detailed analysis of the trastuzumab light chain (LC) peptide fragments after tryptic digest indicates the oxidation of at least one particular methionine, also exemplified in Example 39.

Molecules of interest are described in more detail above. In a preferred embodiment, the molecule of interest is selected from the group consisting of an active substance, a reporter molecule, an azide and a (hetero)cycloalkynyl group, more preferably an active substance, a reporter molecule and an azide. When the molecule of interest is a (hetero)cycloalkynyl group, it is preferred that said moiety is a (hetero)cyclooctyne moiety. Preferred structures of (hetero)cyclooctyne groups are described in more detail below.

The process for the preparation of a modified antibody according to the invention is preferably performed at a temperature in the range of about 20 to about 50° C., more preferably in the range of about 25 to about 45° C., even more preferably in the range of about 30 to about 40° C., and most preferably in the range of about 32 to about 37° C.

The process is preferably performed a pH in the range of about 5 to about 9, preferably in the range of about 5.5 to about 8.5, more preferably in the range of about 6 to about 8. Most preferably, the process is performed at a pH in the range of about 7 to about 8.

The process is preferably performed in water. More preferably, said water is purified water, even more preferably ultrapure water or Type I water as defined according to ISO 3696. Suitable water is for example milliQ® water. Said water is preferably buffered, for example with phosphate-buffered saline or tris. Suitable buffers are known to a person skilled in the art. In a preferred embodiment, the process is performed in milliQ water which is buffered with phosphate-buffered saline or tris.

Preferably, the linker-conjugate comprises a (hetero)cycloalkynyl group. In a preferred embodiment said linker-conjugate has the Formula (11):

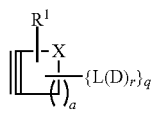

wherein:
L is a linker;
D is a molecule of interest;
r is 1-20;
$R^1$ is independently selected from the group consisting of hydrogen, halogen, $-OR^5$, $-NO_2$, $-CN$, $-S(O)_2R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
X is $C(R^1)_2$, O, S or $NR^2$, wherein $R^2$ is $R^1$ or $L(D)_r$, and wherein L, D and r are as defined above;
q is 0 or 1, with the proviso that if q is 0 then X is $N-L(D)_r$; and
a is 0, 1, 2, 3, 4, 5, 6, 7 or 8.

In another preferred embodiment said linker-conjugate has the Formula (11b):

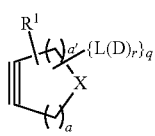

wherein:
L is a linker;
D is a molecule of interest;
r is 1-20;
$R^1$ is independently selected from the group consisting of hydrogen, halogen, $-OR^5$, $-NO_2$, $-CN$, $-S(O)_2R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
X is $C(R')_2$, O, S or $NR^2$, wherein $R^2$ is $R^1$ or $L(D)_r$, and wherein L, D and r are as defined above;
q is 0 or 1, with the proviso that if q is 0 then X is $N-L(D)_r$;
a is 0, 1, 2, 3, 4, 5, 6, 7 or 8;
a' is 0, 1, 2, 3, 4, 5, 6, 7 or 8; and
a+a'<10.
In a further preferred embodiment, a+a' is 4, 5, 6 or 7, more preferably a+a' is 4, 5 or 6 and most preferably a+a' is 5.

In a preferred embodiment, if q is 1 then X is $C(R^1)_2$, O, S or $NR^1$.

In another preferred embodiment, a is 5, i.e. said (hetero)cycloalkynyl group is preferably a (hetero)cyclooctyne group. In another preferred embodiment, X is $C(R^2)_2$ or $NR^2$. When X is $C(R^2)_2$ it is preferred that $R^2$ is hydrogen When X is $NR^2$, it is preferred that $R^2$ is $L(D)_r$. In yet another preferred embodiment, r is 1 to 10, more preferably, r is 1, 2, 3, 4, 5, 6 7 or 8, more preferably r is 1, 2, 3, 4, 5 or 6, most preferably r is 1, 2, 3 or 4.

The $L(D)_r$ substituent may be present on a C-atom in said (hetero)cycloalkynyl group, or, in case of a heterocycloalkynyl group, on the heteroatom of said heterocycloalkynyl group. When the (hetero)cycloalkynyl group comprises substituents, e.g. an annelated cycloalkyl, the $L(D)_r$ substituent may also be present on said substituents.

The methods to connect a linker L to a (hetero)cycloalkynyl group on the one end and to a molecule of interest on the other end, in order to obtain a linker-conjugate, depend on the exact the nature of the linker, the (hetero)cycloalkynyl group and the molecule of interest. Suitable methods are known in the art.

Preferably, the linker-conjugate comprises a (hetero)cyclooctyne group, more preferably a strained (hetero)cyclooctyne group. Suitable (hetero)cycloalkynyl moieties are known in the art. For example DIFO, DIFO2 and DIFO 3 are disclosed in US 2009/0068738, incorporated by reference. DIBO is disclosed in WO 2009/067663, incorporated by reference. DIBO may optionally be sulfated (S-DIBO) as disclosed in *J. Am. Chem. Soc.* 2012, 134, 5381. BARAC is disclosed in *J. Am. Chem. Soc.* 2010, 132, 3688-3690 and US 2011/0207147, all incorporated by reference.

Preferred examples of linker-conjugates comprising a (hetero)cyclooctyne group are shown below.

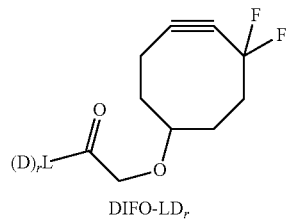

DIFO-$LD_r$ (12)

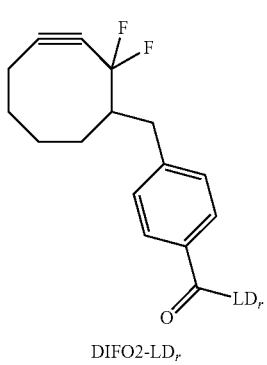

DIFO2-$LD_r$ (13)

-continued

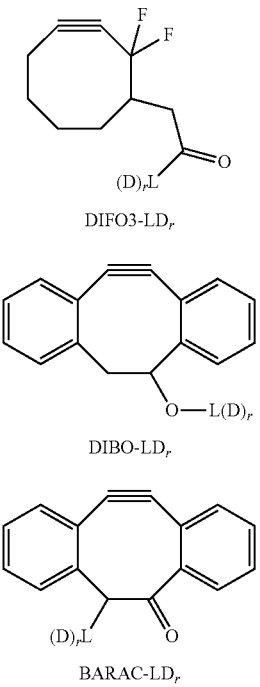

DIFO3-L(D)$_r$ (14)

DIBO-L(D)$_r$ (15)

BARAC-L(D)$_r$ (16)

Other cyclooctyne moieties that are known in the art are DIBAC (also known as ADIBO or DBCO) and BCN. DIBAC is disclosed in *Chem. Commun.* 2010, 46, 97-99, incorporated by reference. BCN is disclosed in WO 2011/136645, incorporated by reference.

In a preferred embodiment, said linker-conjugate has the Formula (12), (13), (14), (15) or (16).

In another preferred embodiment, said linker-conjugate has the Formula (17):

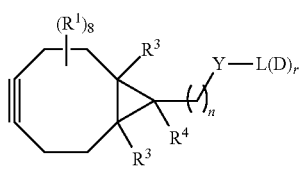

17 wherein:
R$^1$, L, D and r are as defined above;
Y is O, S or NR$^2$, wherein R$^2$ is as defined above;
R$^3$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups;
R$^4$ is selected from the group consisting of hydrogen, Y-L(D)$_r$, —(CH$_2$)$_n$—Y-L(D)$_r$, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted; and
n is 1, 2, 3, 4, 5, 6, 7, 8, 9 or 10.

In a further preferred embodiment, R$^1$ is hydrogen. In another preferred embodiment, R$^3$ is hydrogen. In another preferred embodiment, n is 1 or 2. In another preferred embodiment, R$^4$ is hydrogen, Y-L(D)$_r$ or —(CH$_2$)$_n$—Y-L(D)$_r$. In another preferred embodiment, R$^2$ is hydrogen or L(D)$_r$. In a further preferred embodiment, the linker-conjugate has the Formula 18:

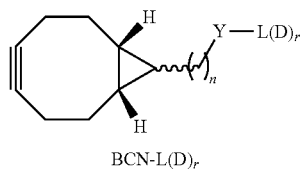

BCN-L(D)$_r$ 18 wherein Y, L, D, n and r are as defined above.

In another preferred embodiment, said linker-conjugate has the Formula (19):

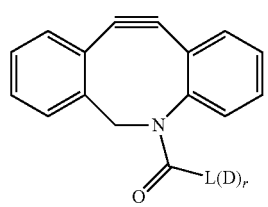

19 wherein L, D and r are as defined above.

In another preferred embodiment, said linker-conjugate has the Formula (15):

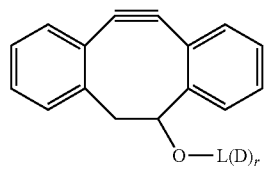

15 wherein L, D and r are as defined above.

The cycloaddition reaction of an azide-modified antibody according to the invention with a linker-conjugate comprising a preferred type of cyclooctyne group BCN-L(D)$_r$ (17) is shown in Scheme 2.

Scheme 2

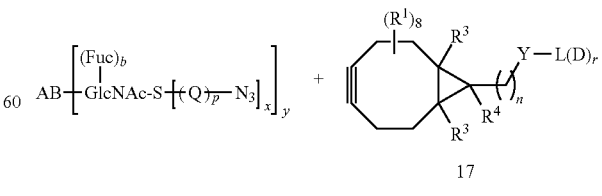

↓

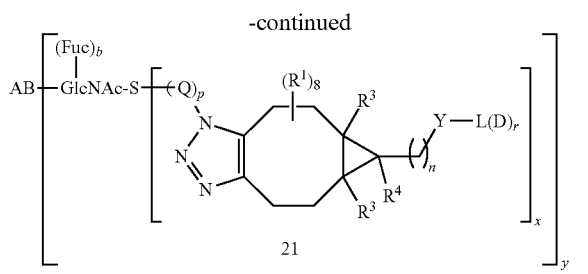

wherein R¹, R³, R⁴, S, Q, Y, L, D, b, p, x, n are as defined above, and y is 1-20.

The value of p and the nature of Q depend on the azide-substituted sugar or sugar derivative $S(A)_x$ that is present in the azide-modified antibody according to the invention that is linked to a linker-conjugate. If an azide in $S(A)_x$ is present on the C2, C3, or C4 position of the sugar or the sugar derivative (instead of a sugar OH-group), then p is 0. If the $S(A)_x$ is an azidoacetamido-sugar derivative, $S(A)_x$ is e.g. GalNAz or GlcNAz, then p is 1 and Q is —N(H)C(O)CH₂—. If the azide in $S(A)_x$ is present on the C6 position of the sugar or the sugar derivative, then p is 1 and Q is —CH₂—.

Linkers (L), also referred to as linking units, are well known in the art. In a linker-conjugate as described herein, L is linked to a molecule of interest as well as to a functional group B, as was described above.

In a preferred embodiment, the modified antibody according to the invention is an azide-modified antibody. A suitable linker-conjugate for the preparation of an azide-modified antibody is a linker-conjugate comprising a (hetero)cycloalkynyl group and a molecule of interest. Numerous methods for linking said (hetero)cycloalkynyl group and said molecule of interest to L are known in the art. As will be clear to a person skilled in the art, the choice of a suitable method for linking a (hetero)cycloalkynyl group to one end of a linker and a molecule of interest to another end depends on the exact nature of the (hetero)cycloalkynyl group, the linker and the molecule of interest.

A linker may have the general structure $F^1$-L($F^2$)$_r$, wherein $F^1$ represents a functional group that is able to react with a functional group F on the functional group B as described above, e.g. a (hetero)cycloalkynyl group, a terminal alkynyl group, a primary amine, an aminooxy group, a hydrazyl group or an azido group. $F^2$ represents a functional group that is able to react with a functional group F on the molecule of interest.

Since more than one molecule of interest may be bonded to a linker, more than one functional group $F^2$ may be present on L. As was described above, r is 1 to 20, preferably 1 to 10, more preferably 1 to 8, even more preferably 1, 2, 3, 4, 5 or 6, even more preferably 1, 2, 3 or 4 and most preferably, r is 1 or 2.

L may for example be selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, S and $NR^5$, wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups. Most preferably, the heteroatom is O.

F, $F^1$ and $F^2$ may for example be independently selected from the group consisting of hydrogen, halogen, $R^5$, $C_4$-$C_{10}$ (hetero)cycloalkyne groups, —CH=C($R^5$)₂, —C≡C$R^5$, —[C($R^5$)₂C($R^5$)₂O]$_q$—$R^5$, wherein q is in the range of 1 to 200, —CN, —N₃, —NCX, —XCN, —X$R^5$, —N($R^5$)₂, —⁺N($R^5$)₃, —C(X)N($R^5$)₂, —C($R^5$)₂X$R^5$, —C(X)$R^5$, —C(X)X$R^5$, —S(O)$R^5$, —S(O)₂$R^5$, —S(O)O$R^5$, —S(O)₂O$R^5$, —S(O)N($R^5$)₂, —S(O)₂N($R^5$)₂, —OS(O)$R^5$, —OS(O)₂$R^5$, —OS(O)O$R^5$, —OS(O)₂O$R^5$, —P(O)($R^5$)(O$R^5$), —P(O)(O$R^5$)₂, —OP(O)(O$R^5$)₂, —Si($R^5$)₃, —XC(X)$R^5$, —XC(X)X$R^5$, —XC(X)N($R^5$)₂, —N($R^5$)C(X)$R^5$, —N($R^5$)C(X)X$R^5$ and —N($R^5$)C(X)N($R^5$)₂, wherein X is oxygen or sulphur and wherein $R^5$ is as defined above.

Examples of suitable linking units include (poly)ethylene glycol diamines (e.g. 1,8-diamino-3,6-dioxaoctane or equivalents comprising longer ethylene glycol chains), polyethylene glycol or polyethylene oxide chains, polypropylene glycol or polypropylene oxide chains and 1,x-diaminoalkanes wherein x is the number of carbon atoms in the alkane.

Another class of suitable linkers comprises cleavable linkers. Cleavable linkers are well known in the art. For example Shabat et al., *Soft Matter* 2012, 6, 1073, incorporated by reference herein, discloses cleavable linkers comprising self-immolative moieties that are released upon a biological trigger, e.g. an enzymatic cleavage or an oxidation event. Some examples of suitable cleavable linkers are peptide-linkers that are cleaved upon specific recognition by a protease, e.g. cathepsin, plasmin or metalloproteases, or glycoside-based linkers that are cleaved upon specific recognition by a glycosidase, e.g. glucoronidase, or nitroaromatics that are reduced in oxygen-poor, hypoxic areas.

Antibody-Conjugate

The invention also relates to an antibody-conjugate obtainable by the process for the preparation of an antibody-conjugate according to the invention. Said process for the preparation of an antibody-conjugate and the preferred embodiments of said process are described in detail above.

The invention therefore also relates to an antibody-conjugate, obtainable by a process comprising the steps of:

(i) contacting an antibody comprising a core N-acetylglucosamine (GlcNAc) substituent with a compound of the formula $S(A)_x$-P in the presence of a suitable catalyst, wherein said core N-acetylglucosamine substituent is optionally fucosylated, wherein said catalyst comprises a mutant catalytic domain from a galactosyltransferase, wherein $S(A)_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP), to obtain a modified antibody, wherein a modified antibody is defined as an antibody comprising a GlcNAc-$S(A)_x$ substituent bonded to the antibody via C1 of the N-acetylglucosamine of said GlcNAc-$S(A)_x$ substituent, and wherein said modified antibody is according to Formula (4):

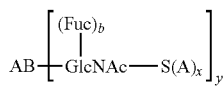

wherein:
S(A)$_x$ and x are as defined above; AB represents an antibody; GlcNAc is N-acetylglucosamine; Fuc is fucose; b is 0 or 1; and y is 1 to 20; and (ii) reacting said modified antibody with a linker-conjugate, wherein:
(a) when said modified antibody is an azide-modified antibody, said linker-conjugate comprises a (hetero) cycloalkynyl group or an alkynyl group, and one or more molecules of interest; or
(b) when said modified antibody is a keto-modified antibody, said linker-conjugate comprises a primary amine group, an aminooxy group or a hydrazinyl group, and one or more molecules of interest; or
(c) when said modified antibody is an alkyne-modified antibody, said linker-conjugate comprises an azido group, and one or more molecules of interest;
wherein a molecule of interest (D) is conjugated to the antibody via a linker (L), and wherein D and L are as defined above.

The invention further relates to an antibody-conjugate according to the Formula (20):

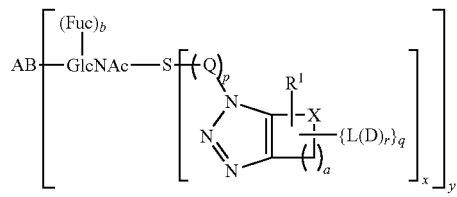

wherein AB is an antibody, S is a sugar or a sugar derivative, GlcNAc is N-acetylglucosamine, wherein y is 1-20, and wherein L, D, X, R$^1$, Q, a, b, p, r, x, y and q are as defined above, as well as their preferred embodiments.

The invention further relates to an antibody-conjugate according to the Formula (20b):

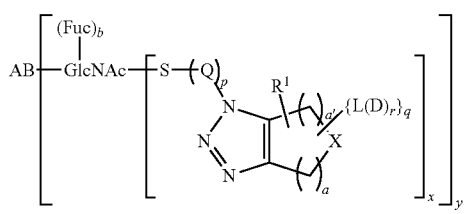

wherein AB is an antibody, S is a sugar or a sugar derivative, GlcNAc is N-acetylglucosamine, wherein y is 1-20, and wherein L, D, X, R$^1$, Q, a, a', b, p, r, x, y and q are as defined above, as well as their preferred embodiments.

In the conjugated antibody of the Formula (20) and (20b), GlcNAc is optionally fucosylated (b is 0 or 1). The antibody may comprise up to 20 conjugated substituents (y is 1-20). Preferably y is 1-10, more preferably y is 1, 2, 3, 4, 5, 6, 7 or 8, even more preferably y is 1, 2, 3 or 4 and most preferably y is 1 or 2.

Preferred structures of the sugar derivative (S), the linker (L), substituent R$^1$ and preferred values for r and a are described in detail above.

As was described above, the value of p and the nature of Q depend on the azide-substituted sugar or sugar derivative S(A)$_x$ that is present in the azide-modified antibody according to the invention that is linked to a linker-conjugate. If the azide in S(A)$_x$ is present on the C2, C3, or C4 position of the sugar derivative, then p is 0. If the S(A) is an azidoacetamido-sugar derivative, S(A)$_x$ is e.g. GalNAz or GlcNAz, then p is 1 and Q is —N(H)C(O)CH$_2$—. If the azide in S(A)$_x$ is present on the C6 position of the sugar or the sugar derivative, then p is 1 and Q is —CH$_2$—.

Molecules of interest (D) are also described in more detail above. The antibody-conjugate may comprise more than one molecule of interest. An antibody-conjugate comprises more than one molecule of interest for example when it is linked to more than one linker-conjugate, when one linker-conjugate comprises more than one molecule of interest, or both.

Preferably the molecule of interest is selected from the groups consisting of an active substance, a reporter molecule, an azide and a (hetero)cycloalkyne group. When the molecule of interest is an active substance, the antibody-conjugate may also be referred to as an antibody drug conjugate (ADC).

In a preferred embodiment, the antibody-conjugate according to the invention is of the Formula (21):

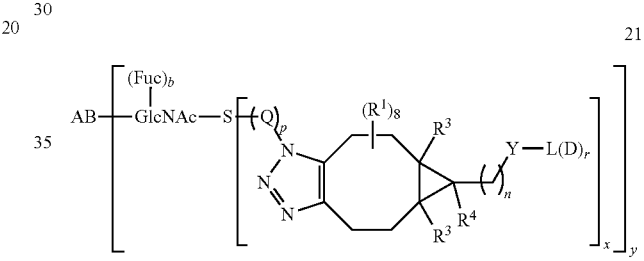

wherein AB, L, D, Y, S, Q, x, y, b, p, R$^2$, GlcNAc, R$^1$ R$^3$, R$^4$, n and r are as defined above and wherein said N-acetylglucosamine is optionally fucosylated (b is 0 or 1).

In a further preferred embodiment, R$^1$, R$^3$ and R$^4$ are hydrogen and n is 1 or 2, and in an even more preferred embodiment x is 1.

In another preferred embodiment, the antibody-conjugate is of the Formula (22):

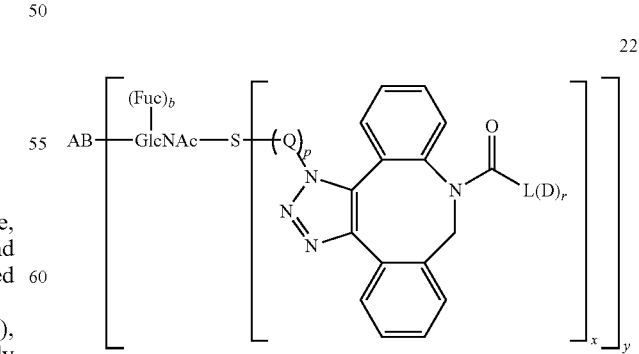

wherein AB, L, D, X, S, b, p, x, y, Q and GlcNAc are as defined above, and wherein said N-acetylglucosamine is optionally fucosylated (b is 0 or 1).

Antibody-conjugate 22 is an example of a compound that may exist in several regioisomers. Another regioisomer is shown below.

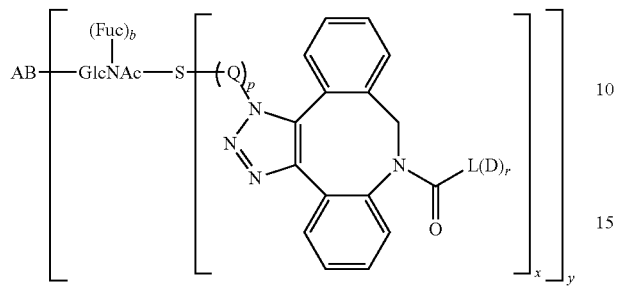

wherein AB, L, D, X, S, b, p, x, y, Q and GlcNAc are as defined above, and wherein said N-acetylglucosamine is optionally fucosylated.

In another preferred embodiment, the antibody-conjugate is of the Formula (15b):

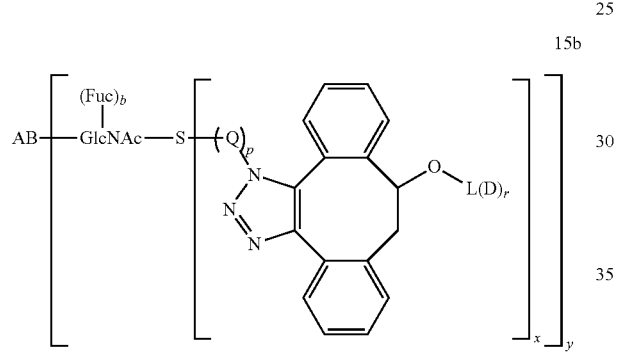

wherein AB, L, D, X, S, b, p, x, y, Q and GlcNAc are as defined above, and wherein said N-acetylglucosamine is optionally fucosylated.

Figure 6:
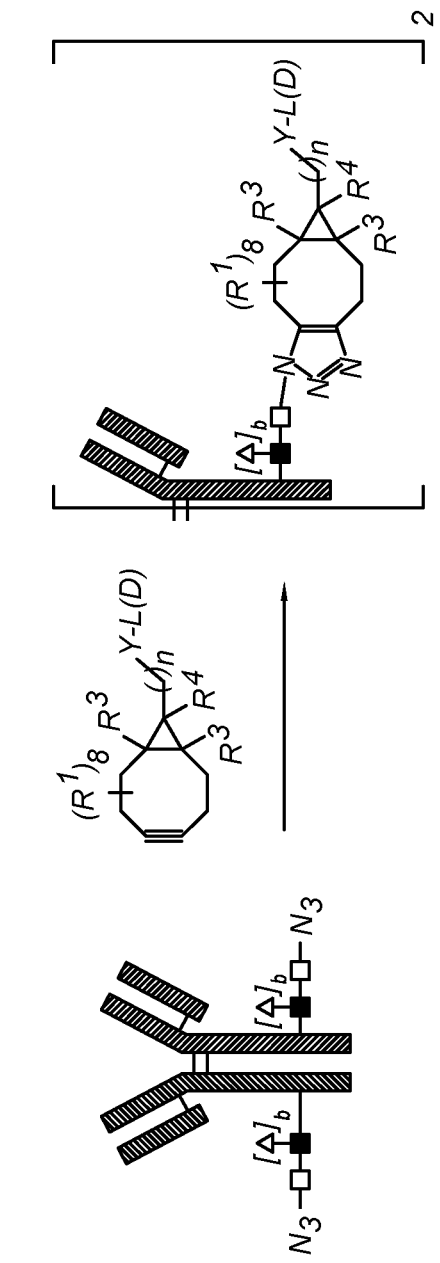
FIG. 6 shows a preferred embodiment of the process for the preparation of an antibody-conjugate, wherein an azide-modified antibody is conjugated to a linker-conjugate comprising one or more molecules of interest.

In FIG. 6, another preferred embodiment of the antibody-conjugate according to the invention is shown. An antibody comprising two heavy chains and two light chains comprises an optionally fucosylated core-GlcNAc on each heavy chain. A linker-conjugate according to the Formula (17) is connected to the antibody via a cycloaddition reaction of the cyclooctynyl group of said linker-conjugate with an azide on the azide-modified antibody according to the invention having a -GlcNAc-GalNAz substituent.

The invention further relates to the antibody-conjugate according to the invention, for use as a medicament. Preferred embodiments of said antibody-conjugate are described in more detail above.

Antibody-Drug Conjugate

When the molecule of interest in an antibody-conjugate according to the invention is an active substance, the antibody-conjugate may also be referred to as an antibody drug conjugate (ADC). The present invention thus also relates to an antibody-drug conjugate, wherein a molecule of interest (D) is conjugated to the antibody via a linker (L); wherein said molecule of interest (D) is an active substance; and wherein an active substance is defined as a substance that is biologically and/or pharmaceutically active.

The invention also relates to an antibody-conjugate obtainable by the process for the preparation of an antibody-conjugate according to the invention, wherein a molecule of interest (D) is conjugated to the antibody via a linker (L); wherein said molecule of interest (D) is an active substance; and wherein an active substance is defined as a substance that is biologically and/or pharmaceutically active. Said process for the preparation of an antibody-conjugate and the preferred embodiments of said process are described in detail above.

In a preferred embodiment, the invention relates to an antibody-conjugate, obtainable by a process comprising the steps of:
(i) contacting an antibody comprising a core N-acetylglucosamine (GlcNAc) substituent with a compound of the formula $S(A)_x$-P in the presence of a suitable catalyst, wherein said core N-acetylglucosamine substituent is optionally fucosylated, wherein said catalyst comprises a mutant catalytic domain from a galactosyltransferase, wherein $S(A)_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP),
to obtain a modified antibody, wherein a modified antibody is defined as an antibody comprising a GlcNAc-$S(A)_x$ substituent bonded to the antibody via C1 of the N-acetylglucosamine of said GlcNAc-$S(A)_x$ substituent, and wherein said modified antibody is according to Formula (4):

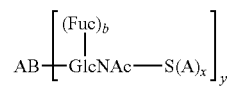

wherein:
$S(A)_x$ and x are as defined above; AB represents an antibody; GlcNAc is N-acetylglucosamine; Fuc is fucose; b is 0 or 1; and y is 1 to 20; and
(ii) reacting said modified antibody with a linker-conjugate, wherein:
(a) when said modified antibody is an azide-modified antibody, said linker-conjugate comprises a (hetero)cycloalkynyl group or an alkynyl group, and one or more molecules of interest; or
(b) when said modified antibody is a keto-modified antibody, said linker-conjugate comprises a primary amine group, an aminooxy group or a hydrazinyl group, and one or more molecules of interest; or
(c) when said modified antibody is an alkyne-modified antibody, said linker-conjugate comprises an azido group, and one or more molecules of interest;
wherein a molecule of interest (D) is conjugated to the antibody via a linker (L); wherein said molecule of interest (D) is an active substance; and wherein an active substance is defined as a substance that is biologically and/or pharmaceutically active.

Molecules of interest (D) and linkers (L) are described in more detail above and below.

Step (i) and step (ii) of the process whereby the antibody-drug conjugate is obtainable, as well as preferred embodiments thereof, are described in detail above.

The antibody-drug conjugate is preferably obtainable by the process according to the invention, wherein x is 1 or 2, and more preferably, x is 1. As a consequence, in the modified antibody according to Formula (4) as well as in the antibody-drug conjugate each sugar moiety S is preferably linked to 1 or 2, more preferably 1, linker conjugates $L(D)_r$.

The antibody-drug conjugate is preferably obtainable by the process according to the invention, wherein y is 1, 2, 3, 4, 5, 6, 7 or 8, more preferably y is 1, 2, 3 or 4 and even more preferably, y is 1 or 2. It is further preferred that r is 1, 2, 3 or 4, more preferably r is 1 or 2 and most preferably r is 1.

It is further preferred that in the antibody-drug conjugate according to the invention the antibody is a whole antibody, wherein y is 2. In this embodiment, the antibody-drug conjugate may thus be linked to 2, 4 or 8 molecules of interest, more preferably the antibody is linked to 2 or 4 molecules of interest and most preferably the antibody is linked to 2 molecules of interest.

In a further preferred embodiment, the antibody is selected from the group consisting of IgA, IgD, IgE, IgG and IgM antibodies, more preferably the antibody is an IgG antibody, preferably an IgG1 antibody.

In another embodiment of the antibody-drug conjugate according to the invention, the antibody is an antibody fragment. In this embodiment, it is preferred that y is 1.

In a further preferred embodiment, x is 1 and y is 1. In another further preferred embodiment, x is 2 and y is 2. It is further preferred that r is 1. In another further preferred embodiment, x is 1, y is 1 and r is 1. In another further preferred embodiment, x is 1, y is 2 and r is 1. In another further preferred embodiment, x is 2, y is 2 and r is 1.

In a preferred embodiment the antibody-drug conjugate is obtainable by the process according to the invention, wherein in step (ii) said modified antibody is an azide-modified antibody, and wherein said linker-conjugate has the Formula (11) or (11b):

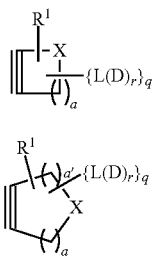

11

11b wherein:
D and L are as defined above;
r is 1-20;
$R^1$ is independently selected from the group consisting of hydrogen, halogen, —$OR^5$, —$NO_2$, —CN, —$S(O)_2R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
X is $C(R^1)_2$, O, S or $NR^2$, wherein $R^2$ is $R^1$ or $L(D)_r$ wherein L, D and r are as defined above;

q is 0 or 1, with the proviso that if q is 0 then X is $N$-$L(D)_r$;
a is 0, 1, 2, 3, 4, 5, 6, 7 or 8;
a' is 0, 1, 2, 3, 4, 5, 6, 7 or 8; and
a+a'<10.
Preferably, a+a' is 4, 5, 6 or 7, more preferably a+a' is 4, 5 or 6 and most preferably a+a' is 5.

In a further preferred embodiment, the antibody-drug conjugate according to the invention is obtainable by the process according to the invention, wherein in step (ii) said modified antibody is an azide-modified antibody and wherein said linker-conjugate has the Formula (12), (13), (14), (15) or (16).

In another further preferred embodiment, the antibody-drug conjugate according to the invention is obtainable by the process according to the invention, wherein in step (ii) said modified antibody is an azide-modified antibody and wherein said linker-conjugate has the Formula (17):

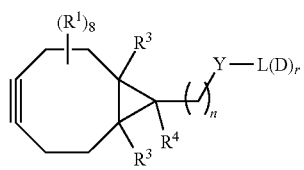

17 wherein:
$R^1$, L, D and r are as defined above;
Y is O, S or $NR^2$, wherein $R^2$ is as defined above;
$R^3$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
$R^4$ is selected from the group consisting of hydrogen, $Y$-$L(D)_r$, —$(CH_2)_n$—$Y$-$L(D)_r$, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted; and
n is 1, 2, 3, 4, 5, 6, 7, 8, 9 or 10.

In another further preferred embodiment, $R^1$ is hydrogen. In another preferred embodiment, $R^3$ is hydrogen. In another preferred embodiment, n is 1 or 2. In another preferred embodiment, $R^4$ is hydrogen, $Y$-$L(D)_r$ or —$(CH_2)_n$—$Y$-$L(D)_r$. In another preferred embodiment, $R^2$ is hydrogen or $L(D)_r$. In a further preferred embodiment, the linker-conjugate has the Formula 18:

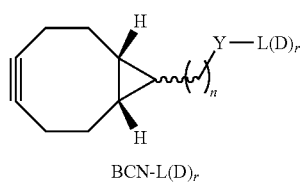

18

BCN-$L(D)_r$ wherein Y, L, D, n and r are as defined above.

In another further preferred embodiment, the antibody-drug conjugate according to the invention is obtainable by the process according to the invention, wherein in step (ii)

said modified antibody is an azide-modified antibody and wherein said linker-conjugate has the Formula (19):

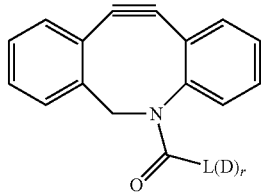

(19)

wherein L, D and r are as defined above.

In another further preferred embodiment, the antibody-drug conjugate according to the invention is obtainable by the process according to the invention, wherein in step (ii) said modified antibody is an azide-modified antibody and wherein said linker-conjugate has the Formula (15):

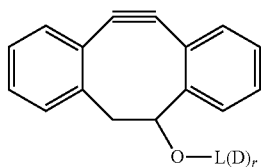

(15)

wherein L, D and r are as defined above.

In vivo efficacy experiments show that the antibody-drug conjugate according to the invention has an effect on tumor volume.

The invention further relates to an antibody-drug conjugate according to the invention, wherein the molecule of interest is an active substance, for use as a medicament.

The invention also relates to the use of an antibody-drug conjugate according to the invention, wherein the molecule of interest is an active substance, for use in the treatment of cancer.

The invention further relates to an antibody-drug conjugate according to the invention, wherein the molecule of interest is an active substance, for use in the treatment of breast cancer, more preferably for use in the treatment of HER2-positive breast cancer.

The invention also relates to a method treating cancer by administering an antibody-drug conjugate according to the invention.

The invention also relates to a method treating breast cancer by administering an antibody-drug conjugate according to the invention.

The invention also relates to a method treating HER2-positive breast cancer by administering an antibody-drug conjugate according to the invention.

In a preferred embodiment, the antibody in said antibody-drug conjugate is trastuzumab. In a further preferred embodiment, the molecule of interest is a cytotoxin, preferably maytansinoid, auristatin E, auristatin F, duocarmycin or pyrrolobenzodiazepine.

In the antibody-drug conjugate according to the invention, the molecule of interest is an active substance. As was described above, an active substance is a pharmacological and/or biological substance, i.e. a substance that is biologically and/or pharmaceutically active, for example a drug or a prodrug, a diagnostic agent, a protein, a peptide, an amino acid, a glycan, a lipid, a vitamin, a steroid, a polyethyleneglycol, a nucleotide, a nucleoside, a polynucleotide, RNA or DNA. Examples of suitable peptide tags include cell-penetrating peptides like human lactoferrin or polyarginine. An example of a suitable glycan is oligomannose.

In a preferred embodiment, the active substance is selected from the group consisting of drugs and prodrugs. More preferably, the active substance is selected from the group consisting of pharmaceutically active compounds, in particular low to medium molecular weight compounds (e.g. about 200 to about 1500 Da, preferably about 300 to about 1000 Da), such as for example cytotoxins, antiviral agents, antibacterials agents, peptides and oligonucleotides. Examples of cytotoxins include camptothecins, staurosporin, doxorubicin, daunorubicin, colchicine, methotrexate, taxanes, calicheamycins, duocarmycins, maytansines and maytansinoids (i.e. maytansine derivatives), auristatins, tubulysin M, cryptophycin or pyrrolobenzodiazepines (PBDs). Examples of auristatins include dolastatin 10, auristatin F, monomethyl auristatin F (MMAF), auristatin E, monomethyl auristatin E (MMAE), auristatin PE, auristatin TP and auristatin AQ. Examples of maytansines and maytansinoids include mertansine and ansamitocin.

In a preferred embodiment, the antibody in said antibody-conjugate is an antibody specifically binding cancer antigen. Examples of an antibody specifically binding cancer antigen include trastuzumab, pertuzumab, cetuximab, rituximab, bevacizumab, girentuximab, gemtuzumab, inotuzumab, alemtuzumab, tositumumab, ipilimumab, ofatumumab, panitumumab, elotuzumab, zanolimumab, obinutuzumab, necitumumab, farletuzumab, vedolizumab, tabalumab, itolizumab, ocrelizumab, epratuzumab, mepolizumab, reslizumab, sarilumab and ramicurumab.

Therefore, the invention relates to an antibody-drug conjugate according to the invention, wherein the antibody is an antibody specifically binding cancer antigen and wherein the molecule of interest is a cytotoxin, for use as a medicament. The invention also relates to an antibody-drug conjugate according to the invention, wherein the antibody is an antibody specifically binding cancer antigen and wherein the molecule of interest is a cytotoxin, for use in the treatment of cancer. Also, the invention relates to an antibody-conjugate according to the invention, wherein the antibody is an antibody specifically binding cancer antigen and wherein the molecule of interest is a cytotoxin, for use in the treatment of breast cancer, and more preferably for use in the treatment of HER2 positive breast cancer.

In a further preferred embodiment, the invention relates to an antibody-conjugate according to the invention, wherein the antibody-conjugate is trastuzumab-(MMAF)$_2$, trastuzumab-(vc-PABA-MMAF)$_2$, trastuzumab(maytansinoid)$_2$ or trastuzumab-(vc-PABA-maytansinoid)$_2$, for use in the treatment of cancer. In a further preferred embodiment, the invention relates to an antibody-conjugate according to the invention, wherein the antibody-conjugate is trastuzumab-(MMAF)$_2$, trastuzumab-(vc-PABA-MMAF)$_2$, trastuzumab(maytansinoid)$_2$ or trastuzumab-(vc-PABA-maytansinoid)$_2$, for use in the treatment of breast cancer, more preferably for use in the treatment of HER2 positive breast cancer.

In addition, the invention relates to a method for treating cancer by administering an antibody-drug conjugate according to the invention. The invention also relates to a method of treating breast cancer by administering an antibody-drug conjugate according to the invention. The invention further relates to a method treating HER2-positive breast cancer by administering an antibody-drug conjugate according to the invention. Preferred embodiments of the antibody and the molecule of interest are described above.

Process for the Preparation of an Antibody-Drug Conjugate

The invention also relates to a process for the preparation of an Antibody-Drug conjugate according to the invention, comprising the steps of:

(i) contacting an antibody comprising a core N-acetylglucosamine (GlcNAc) substituent with a compound of the formula $S(A)_x$-P in the presence of a suitable catalyst, wherein said core N-acetylglucosamine substituent is optionally fucosylated, wherein said catalyst comprises a mutant catalytic domain from a galactosyltransferase, wherein $S(A)_x$ is a sugar derivative comprising x functional groups A wherein A is independently selected from the group consisting of an azido group, a keto group and an alkynyl group and x is 1, 2, 3 or 4, wherein P is selected from the group consisting of uridine diphosphate (UDP), guanosine diphosphate (GDP) and cytidine diphosphate (CDP), to obtain a modified antibody, wherein a modified antibody is defined as an antibody comprising a GlcNAc-$S(A)_x$ substituent bonded to the antibody via C1 of the N-acetylglucosamine of said GlcNAc-$S(A)_x$ substituent, and wherein said modified antibody is according to Formula (4):

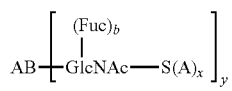

(4)

wherein:

$S(A)_x$ and x are as defined above; AB represents an antibody; GlcNAc is N-acetylglucosamine; Fuc is fucose; b is 0 or 1; and y is 1 to 20; and (ii) reacting said modified antibody with a linker-conjugate, wherein:

(a) when said modified antibody is an azide-modified antibody, said linker-conjugate comprises a (hetero)cycloalkynyl group or an alkynyl group, and one or more molecules of interest; or (b) when said modified antibody is a keto-modified antibody, said linker-conjugate comprises a primary amine group, an aminooxy group or a hydrazinyl group, and one or more molecules of interest; or (c) when said modified antibody is an alkyne-modified antibody, said linker-conjugate comprises an azido group, and one or more molecules of interest, wherein a molecule of interest (D) is conjugated to the antibody via a linker (L); wherein said molecule of interest is an active substance; and wherein an active substance is defined as a substance that is biologically and/or pharmaceutically active.

In a preferred embodiment, said catalyst is a catalyst comprising a mutant catalytic domain from a β(1,4)-galactosyltransferase, preferably selected from the group consisting of GalT Y289L, GalT Y289N and GalT Y289I. In another preferred embodiment, said catalyst is a catalyst comprising a mutant catalytic domain from a β(1,4)-galactosyltransferase, selected from the group consisting of GalT Y289F, GalT Y289M, GalT Y289V, GalT Y289G, GalT Y289I and GalT Y289A, preferably selected from the group consisting of GalT Y289F and GalT Y289M.

In another preferred embodiment, x is 1, 2, 3 or 4, preferably x is 1 or 2, more preferably x is 1. In yet another preferred embodiment, y is 1, 2, 3, 4, 5, 6, 7 or 8, preferably y is 1, 2, 3 or 4 and more preferably y is 1 or 2.

In a specific preferred embodiment, the antibody is a whole antibody and y is 2, and in another preferred embodiment, the antibody is an antibody fragment and y is 1.

In a preferred embodiment of the process for the preparation of an antibody-conjugate according to the invention, said modified antibody is an azide-modified antibody, and said linker-conjugate has the Formula (11) or (11b):

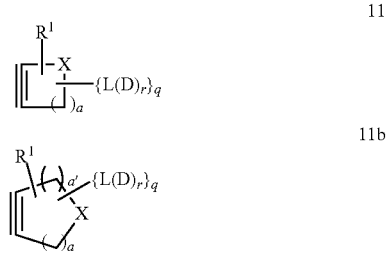

wherein:

D and L are as defined above;

r is 1-20;

$R^1$ is independently selected from the group consisting of hydrogen, halogen, $-OR^5$, $-NO_2$, $-CN$, $-S(O)_2R^5$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^1$ may be linked together to form an annelated cycloalkyl or an annelated (hetero)arene substituent, and wherein $R^5$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

X is $C(R^1)_2$, O, S or $NR^2$, wherein $R^2$ is $R^1$ or $L(D)_r$ wherein L, D and r are as defined above;

q is 0 or 1, with the proviso that if q is 0 then X is N-$L(D)_r$; and a is 0, 1, 2, 3, 4, 5, 6, 7 or 8; and a' is 0, 1, 2, 3, 4, 5, 6, 7 or 8; and a+a'<10.

Preferably, a+a' is 4, 5, 6 or 7, more preferably a+a' is 4, 5 or 6 and most preferably a+a' is 5.

In a further preferred embodiment of the process according to the invention, said modified antibody is an azide-modified antibody, and said linker-conjugate has the Formula (12), (13), (14), (15) or (16).

In another further preferred embodiment of the process according to the invention, said modified antibody is an azide-modified antibody, and said linker-conjugate has the Formula (17):

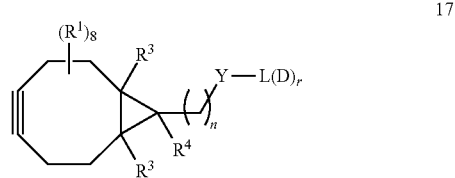

17 wherein:

R¹, L, D and r are as defined above;

Y is O, S or NR², wherein R² is as defined above;

R³ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

R⁴ is selected from the group consisting of hydrogen, Y-L(D)$_r$, —(CH$_2$)$_n$—Y-L(D)$_r$, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted; and n is 1, 2, 3, 4, 5, 6, 7, 8, 9 or 10.

In a further preferred embodiment of the process according to the invention, R¹ is hydrogen. In another preferred embodiment, R³ is hydrogen. In another preferred embodiment, n is 1 or 2. In another preferred embodiment, R⁴ is hydrogen, Y-L(D)$_r$ or —(CH$_2$)$_n$—Y-L(D)$_r$. In another preferred embodiment, R² is hydrogen or L(D)$_r$. In a further preferred embodiment, the linker-conjugate has the Formula 18:

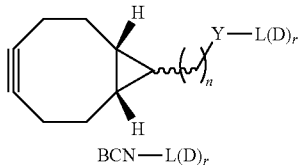

BCN—L(D)$_r$ wherein Y, L, D, n and r are as defined above.

In another further preferred embodiment of the process according to the invention, said modified antibody is an azide-modified antibody, and said linker-conjugate has the Formula (19):

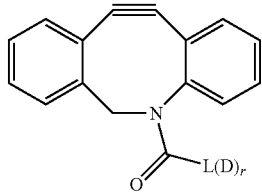

wherein L, D and r are as defined above.

In another preferred embodiment of the process according to the invention, said modified antibody is an azide-modified antibody, and said linker-conjugate has the Formula (15):

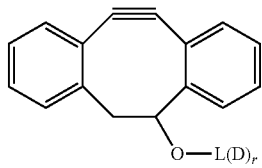

wherein L, D and r are as defined above.

Modified Antibody, Antibody-Conjugate and Antibody-Drug Conjugate According to the Invention The modified antibody, the antibody-conjugate, the antibody-drug conjugate and the processes for the preparation thereof according to the invention have several advantages over the modified antibodies, antibody-conjugates and processes for their preparation known in the art.

As was described above, the known processes for conjugation of a linker-toxin to antibodies still need to be improved, not only in terms of control of both site-specificity and stoichiometry, but also in terms of efficiency of the conjugation process. Despite the ability of ADCs to home in on their targets, the amount of drug estimated to get inside tumors cells is typically <2% of an administered dose. This problem is amplified by the unpredictable conjugation results of ADCs known in the art. It is important to avoid underconjugated antibodies, which decrease the potency, as well as highly conjugated species, which may have markedly decreased circulating half-lives, impaired binding to the target protein, and increased toxicity.

For antibody-drug conjugates, a measure for the loading of molecules of interest (e.g. drugs, active substances) onto the antibody is the so-called Drug to Antibody Ratio (DAR), which gives the average number of active substance molecules per antibody, calculated from a statistical distribution. The theoretical maximum value of DAR for a certain type of ADC is equal to the number of anchoring sites. As was described above, processes for the preparation of ADCs known from the prior art generally result in a product comprising a mixture of antibody-conjugates with a varying number of molecules of interest present in each antibody-conjugate, and in a DAR with a high standard deviation.

One of the advantages of the modified antibodies and the antibody-conjugates according to the invention is that these antibodies and antibody-conjugates are homogeneous, both in site-specificity and stoichiometry. The invention therefore also relates to an antibody-drug conjugate, wherein the antibody-drug conjugate is homogenous. It is further preferred that the antibody-drug conjugate is homogeneous in site-specificity and stoichiometry. It is also preferred that the antibody-drug conjugate is obtained with a drug to antibody ratio (DAR) near to the theoretical value, and with a low standard deviation.

In a preferred embodiment, the modified antibody and antibody-conjugate according to the invention are homogeneous, both in site-specificity and stoichiometry. Herein, an antibody or an antibody-conjugate is considered homogeneous when conjugation is effected only at a predetermined site and with predetermined drug-antibody ratio. An antibody-conjugate is heterogeneous when conjugation of the antibody takes place at different sites in the antibody, leading to a mixture of products with unpredictable drug-antibody ratio. In the latter case, the drug-antibody ratio will be an average of the whole group of antibody-drug conjugates.

In another preferred embodiment, the antibody-conjugate according to the invention has a DAR that is within 10% of its theoretical value.

Said modified antibodies and antibody-conjugates are obtained with a DAR very near to the theoretical value, and with a very low standard deviation. This also means that the antibody-conjugates according to the invention result in a more consistent product for preclinical testing.

Another advantage of the processes and antibodies according to the invention involves the reduction of waste in manufacturing, thereby enhancing companies' cost-of-goods.

In addition, the process for the preparation of a modified antibody and for the preparation of a conjugated antibody according to the invention proceeds very efficiently. Reaction kinetics are very favourable, resulting in a near complete conversion in a relatively short period of time, particularly when compared to processes known in the art, and no or hardly any side products are formed.

Furthermore, when an azide-modified antibody according to the invention is coupled to a linker-conjugate comprising an alkynyl group, or when an alkyne-modified antibody according to the invention is coupled to a linker-conjugate comprising an azide moiety, via a cycloaddition reaction, the resulting triazoles are not susceptible to hydrolysis or other degradation pathways. When a ketone-modified antibody according to the invention is coupled to a linker-conjugate comprising a hydroxylamine or a hydrazine, the resulting oximes or hydrazones are also relatively inert at neutral conditions.

Additional advantages are thus the stability of antibody-conjugates according to the invention, as well as the straightforward and generally applicable process for the introduction of an azido group, a keto group and/or an alkynyl group into an antibody.

As described above, the antibody-conjugates according to the invention have several advantages over antibody-conjugates known in the prior art. One of the advantages of the modified antibodies, the antibody-conjugates and the process for their preparation according to the invention is that these antibodies and antibody-conjugates are homogeneous, both in site-specificity and stoichiometry. The modified antibodies and antibody-conjugates according to the invention are obtained with a DAR very near to the theoretical value, and with a very low standard deviation. This also means that the antibody-conjugates according to the invention result in a more consistent product for preclinical testing.

The properties of an antibody conjugate according to the invention are modulated by designing, expressing, and processing into antibody-drug conjugates the monoclonal antibodies with different glycosylation profiles. The properties that may be modulated are e.g. anti-tumor activity, the maximum tolerated dose, pharmacokinetics such as plasma clearance, therapeutic index, both in terms of efficacy and toxicity, attenuation of the drug, stability of the attachment of the drug and release of the drug after reaching the target. In particular, there is a correlation between location of drug and the in vivo efficacy of ADC.

Figure 24:
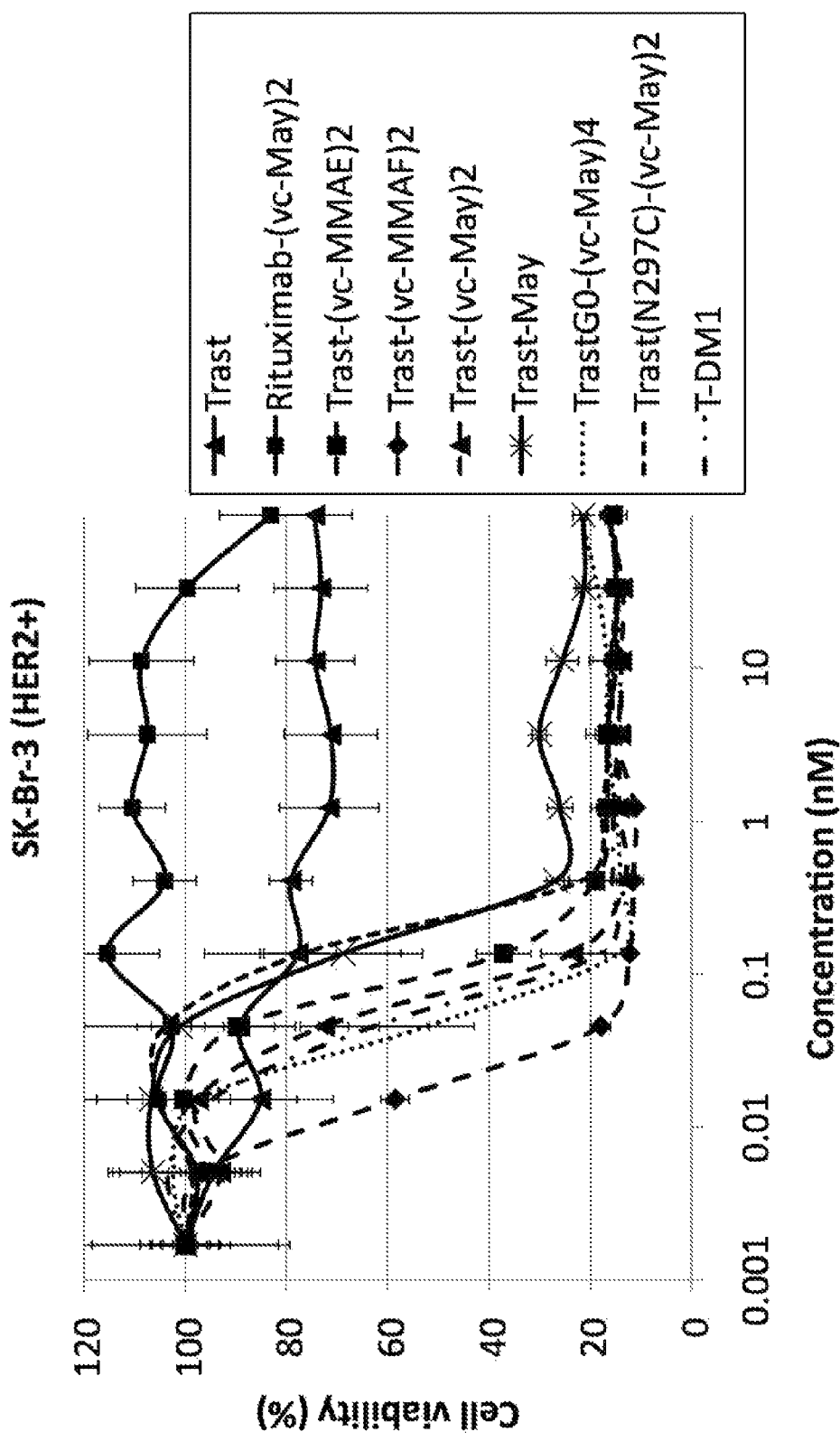
FIG. 24 shows the in vitro cytotoxicity of a range of ADCs on SK-BR-3 cell line.
Figure 25:
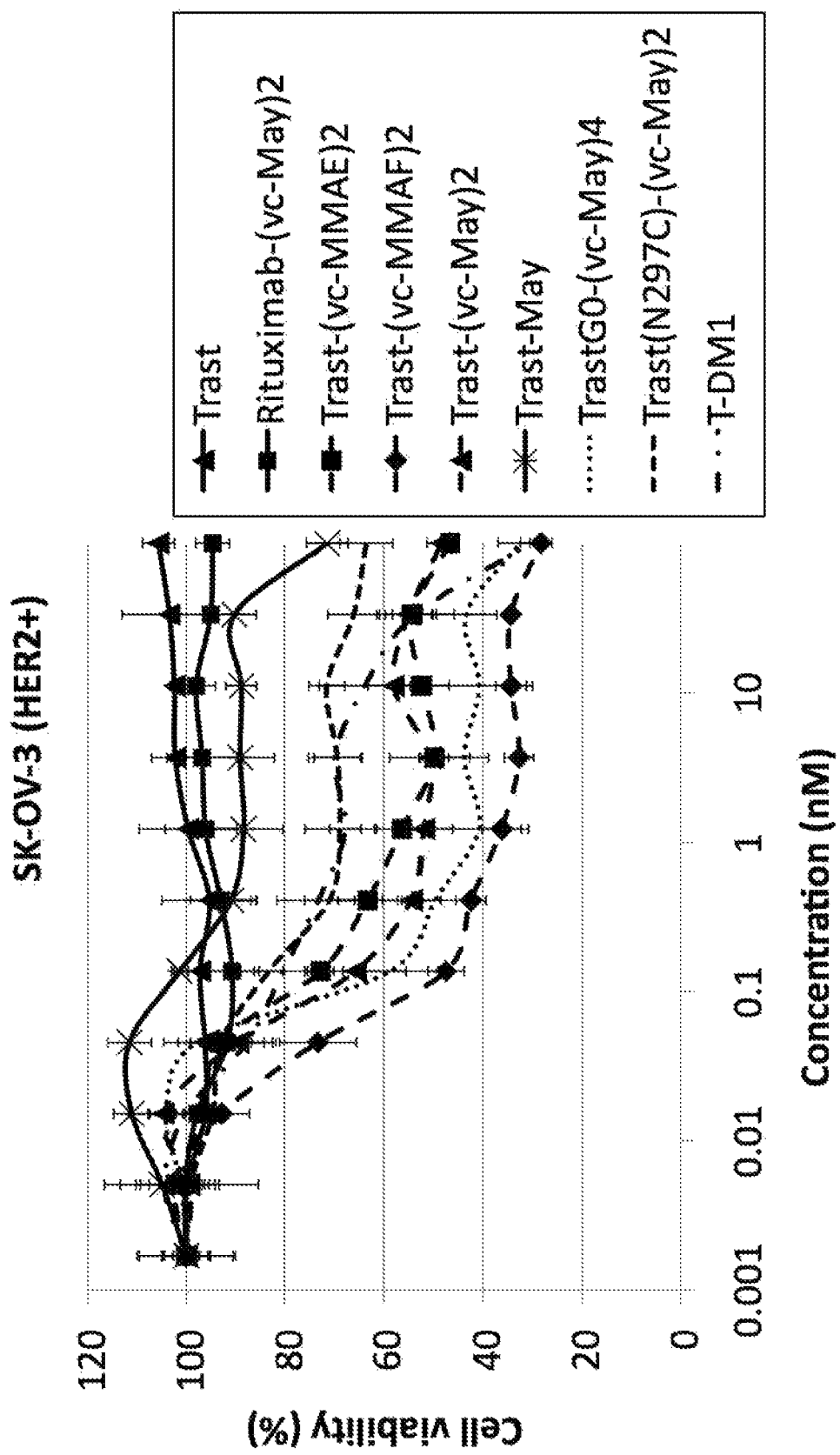
FIG. 25 shows the in vitro cytotoxicity of a range of ADCs on SK-OV-3 cell line.
Figure 26:
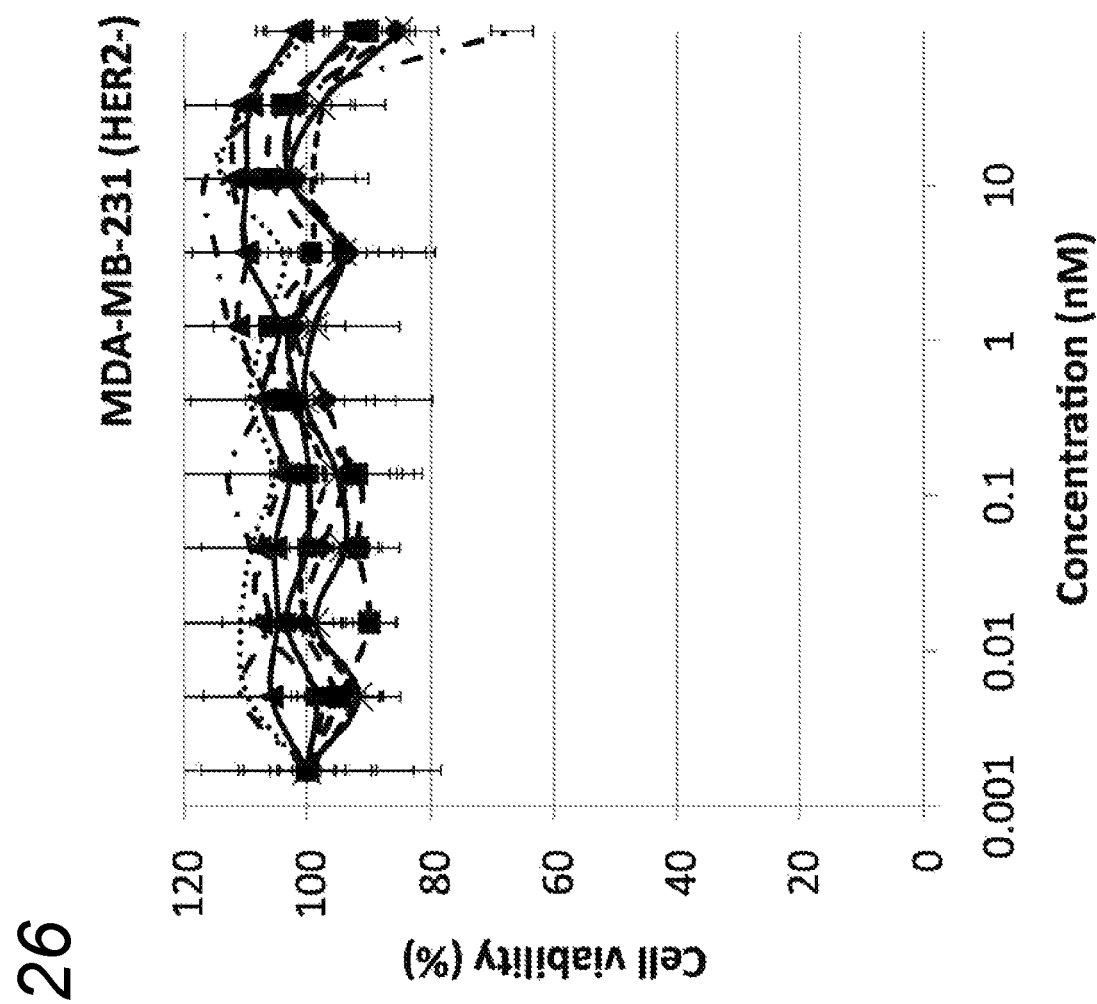
FIG. 26 shows the in vitro cytotoxicity of a range of ADCs on MDA-MB-231 cell line (control).
Figure 27:
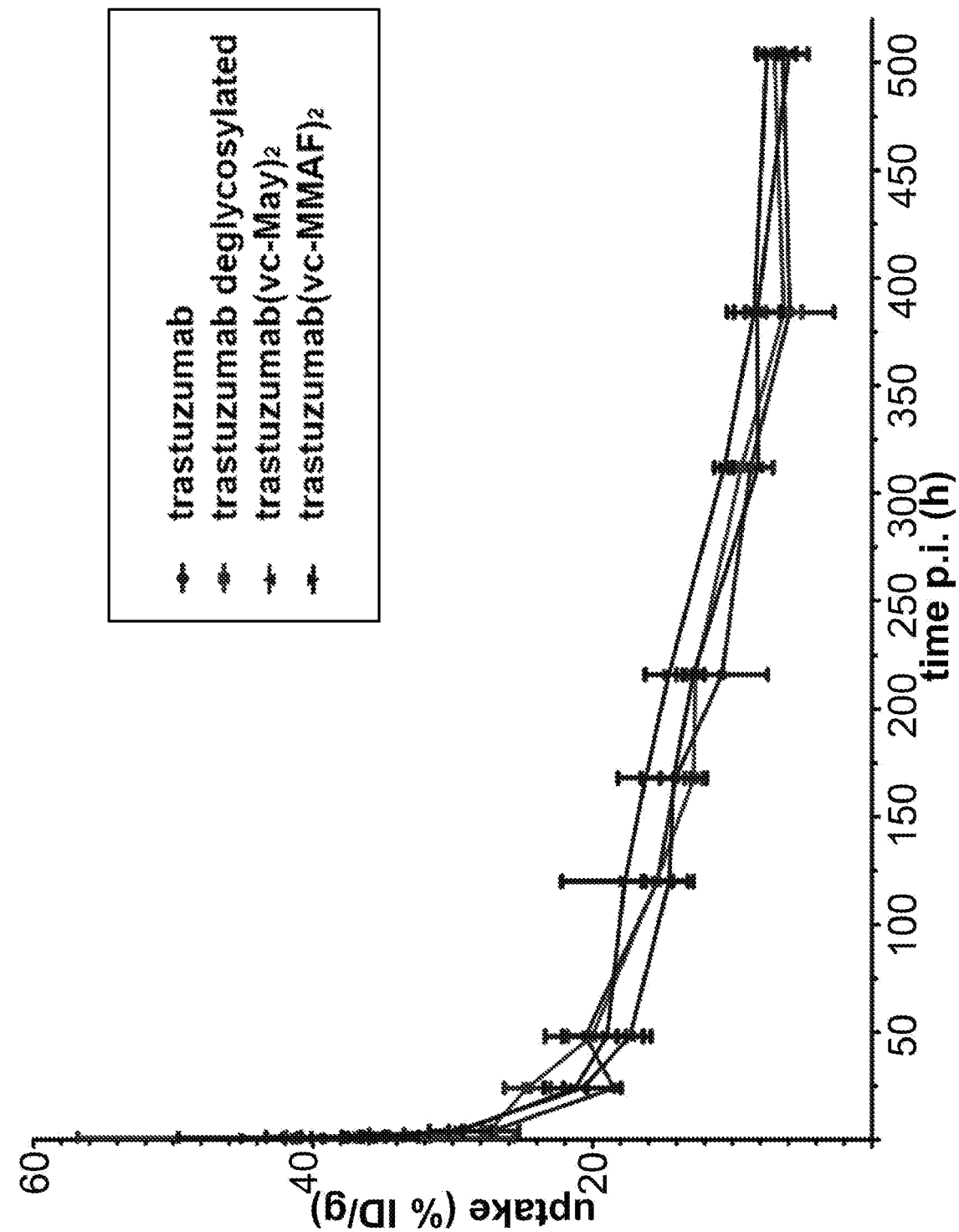
FIG. 27 shows the blood clearance of $^{111}$In-labeled trastuzumab(MMAF)$_2$ derived from 37b, trastuzumab(maytansinoid)$_2$ derived from 39, deglycosylated trastuzumab (obtained by endo S trimming of trastuzumab) and native trastuzumab.
Figure 28:
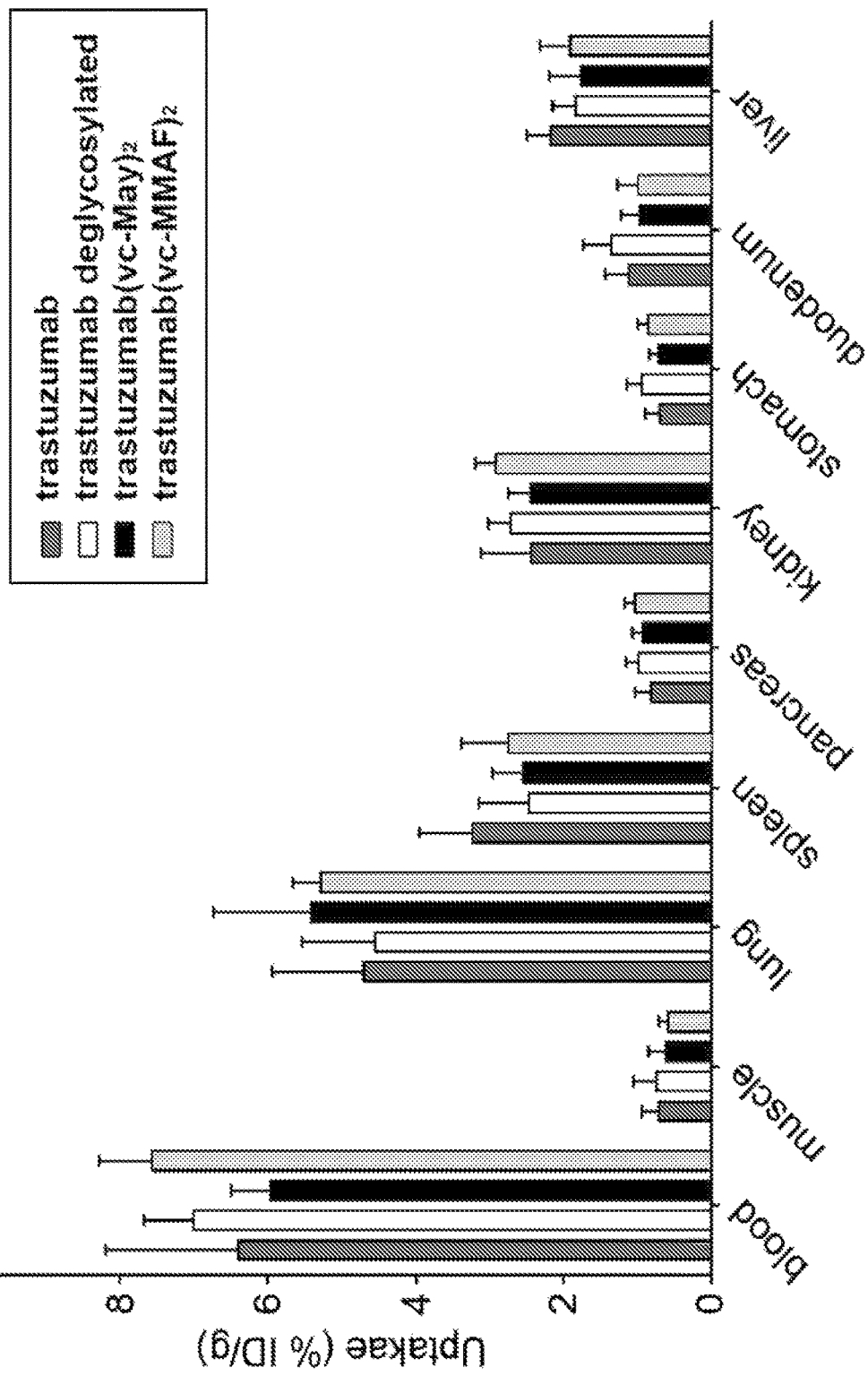
FIG. 28 shows the biodistribution of $^{111}$In-labeled trastuzumab(MMAF)$_2$ derived from 37b, trastuzumab(maytansinoid)$_2$ derived from 39, deglycosylated trastuzumab (obtained by endo S trimming of trastuzumab) and native trastuzumab. Mice were injected with 25 µg and dissected 21 d post-injection. Tissue uptake is expressed as % ID/g.
Figure 29:
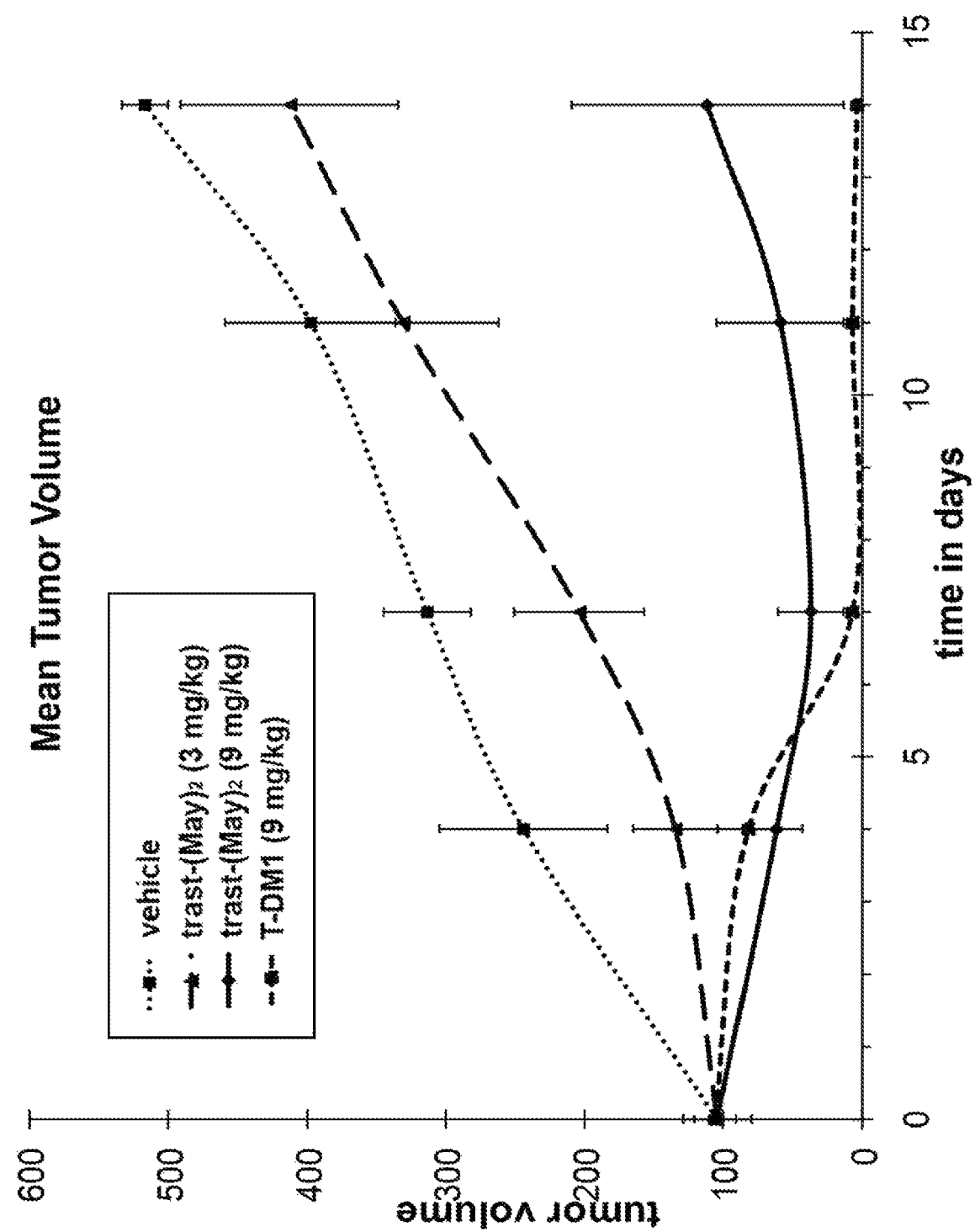
FIG. 29 shows the in vivo efficacy of a mouse xenograft model. ADCs that were evaluated were trastuzumab N297-conjugated to vc-maytansinoid (3 mg/kg and 9 mg/kg) and compared to T-DM1 (9 mg/kg). A cancer patient-derived xenograft (PDX) model was chosen by subcutaneous implantation of tumor code (HBx-13B) in female SHO mice. Tumors were measured on day 0, 4, 7, 11 and 14.
Figure 30:
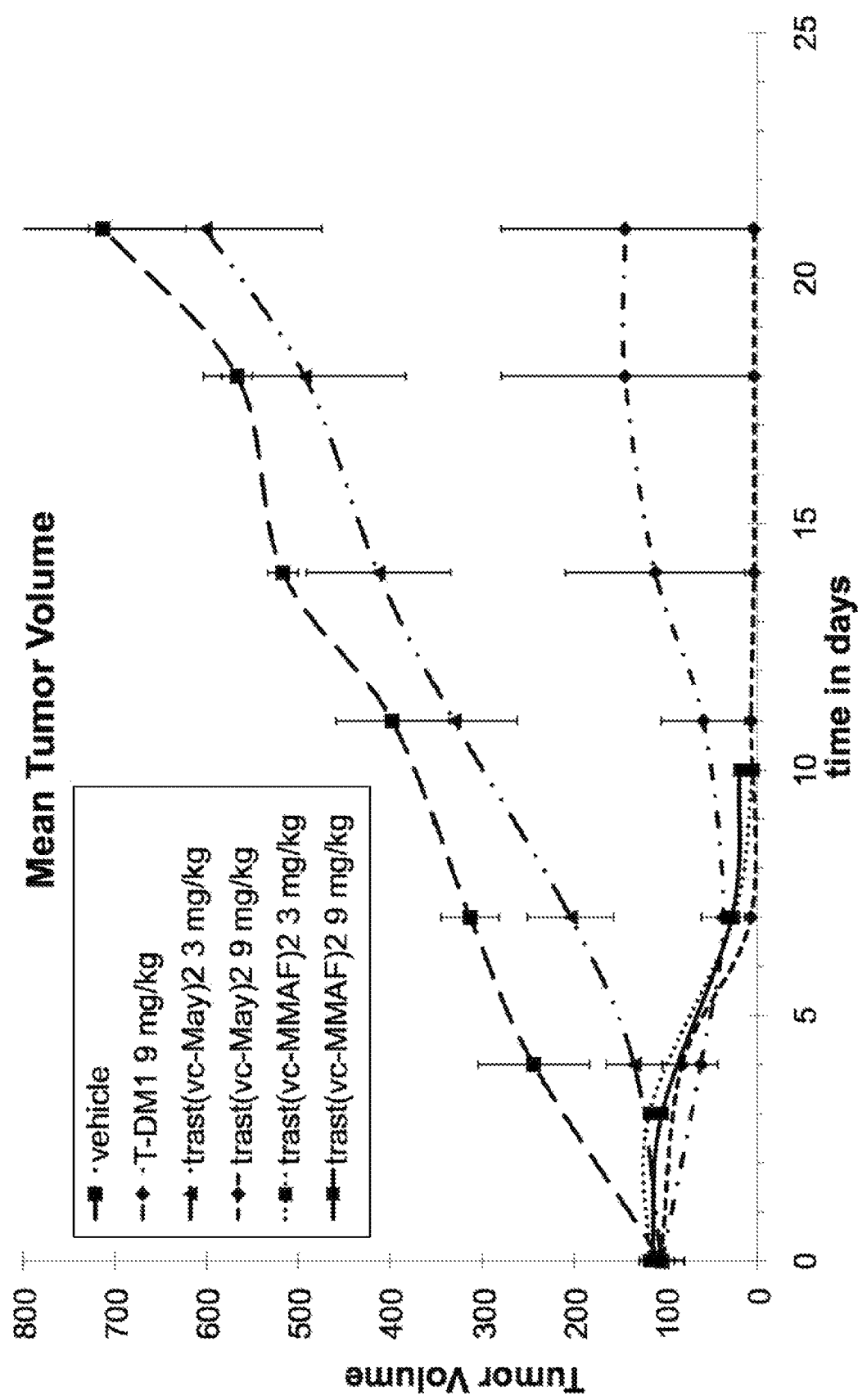
FIG. 30 shows the in vivo efficacy of a mouse xenograft model. ADCs that were evaluated were trastuzumab N297-conjugated to vc-maytansinoid (3 mg/kg and 9 mg/kg), trastuzumab N297-conjugated to vc-MMAF (3 mg/kg and 9 mg/kg) and compared to T-DM1 (9 mg/kg). A cancer patient-derived xenograft (PDX) model was chosen by subcutaneous implantation of tumor code (HBx-13B) in female SHO mice. Tumors were measured on day 0, 4, 7, 11, 14, 18 and 21 for vc-maytansinoid ADCs, T-DM1 and vehicle and on day 0, 3, 7 and 10.

In vivo and in vitro experiments show that the antibody-conjugate according to the invention has a cytotoxic effect on HER2-expressing cells. The in vitro experiments demonstrate that the antibody-drug conjugates according to the invention are able to selectively kill the HER2-expressing cell line with respect to the HER2-negative cell line, as summarized in FIGS. 24-26. The in vivo experiment demonstrates that a single dose of several of the antibody-conjugates according to the invention are able to eliminate a HER2-expressing tumor from a mouse xenograft, as becomes clear from FIGS. 29 and 30. In addition, it is demonstrated that the antibody-conjugates according to the invention have an identical pharmacokinetic profile as the native antibody trastuzumab, as summarized in FIG. 27.

The invention therefore further relates to an antibody-conjugate according to the invention, for use as a medicament. The invention also relates an antibody-conjugate according to the invention, for use in the treatment of cancer. The invention further relates to an antibody-conjugate according to the invention, for use in the treatment of breast cancer, more preferably for use in the treatment of HER2-positive breast cancer.

In a preferred embodiment, the molecule of interest in said antibody-conjugate is an active substance, i.e. a substance that is biologically and/or pharmaceutically active. Preferably, the active substance is a cytotoxin. Examples of cytotoxins include camptothecins, doxorubicin, daunorubicin, taxanes, calicheamycins, duocarmycins, maytansines and maytansinoids (i.e. maytansine derivatives), auristatins or pyrrolobenzodiazepines (PBDs Examples of cytotoxins include camptothecins, staurosporin, doxorubicin, daunorubicin, colchicine, methotrexate, taxanes, calicheamycins, duocarmycins, maytansines and maytansinoids (i.e. maytansine derivatives), auristatins, tubulysin M, cryptophycin or pyrrolobenzodiazepines (PBDs). Examples of auristatins include dolastatin 10, auristatin F, monomethyl auristatin F (MMAF), auristatin E, monomethyl auristatin E (MMAE), auristatin PE, auristatin TP and auristatin AQ. Examples of maytansines and maytansinoids include mertansine and ansamitocin.

In a preferred embodiment, the antibody in said antibody-conjugate is an antibody specifically binding cancer antigen. Examples of an antibody specifically binding cancer antigen include trastuzumab, pertuzumab, cetuximab, rituximab, bevacizumab, girentuximab, gemtuzumab, inotuzumab, alemtuzumab, tositumumab, ipilimumab, ofatumumab, panitumumab, elotuzumab, zanolimumab, obinutuzumab, necitumumab, farletuzumab, vedolizumab, tabalumab, itolizumab, ocrelizumab, epratuzumab, mepolizumab, reslizumab, sarilumab and ramicurumab.

Therefore, in a preferred embodiment, the invention relates to an antibody-conjugate according to the invention, wherein the antibody is an antibody specifically binding cancer antigen and wherein the molecule of interest is a cytotoxin, for use as a medicament. In another preferred embodiment, the invention relates to an antibody-conjugate according to the invention, wherein the antibody is an antibody specifically binding cancer antigen and wherein the molecule of interest is a cytotoxin, for use in the treatment of cancer. In another preferred embodiment, the invention relates to an antibody-conjugate according to the invention, wherein the antibody is an antibody specifically binding cancer antigen and wherein the molecule of interest is a cytotoxin, for use in the treatment of breast cancer, and more preferably for use in the treatment of HER2 positive breast cancer.

In a further preferred embodiment, the invention relates to an antibody-conjugate according to the invention, wherein the antibody-conjugate is trastuzumab-(vc-PABA-MMAF)$_2$ or trastuzumab-(vc-PABA-maytansinoid)$_2$, for use in the treatment of cancer. In a further preferred embodiment, the invention relates to an antibody-conjugate according to the invention, wherein the antibody-conjugate is trastuzumab-(vc-PABA-MMAF)$_2$ or trastuzumab-(vc-PABA-maytansinoid)$_2$, for use in the treatment of breast cancer, more preferably for use in the treatment of HER2 positive breast cancer.

In addition, the invention relates to a method for treating cancer by administering an antibody-drug conjugate according to the invention. The invention also relates to a method of treating breast cancer by administering an antibody-drug conjugate according to the invention. The invention further relates to a method treating HER2-positive breast cancer by administering an antibody-drug conjugate according to the invention. Preferred embodiments of the antibody and the molecule of interest are described above.

Kit of Parts

The invention also relates to a kit of parts, comprising a modified antibody according to the invention and a linker-conjugate. Said modified antibody and linker-conjugate, and preferred embodiments thereof, are described in more detail above.

In a preferred embodiment, the invention relates to a kit of parts, comprising an azide-modified antibody according to the invention and a linker-conjugate according to the Formula 11:

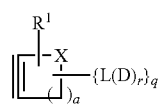

11 wherein $R^1$, X, L, D, a, r and q are as defined above.

Preferred embodiments of the azide-modified antibody and the linker-conjugate 11 are described in more detail above.

EXAMPLES

Synthesis

Examples 1-4: Synthesis of BCN-Doxorubicin 28a and 28b

Figure 7:
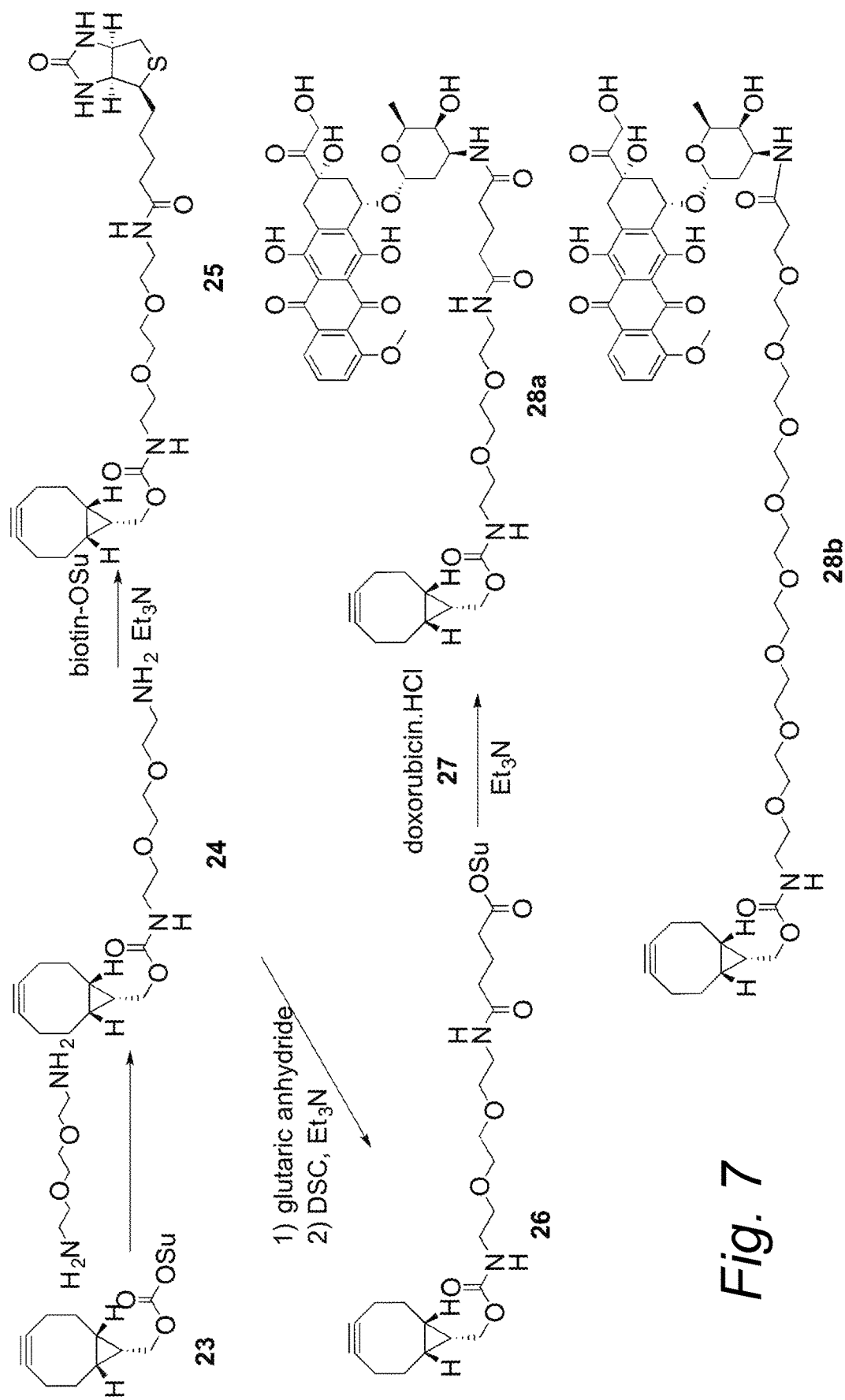
FIG. 7 shows the reaction scheme of the synthesis of non-cleavable linker BCN-doxorubicin conjugates 28a and 28b.

The reaction scheme of the synthesis of linker-conjugate BCN-doxorubicine 28a starting from BCN-OSu 23, as performed in Examples 1-4, is shown in FIG. 7.

Example 1. Synthesis of BCN-Amine 24

To a solution of 2,2'-(ethylenedioxy)bis(ethylamine) (11.78 mL, 80.5 mmol) in DCM (200 mL) was added BCN-OSu 23 (7.82 g, 26.8 mmol) in DCM (100 mL) dropwise over 3 h. After complete addition the mixture was stirred for 10 min followed by washing with saturated aqueous $NH_4Cl$ (3×200 mL). The organic layer was dried over $Na_2SO_4$, filtrated and concentrated in vacuo. Flash column chromatography (DCM:MeOH 99:1-93:7+1% $Et_3N$) gave product 24 (5.95 g, 54.7 mmol, 68%). $^1$H-NMR (300 MHz, $CDCl_3$) δ 5.38 (s, 1H), 4.13 (d, J=8.1 Hz, 2H), 3.59 (s, 4H), 3.56-3.50 (m, 4H), 3.35 (q, J=5.1 Hz, 2H), 2.88 (t, J=5.1 Hz, 2H), 2.32 (br s, 2H), 2.27-2.15 (m, 6H), 1.62-1.42 (m, 2H), 1.33 (qn, J=8.7 Hz, 1H), 0.97-0.85 (m, 2H). $^{13}$C-NMR ($CDCl_3$, 75 MHz) δ 156.4, 98.3, 68.7 (2C), 62.2, 45.5, 40.3, 40.2, 28.6, 20.9, 19.6, 17.3. HRMS (ESI+) calcd for $C_{17}H_{28}N_2NaO_4$ (M+Na$^+$) 347.1947. found 347.1952.

Example 2. Synthesis of BCN-Biotin 25

To a solution of BCN derivative 24 (0.80 g, 2.47 mmol) in DCM (25 mL) were added biotin-OSu (0.93 g, 2.71 mmol) and $Et_3N$ (0.86 mL, 6.16 mmol). The reaction mixture was stirred for 5 h and subsequent saturated aqueous $NaHCO_3$ (20 mL) was added. The organic layer was washed with saturated aqueous $NaHCO_3$ (2×20 mL), dried over $Na_2SO_4$, filtrated and concentrated under reduced pressure. Flash column chromatography (DCM:MeOH 99:1-92:8) afforded BCN biotin 25 (1.14 g, 2.1 mmol, 84%). $^1$H-NMR (400 MHz, $CDCl_3$): δ 6.57 (s, 1H), 6.44 (s, 1H), 5.48 (s, 1H), 5.37 (s, 1H), 4.52-4.48 (m, 1H), 4.33-4.30 (m, 1H), 4.16 (d, J=8 Hz, 2H), 3.62 (s, 4H), 3.57 (t, J=5.2 Hz, 4H), 3.45 (q, J=5.2 Hz, 2H), 3.40-3.36 (m, 2H), 3.17-3.12 (m, 1H), 2.92 (dd, J=8, 4.8 Hz, 1H), 2.72 (d, J=12.8 Hz, 1H), 2.33-2.18 (m, 8H), 1.88 (br s, 1H), 1.80-1.57 (m, 6H), 1.49-1.33 (m, 3H), 0.95 (t, J=9.6 Hz, 2H). $^{13}$C-NMR ($CDCl_3$, 75 MHz) δ 172.9, 163.6, 156.4, 98.3, 69.6, 61.3, 59.7, 55.2, 40.3, 40.0, 38.7, 35.5, 28.6, 27.8, 27.6, 25.1, 21.0, 19.7, 17.3. HRMS (ESI+) calcd for $C_{27}H_{43}N_4O_6S$ (M+H$^+$) 551.2903. found 551.2911.

Example 3. Synthesis of Activated Ester 26

BCN-amine 24 (3.6 g, 11.1 mmol) was dissolved in DCM (150 mL) and glutaric anhydride (1.39 g, 12.2 mmol) and $Et_3N$ (4.61 mL, 33.3 mmol) were added. The reaction mixture was stirred for 2 h followed by the addition of DSC (4.3 g, 16.7 mmol). After 2 h the reaction was quenched with $H_2O$ (100 mL) and the organic layer was washed with water (2×150 mL), dried over $Na_2SO_4$, filtrated and concentrated in vacuo. Flash column chromatography (EtOAc:MeOH 99:1-94:6) afforded activated ester 26 (4.63 g, 8.6 mmol, 78%).

$^1$H-NMR (300 MHz, $CDCl_3$): δ 4.14 (d, J=8.1 Hz, 2H), 3.59 (s, 4H), 3.57-3.52 (m, 4H), 3.44 (q, J=5.1 Hz, 2H), 3.35 (q, J=4.8 Hz, 2H). 2.83 (br s, 4H), 2.67 (t, J=7.2 Hz, 2H), 2.33-2.16 (m, 7H), 2.08 (qn, J=6.9 Hz, 2H), 1.65-1.49 (m, 2H), 1.33 (t, J=9.0 Hz, 1H), 0.97-0.87 (m, 2H).

LRMS (ESI+) calcd for $C_{26}H_{37}N_3O_9$ (M+H$^+$) 536.26. found 536.0.

Example 4. Synthesis of BCN-Doxorubicin Conjugate 28a

To a solution of activated ester 26 (5 mg, 0.0093 mmol) and doxorubicine.HCl (27, 10 mg, 0.017 mmol) in DMF (0.5 mL) was added $Et_3N$ (5 μL, 0.036 mmol) and the mixture was stirred overnight. The solvent was removed under reduced pressure and the crude product was purified with flash column chromatography (DCM:MeOH 99:1-80:20) to afford BCN-doxorubicine 28a (6 mg, 0.0062 mmol, 66%). LRMS (ESI+) calcd for $C_{49}H_{61}N_3O_{17}$ (M+H$^+$) 964.4. found 963.9.

Example 4-2. Synthesis of BCN-Doxorubicin Conjugate 28b

To a solution of $H_2N$-PEG$_8$-COOH (822 mg, 1.86 mmol) in THF:$H_2O$ 1:1 (20 mL) were added BCN-OSu (23) (651 mg, 2.23 mmol) and $Et_3N$ (774 μL, 5.59 mmol). The reaction was stirred at r.t. for 1.5 h and acidified to pH 1 followed by extraction with EtOAc (3×35 mL). The combined organic layers were dried over $Na_2SO_4$, filtered and the solvent removed under reduced pressure. The crude product was then dissolved in dry DCM (20 mL) and subsequently DCC (461 mg, 2.23 mmol) and NHS (257 mg, 2.23 mmol) were added. After stirring at r.t. for 1 h, the reaction was filtered and the filtrate concentrated in vacuo. Flash chromatography (MeCN, MeCN:$H_2O$ 30:1) afforded BCN-PEG$_8$-COOSu.

$^1$H-NMR (300 MHz, $CDCl_3$): δ 5.44 (br s, 1H), 4.14) d, J=8.1 Hz, 2H), 3.84 (t, J=6.3 Hz, 2H), 3.68-3.63 (m, 30H), 3.56 (t, J=5.2 Hz, 2H), 3.34 (q, J=5.4 Hz, 2H), 2.90 (t, J=6.3 Hz, 2H), 2.85 (s, 4H), 2.36-2.14 (m, 6H). 1.72-1.49 (m, 2H), 1.36 (qn, J=8.7 Hz, 1H), 1.02-0.88 (m, 2H).

LRMS (ESI+) calcd for $C_{34}H_{54}N_2O_{14}$ (M+Na$^+$) 737.35. found 737.3.

To a solution of doxorubicine.HCl (27, 500 mg, 0.862 mmol) in anhydrous DMF (10 mL) were added triethylamine (361 μL, 262 mg, 2.59 mmol) and a solution of BCN- PEG$_8$-COOSu (678 mg, 0.948 mmol) in DMF (10 mL). The resulting mixture was stirred for 22 h and concentrated with 3 g of silicagel. After purification via column chromatography, the product was obtained as a red amorphous material (757 mg, 0.66 mmol, 77%).

LRMS (HPLC, ESI−) calcd for $C_{57}H_{77}N_2O_{22}$ (M−H$^+$) 1141.5. found 1142.2.

Figure 8:
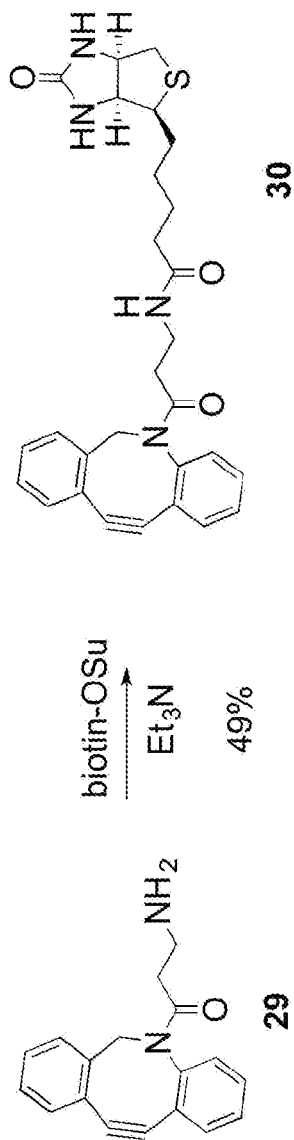
FIG. 8 shows the reaction scheme for the synthesis of DIBAC-biotin conjugate 30

Example 5. Synthesis of DIBAC-biotin 30 (Schematically depicted in FIG. 8) To a solution of amine 29, commercially available from ClickChemistryTools (50 mg, 0.18 mmol) in DMF (2 mL) was added biotin-OSu (62 mg, 0.18 mmol) and Et$_3$N (50 μL, 0.36 mmol). The reaction mixture was stirred for 3 h followed by concentration under reduced pressure. Flash column chromatography (DCM:MeOH 99:1-90:10) afforded DIBAC-biotin 30 (44 mg, 0.09 mmol, 49%). $^1$H-NMR (300 MHz, CDCl$_3$): δ 7.66-7.62 (m, 1H), 7.40-7.24 (m, 7H), 6.67-6.60 (m, 1H), 6.53-6.49 (m, 1H), 5.75 (d, J=8.8 Hz, 1H), 5.13 (dd, J=2.9, 14.0 Hz, 1H), 4.47-4.43 (m, 1H), 4.29-4.28 (m, 1H), 3.68 (d, J=13.9 Hz, 1H), 3.34-3.30 (m, 1H), 3.17-3.08 (m, 2H), 2.92-2.67 (m, 3H), 2.50-2.42 (m, 1H), 2.10-1.95 (m, 2H), 1.73-1.24 (m, 6H). LRMS (ESI+) calcd for $C_{28}H_{30}N_4O_3S$ (M+H$^+$) 503.2. found 503.1.

Examples 6-9: Synthesis of BCN-Doxorubicin Conjugate 35

Figure 9:
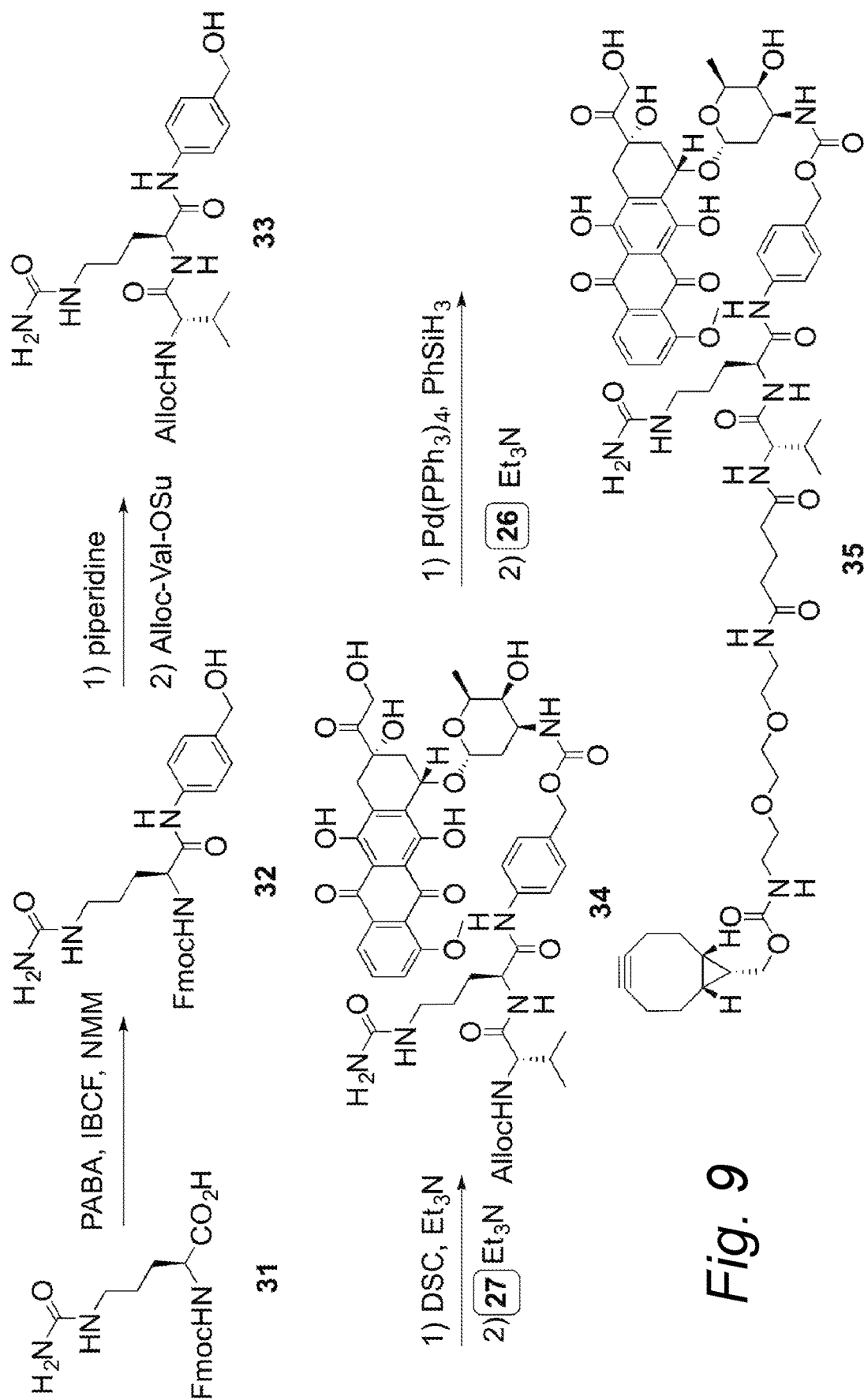
FIG. 9 shows the reaction scheme of the synthesis of cleavable linker BCN-vc-PABA-doxorubicin conjugate 33 starting from Fmoc-citrulline 31.

The reaction scheme for the synthesis of BCN-doxorubicine conjugate 35 starting from Fmoc-citrulline 31, as performed in Examples 7-10, is shown in FIG. 9.

Example 6. Synthesis of Citrulline Derivative 32

Isobutylchloroformate (99 μL, 0.76 mmol) and N-methylmorpholine (83 μL, 0.76 mmol) were added to a solution of Fmoc-citrulline 31 (300 mg, 0.76 mmol) in THF at −40° C. The solution was stirred for 2 h followed by the addition of p-aminobenzylalcohol (112 mg, 0.91 mmol) and N-methylmorpholine (100 μL, 0.91 mmol). After 1 h stirring the solution was slowly warmed to rt and after 2 h the reaction mixture was concentrated under reduced pressure. Purification via flash column chromatography (DCM:MeOH 99:1-80:20) afforded citrulline derivative 32 (346 mg, 0.69 mmol, 90%). LRMS (ESI+) calcd for $C_{28}H_{30}N_4O_5$ (M+H$^+$) 503.2. found 503.1.

Example 7. Synthesis of Dipeptide 33

Citrulline derivative 32 (100 mg, 0.20 mmol) was dissolved in DMF (1.6 mL) and piperidine (333 μL) was added. After 2 h the reaction was concentrated under reduced pressure and the crude product was dissolved in DMF (2 mL). Alloc-Val-OSu (60 mg, 0.20 mmol) and Et$_3$N (58 μL, 0.40 mmol) were added, the mixture was stirred overnight and subsequent concentrated in vacuo. Purification via flash column chromatography (DCM:MeOH 99:1-90:10) afforded dipeptide 33 (65 mg, 0.14 mmol, 70%). LRMS (ESI+) calcd for $C_{22}H_{33}N_5O_6$ (M+H$^+$) 464.2. found 464.0.

Example 8. Synthesis of Dipeptide-Doxorubicin 34

To a solution of dipeptide 33 (40 mg, 0.086 mmol) in DMF (0.5 mL) Et$_3$N (36 μL, 0.26 mmol) and DSC (66 mg, 0.26 mmol) were added. The reaction mixture was stirred overnight followed by concentration under reduced pressure. Purification via flash column chromatography (DCM:MeOH 99:1-90:10) afforded the product (30 mg, 0.05 mmol, 58%) which was immediately dissolved in DMF (0.5 mL). Doxorubicin.HCl 27 (29 mg, 0.05 mmol) and Et$_3$N (20 μL, 0.15 mmol) were added, the reaction mixture was stirred for 2 h and subsequent concentrated under reduced pressure. Purification via flash column chromatography (DCM:MeOH 99:1-80:20) afforded dipeptide-doxorubicin 34 (34 mg, 0.033 mmol, 66%). LRMS (ESI+) calcd for $C_{50}H_{60}N_6O_{18}$ (M+H$^+$) 1033.4. found 1032.9.

Example 9. Synthesis of BCN-Doxorubicin Conjugate 35

Dipeptide-doxorubicine 34 (8 mg, 0.008 mmol) was dissolved in DMF (0.5 mL) and triphenylsilane (7 μL, 0.054 mmol) and Pd(PPh$_3$)$_4$ (0.6 mg, 0.0005 mmol) were added. After stirring overnight the reaction was concentrated under reduced pressure and suspended in DCM (2 mL). After filtration the crude product was obtained as a red solid which was dissolved in DMF (0.5 mL). BCN derivative 26 (3 mg, 0.006 mmol) and Et$_3$N (2 μL, 0.014 mmol) were added and the reaction was stirred overnight. The solvents were removed under reduced pressure and purification via flash column chromatography (DCM:MeOH 99:1-60:40) afforded BCN-doxorubicine conjugate 35 (3 mg, 0.002 mmol, 27%). LRMS (ESI+) calcd for $C_{68}H_{88}N_8O_{22}$ (M+H$^+$) 1369.8. found 1369.3.

Example 9-2. Synthesis of BCN-vc-PABA-MMAE (37a)

To a solution of Val-Cit-PAB-MMAF.TFA (8.0 mg, 6.5 μmol) and triethylamine (3.5 μL) in anhydrous DMF (1 mL) was added BCN-PEG$_2$-OSu (2.7 mg, 6.5 μmol) (36) as a solution in DMF (0.78 mL) The product (6 mg, 4 μmol, 62%) was obtained after purification via reversed phase HPLC (C18, gradient H$_2$O/MeCN). LRMS (ESI+) calcd for $C_{74}H_{115}N_{11}NaO_{17}$ (M+Na$^+$) 1452.84. found 1452.7.

Example 9-3. Synthesis of BCN-vc-PABA-MMAF (37b)

To a solution of Val-Cit-PAB-MMAF.TFA (17.9 mg, 14.3 μmol) in DMF (2 mL) was added BCN-PEG$_2$-OSu (17.9 mg, 14.3 μmol) (36) as a solution in DMF (0.78 mL) and triethylamine (6.0 μL). The product (7 mg, 5 μmol, 35%) was obtained after purification via reversed phase HPLC (C18, gradient H$_2$O/MeCN 1% AcOH). LRMS (HPLC, ESI+) calcd for $C_{74}H_{114}N_{11}O_{18}$ (M+H$^+$) 1444.83. found 1445.44.

Example 9-4. Synthesis of BCN-MMAF (38)

To a solution of Val-Cit-PABA-MMAF (7.6 mg, 0.0074 mmol) in DMF (0.2 mL) was added BCN-OSu ester 26 (8 mg, 0.015 mmol) and Et$_3$N (3 μL, 2.2 mg, 0.022 mmol). After overnight reaction, the mixture was concentrated. Purification via column chromatography (MeOH/DCM 1/3) yielded the desired product (3.4 mg, 0.0022 mmol, 29%). LRMS (HPLC, ESI+) calcd for $C_{80}H_{125}N_{12}O_{19}$ (M+H$^+$) 1557.92. found 1558.16.

Example 9-5. Synthesis of BCN-vc-PABA-Maytansinoid (39)

To a suspension of Val-Cit-PABA-β-alaninoyl-maytansinoid (commercially available from Concortis) (27 mg, 0.022 mmol) in MeCN (2 mL) was added triethylamine (9.2 μL, 6.7 mg, 0.066 mmol) and a solution of BCN-PEG$_2$ OSu carbonate (9.2 mg, 0.022 mmol) in MeCN (1 mL). After 23 h, the mixture was poured out in a mixture of EtOAc (20 mL) and water (20 mL). After separation, the organic phase was dried ($Na_2SO_4$) and concentrated. After purification via column chromatography (EtOAc MeOH/EtOAc 1/4) 22 mg (0.015 mmol, 70%) of the desired product was obtained. LRMS (ESI+) calcd for $C_{70}H_{97}ClN_{10}O_{20}$ (M+H$^+$) 1432.66. found 1434.64.

Example 9-6. Synthesis of Maleimide-vc-PABA-Maytansinoid (40)

To a solution of Val-Cit-PABA-β-alaninoyl-maytansinoid (13.9 mg, 0.011 mmol) (commercially available from Concortis, San Diego, USA) in anhydrous DMF (1 mL) was added triethylamine (4.5 µL, 3.3 mg, 0.033 mmol) and N-succinimidyl 6-maleimidocaproate (3.9 mg, 0.013 mmol). After stirring for an appropriate time, the mixture was partitioned over EtOAc (20 mL) and aqueous saturated $NaHCO_3$ (10 mL). After separation, the aqueous layer was extracted with EtOAc (20 mL). The combined organic layers were dried ($Na_2SO_4$) and concentrated. After purification via reversed phase HPLC (C18, gradient $H_2O$/MeCN), 10 mg (0.0077 mmol) of the desired product was obtained. LRMS (HPLC, ESI+) calcd for $C_{64}H_{88}ClN_{10}O_{18}$ (M+H$^+$) 1390.60. found 1390.52.

The above Examples 9-3 to 9-6 are schematically depicted in Scheme 10a.

Example 9-7. Synthesis of DIBAC-vc-PABA-MMAF 41 (Schematically Depicted in Scheme 11)

DIBAC-amine 29, commercially available from ClickChemistryTools (430 mg, 1.50 mmol) was dissolved in DCM (15 mL) and treated with glutaric acid anhydride (213 mg, 1.87 mmol) and $Et_3N$ (647 µL, 4.67 mmol) at rt. The reaction was stirred for 2 h, followed by the addition of DSC (478 mg, 1.87 mmol). After another 2 h of stirring at rt, DCM (30 mL) was added and the reaction was washed with $H_2O$ (3×20 mL). The organic phase was dried over $Na_2SO_4$ and the solvent removed under reduced pressure. Flash chromatography (0:100-2:98 EtOAc:MeOH) afforded the DIBAC-OSu ester (368 mg, 0.75 mmol, 48%).

Next, to a solution of the DIBAC-OSu ester (1 mg, 0.003 mmol) in DMF (0.2 mL) was added vc-PABA-MMAF (2 mg, 0.002 mmol) and triethylamine (1 µL, 0.007 mmol). The solution was stirred overnight followed by concentration. Purification with HPLC (reversed phase, MeCN:$H_2O$+0.1% TFA) gave 41 (0.9 mg, 0.0006 mmol, 33%). LCMS analysis gave one peak with mass 1510.40 (expected for $C_{81}H_{113}N_{12}O_{16}$=1510.83).

Examples 9-8-9-11. General Protocol for Synthesis of Other Doxorubicin-Cyclooctynes To a 0.1 M solution of the activated cyclooctyne (1-2 equiv) in DCM/DMF (1:1) was added doxorubicin.HCl (27, 1 equiv) and triethylamine (1.5 equiv). The red solution was stirred overnight followed by concentration in vacuo. The crude mixture was prepacked on silica using DMF as solvent followed by column chromatography (DCM→DCM:MeOH 8:2) to yield the desired product.

Example 9-9. Synthesis of Doxorubicin-MFCO 42

MFCO-OSu ester (commercially available from Berry and Associates, Dexter, Mich., USA) (3.4 mg, 0.009 mmol) was reacted with doxorubicin.HCl (27, 5 mg, 0.009 mmol) according to the general procedure to yield doxorubicin-MCFO 42 (5 mg, 0.006 mmol, 69%). LCMS analysis gave one peak with mass 831.88 (expected for $C_{42}H_{49}FN_2NaO_{13}$=831.31).

Example 9-10. Synthesis of Doxorubicin-Cyclooctyne 43

Cycloct-4-yn-1-ol (*Chem. Ber.* 1986, 119, 297-312.) was converted into its p-nitrophenyl carbonate derivative (5 mg, 0.017 mmol), which was reacted with doxorubicin.HCl (27, 5 mg, 0.009 mmol) according to the general procedure to afford doxorubicin-cyclooctyne 43 (6 mg, 0.008 mmol, 94%).

Example 9-11. Synthesis of Doxorubicin-DIBO 44

According to the general procedure DIBO OSu carbonate (commercially available from LifeTechnologies, 5 mg, 0.013 mmol) was reacted with doxorubicin (27, 5 mg, 0.009 mmol) to afford DIBO-doxorubicin 44 (7 mg, 0.008 mmol, 90%).

The above Examples 9-8 to 9-11 are schematically depicted in Scheme 12.

Example 9-12. Synthesis of Alkyne-Biotin 45

To a solution of biotin-$PEG_3$-$NH_2$ in dichloromethane (6 mL) was added triethylamine (54 µL, 39 mg, 0.39 mmol) and pent-4-ynoic acid succinimidyl ester (25 mg, 0.13 mmol). After 19 h, the reaction mixture was concentrated and the residue was purified via column chromatography (5→20% MeOH in DCM). The purified product was dissolved in DCM, filtered and concentrated, which yielded the desired product as a white solid (52 mg, 0.11 mmol, 85%).

Example 9-13. Synthesis of O-Alkyl Hydroxylamine Biotin 47

To a solution of diethyleneglycol (0.89 mL, 1 g, 9.42 mmol) in 80 mL dry THF was add $PPh_3$ (5.43 g, 20.7 mmol) and N-hydroxyphthalimide. After cooling to 0° C. a 40% DEAD solution in toluene was added (9.44 mL, 20.7 mmol). The mixture was stirred for 21 h. The product was filtered off and washed with EtOAc. The product was obtained as a white solid (1.73 g, 4.37 g). $^1$H NMR (300 MHz, $CDCl_3$) δ (ppm) 7.85-7.66 (m, 8H), 4.31-4.20 (m, 4H), 3.92-3.78 (m, 4H).

Next, 1.5 g (3.78 mmol) of the product obtained in the previous step was dissolved in 7 N $NH_3$ in MeOH, heated to 40° C. and stirred for 20 h. It was then cooled to rt while argon was bubbled through the reaction mixture. The reaction mixture was concentrated and the residue was dissolved in DCM (50 mL), filtered and concentrated. The residue was purified via column chromatography (2→5% MeOH in DCM). Yield: 0.46 g (3.38 mmol, 89%). $^1$H NMR (300 MHz, $CDCl_3$) δ 5.51 (s, 4H), 3.88-3.82 (m, 4H), 3.71-3.64 (m, 4H).

The above Examples 9-12 and 9-13 are schematically depicted in Scheme 13.

Examples 9-14-9.17: Synthesis of UDP-GalNAc Derivatives 52-55

Figure 14:
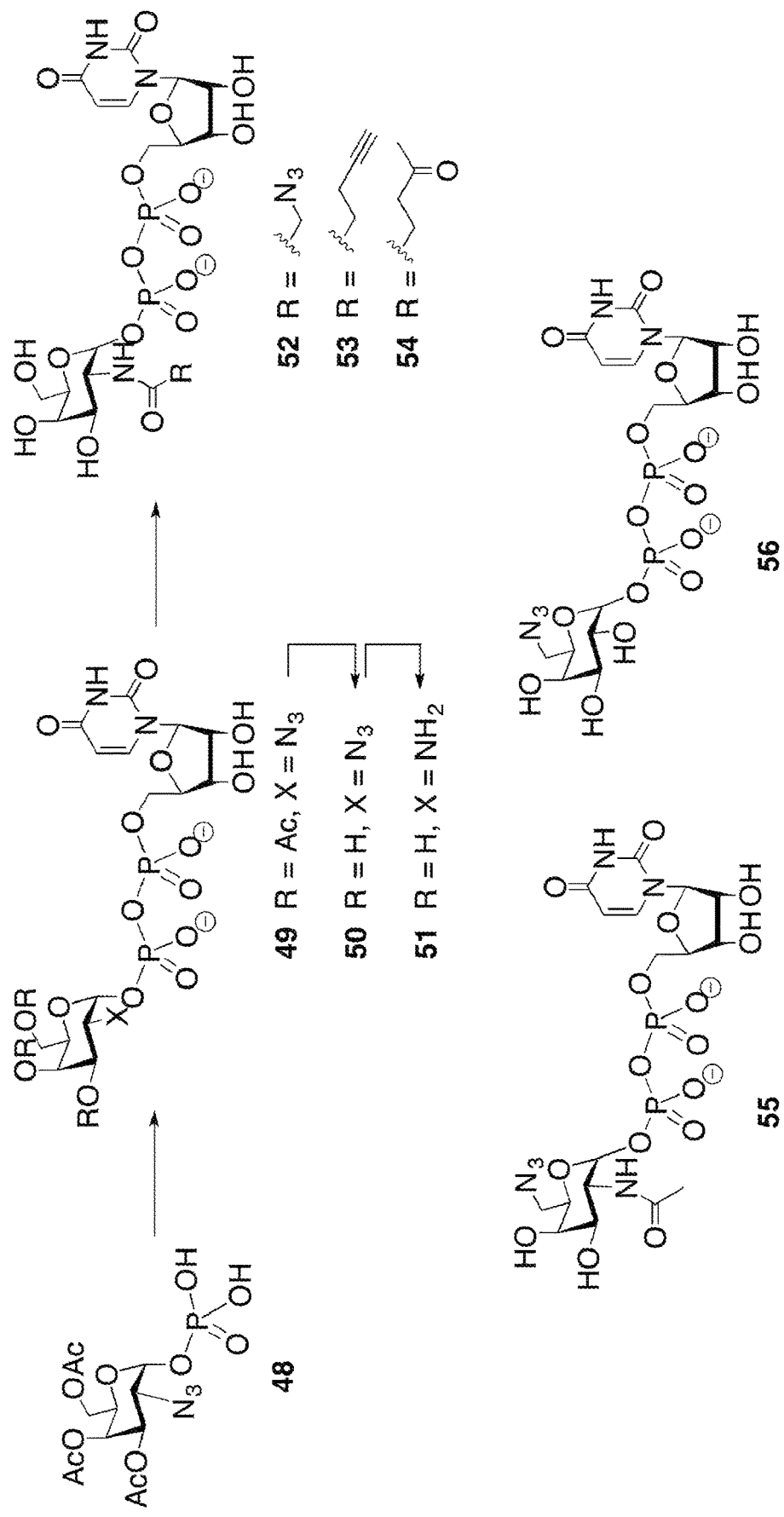
FIG. 14 shows the reaction scheme for the synthesis of 2-modified UDP-GalNAc derivatives 52-54 and the structures of 6-azido modified UDP-Gal (55) and UDP-GalNAc (56).

The reaction scheme of the synthesis of UDP-GalNAc derivatives 52-54, starting from 51, is shown in FIG. 14. Compounds 55 and 56 were purchased from Glycohub, Inc. (USA).

Example 9-14. Synthesis of UDP-GalNH$_2$ 51

Compound 48 was prepared from D-galactosamine according to the procedure described for D-glucosamine in Linhardt et al., *J. Org. Chem.* 2012, 77, 1449-1456. $^1$H-NMR (300 MHz, CD$_3$OD): δ 5.69 (dd, J=6.84, 6.84 Hz, 1H), 5.43-5.41 (m, 1H), 5.35 (dd, J=10.9, 3.4 Hz, 1H), 4.54 (t, J=6.48 Hz, 1H), 4.23-4.12 (m, 1H), 4.04 (dd, J=10.9, 6.1 Hz, 1H), 3.82 (dt, J=11.1, 2.7 Hz, 1H), 2.12 (s, 3H), 2.00 (s, 3H), 1.99 (s, 3H). LRMS (ESI−) calcd for C$_{12}$H$_{18}$N$_3$O$_{11}$ (M−H$^+$) 410.06. found 410.1.

Next, compound 48 was coupled to UMP according to Baisch et al. *Bioorg. Med. Chem.*, 1997, 5, 383-391).

Thus, a solution of D-uridine-5'-monophosphate disodium salt (1.49 g, 4.05 mmol) in H$_2$O (15 mL) was treated with DOWEX 50Wx8 (H$^+$ form) for 30 minutes and filtered. The filtrate was stirred vigorously at rt while tributylamine (0.966 mL, 4.05 mmol) was added dropwise. After 30 minutes of further stirring, the reaction mixture was lyophilized and further dried over P$_2$O$_5$ under vacuum for 5 h.

The resulting tributylammonium uridine-5'-monophosphate was dissolved in dry DMF (25 mL) in an argon atmosphere. Carbonyldiimidazole (1.38 g, 8.51 mmol) was added and the reaction mixture was stirred at r.t. for 30 min. Next, dry MeOH (180 μL) was added and stirred for 15 min to remove the excess CDI. The leftover MeOH was removed under high vacuum for 15 min. Subsequently, compound 48 (2.0 g, 4.86 mmol) was dissolved in dry DMF (25 mL) and added dropwise to the reaction mixture. The reaction was allowed to stir at rt for 2 d before concentration in vacuo. The consumption of the imidazole-UMP intermediate was monitored by MS. Flash chromatography (7:2:1-5:2:1 EtOAc:MeOH:H$_2$O) afforded product 49 (1.08 g, 1.51 mmol, 37%).

$^1$H-NMR (300 MHz, D$_2$O): δ 7.96 (d, J=8.0 Hz, 1H), 5.98-5.94 (m, 2H), 5.81-5.79 (m, 1H), 5.70 (dd, J=7.1, 3.3 Hz, 1H), 5.49 (dd, J=15.2, 2.6 Hz, 1H), 5.30 (ddd, J=18.5, 11.0, 3.2 Hz, 2H), 4.57 (q, J=6.0 Hz, 2H), 4.35-4.16 (m, 9H), 4.07-3.95 (m, 2H), 2.17 (s, 3H), 2.08 (s, 3H), 2.07 (s, 3H). LRMS (ESI−) calcd for C$_{21}$H$_{29}$N$_5$O$_{19}$P$_2$ (M−H$^+$) 716.09. found 716.3.

Compound 49 was deacetylated according to Kiso et al., *Glycoconj. J.*, 2006, 23, 565-573).

Thus, compound 49 (222 mg, 0.309 mmol) was dissolved in H$_2$O (2.5 mL) and triethylamine (2.5 mL) and MeOH (6 mL) were added. The reaction mixture was stirred for 3 h and then concentrated in vacuo to afford crude UDP-2-azido-2-deoxy-D-galactose (50). $^1$H-NMR (300 MHz, D$_2$O): δ 7.99 (d, J=8.2 Hz, 1H), 6.02-5.98 (m, 2H), 5.73 (dd, J=7.4, 3.4 Hz, 1H), 4.42-4.37 (m, 2H), 4.30-4.18 (m, 4H), 4.14-4.04 (m, 2H), 3.80-3.70 (m, 2H), 3.65-3.58 (m, 1H). LRMS (ESI−) calcd for C$_{15}$H$_{23}$N$_5$O$_{16}$P$_2$ (M−H$^+$) 590.05. found 590.2.

Finally, to a solution of compound 50 in H$_2$O:MeOH 1:1 (4 mL) was added Lindlar's catalyst (50 mg). The reaction was stirred under a hydrogen atmosphere for 5 h and filtered over celite. The filter was rinsed with H$_2$O (10 ml) and the filtrate was concentrated in vacuo to afford the UDP-D-galactosamine (UDP-GalNH$_2$, 51) (169 mg, 0.286 mmol, 92% yield over two steps). $^1$H-NMR (300 MHz, D$_2$O): δ 7.93 (d, J=8.1 Hz, 1H), 5.99-5.90 (m, 2H), 5.76-5.69 (m, 1H), 4.39-4.34 (m, 2H), 4.31-4.17 (m, 5H), 4.05-4.01 (m, 1H), 3.94-3.86 (m, 1H), 3.82-3.70 (m, 3H), 3.30-3.16 (m, 1H). LRMS (ESI−) calcd for C$_{15}$H$_{25}$N$_3$O$_{16}$P$_2$ (M−H$^+$) 564.06. found 564.1.

Example 9-15. Synthesis of UDP-GalNAz 52

Azidoacetic acid succinimidyl ester was prepared according to the procedure in Hamilton et al, *Chem. Eur. J.*, 2012, 18, 2361-2365.

UDP-D-galactosamine (51) (82 mg, 0.145 mmol) was dissolved in 0.1 M NaHCO$_3$ (2 mL) and azidoacetic acid succinimidyl ester (86 mg, 0.435 mmol) and DMF (2 mL) were added. The reaction was stirred overnight at r.t. and subsequently concentrated in vacuo. Flash chromatography (7:2:1-5:2:1 EtOAc:MeOH:H$_2$O) afforded UDP-GalNAz (52) (34 mg, 0.052 mmol, 36%).

$^1$H-NMR (300 MHz, D$_2$O): δ 8.73 (d, J=8.1 Hz, 1H), 5.90-5.82 (m, 2H), 5.49 (dd, J=6.9, 3.3 Hz, 1H), 4.29-4.05 (m, 7H), 4.03-3.85 (m, 4H), 3.72-3.61 (m, 2H). LRMS (ESI−) calcd for C$_{17}$H$_{26}$N$_6$O$_{17}$P$_2$ (M−H$^+$) 647.08. found 647.1.

Example 9-16. Synthesis of UDP-GalNAc-yne 53

Pent-4-ynoic acid succinimidyl ester was prepared according to the procedure in Rademann et al., *Angew. Chem. Int. Ed.*, 2012, 51, 9441-9447.

UDP-D-galactosamine (51) (53 mg, 0.094 mmol) was dissolved in 0.1 M NaHCO$_3$ (2 mL) and pent-4-ynoic acid succinimidyl ester (37 mg, 0.188 mmol) and DMF (2 mL) were added. The reaction was stirred overnight at r.t. and concentrated in vacuo. Flash chromatography (7:2:1-5:2:1 EtOAc:MeOH:H$_2$O) afforded UDP-GalNAc-yne (53) (42 mg, 0.065 mmol, 69%).

$^1$H-NMR (300 MHz, D$_2$O): δ 7.78 (d, J=8.2 Hz, 1H), 5.84-5.76 (m, 2H), 5.39 (dd, J=6.8, 3.2 Hz, 1H), 4.22-4.16 (m, 2H), 4.14-3.97 (m, 5H), 3.88-3.85 (m, 1H), 3.81-3.75 (m, 1H), 3.63-3.55 (m, 2H), 2.45-2.28 (m, 5H), 2.19 (t, J=2.4 Hz, 1H).

LRMS (ESI−) calcd for C$_{20}$H$_{29}$N$_3$O$_{17}$P$_2$ (M−H$^+$) 644.09. found 644.1.

Example 9-17. Synthesis of UDP-GalNLev 54

Levulinic acid succinimidyl ester was prepared according to the procedure for pent-4-ynoic acid succinimidyl ester in Rademann et al., *Angew. Chem. Int. Ed.*, 2012, 51, 9441-9447.

$^1$H-NMR (300 MHz, CDCl$_3$): δ 2.81 (s, 4H), 2.77 (s, 4H), 2.14 (s, 3H).

UDP-D-galactosamine (51) (53 mg, 0.094 mmol) was dissolved in 0.1 M NaHCO$_3$ (2 mL) and levulinic acid succinimidyl ester (40 mg, 0.188 mmol) and DMF (2 mL) were added. The reaction was stirred overnight at r.t. and the solvent was removed under reduced pressure. Flash chromatography (7:2:1-5:2:1 EtOAc:MeOH:H$_2$O) afforded UDP-GalNLev (54) (10 mg, 0.015 mmol, 16%).

$^1$H-NMR (300 MHz, D$_2$O): δ 7.78 (d, J=8.4 Hz, 1H), 5.82-5.77 (m, 2H), 5.36 (dd, J=6.8, 3.2 Hz, 1H), 4.22-4.15 (m, 2H), 4.13-3.95 (m, 5H), 3.88-3.84 (m, 1H), 3.82-3.75 (m, 1H), 3.64-3.52 (m, 3H), 2.74-2.61 (m, 2H), 2.47-2.37 (m, 2H), 2.05 (s, 3H). LRMS (ESI−) calcd for C$_{20}$H$_{31}$N$_3$O$_{18}$P$_2$ (M−H$^+$) 662.10. found 662.1.

Example 9-18. Synthesis of BCN-MMAF (56)

To a solution of MMAF.TFA (8.1 mg, 0.0096 mmol) in DMF (0.3 mL) was added Et$_3$N (5 μL, 3.6 mg, 0.036 mmol) and BCN-PEG$_2$-OSu (36) (19 mg, 0.045 mmol). After overnight reaction, the mixture was concentrated. Purification via column chromatography (DCM→MeOH/DCM 1/3)

yielded the desired product. LRMS (HPLC, ESI+) calcd for $C_{55}H_{87}N_6O_{13}$ (M+H$^+$) 1039.63. found 1039.72.

General Protocol for Modification of IgGs

Trimming of IgG Glycans with Endo S

Trimming of IgG glycans was performed using endo S from *Streptococcus pyogenes* (commercially available from Genovis, Lund, Sweden). The IgG (10 mg/mL) was incubated with endo S (40 U/mL) in 25 mM Tris pH 8.0 for approximately 16 hours at 37° C. The deglycosylated IgG was concentrated and washed with 10 mM $MnCl_2$ and 25 mM Tris-HCl pH 8.0 using an Amicon Ultra-0.5, Ultracel-10 Membrane (Millipore).

Mass Spectral Analysis

A solution of 50 µg (modified) IgG, 1 M Tris-HCl pH 8.0, 1 mM EDTA and 30 mM DTT with a total volume of approximately 70 µL was incubated for 20 minutes at 37° C. to reduce the disulfide bridges allowing to analyze both light and heavy chain. If present, azide-functionalities are reduced to amines under these conditions. Reduced samples were washed trice with milliQ using an Amicon Ultra-0.5, Ultracel-10 Membrane (Millipore) and concentrated to 10 µM (modified) IgG. The reduced IgG was analyzed by electrospray ionization time-of-flight (ESI-TOF) on a JEOL AccuTOF. Deconvoluted spectra were obtained using Magtran software.

Figure 15A:
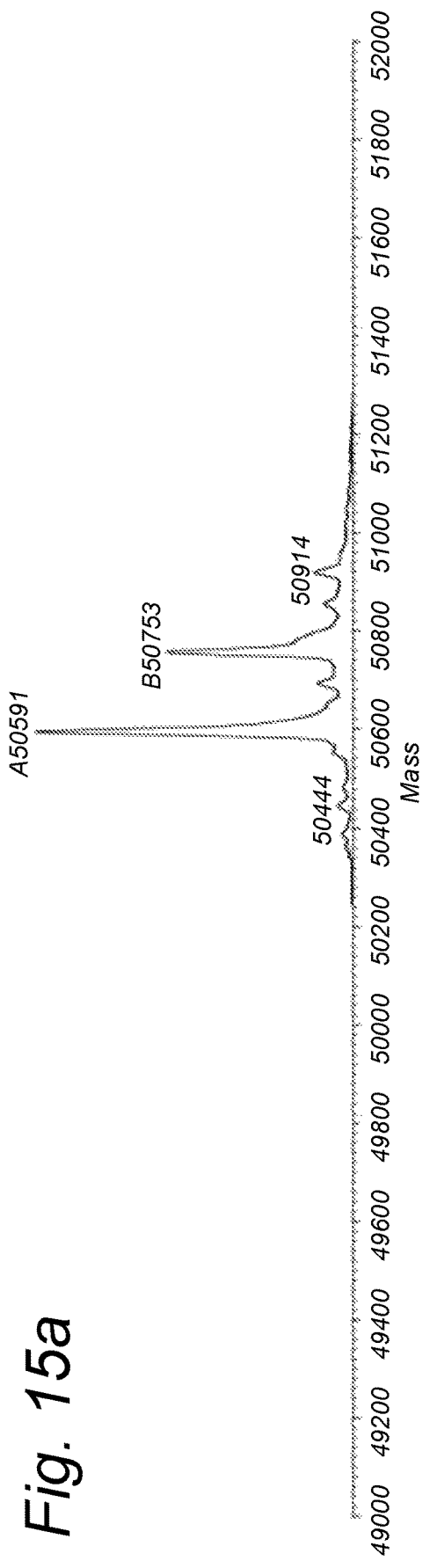
FIG. 15 shows the MS profile of (A) trastuzumab, (B) trastuzumab after trimming with endo S, (C) after galactosyltransferase with UDP-GalNAz 52 and (D) after conjugation with BCN-MMAF 37b.
Figure 15B:
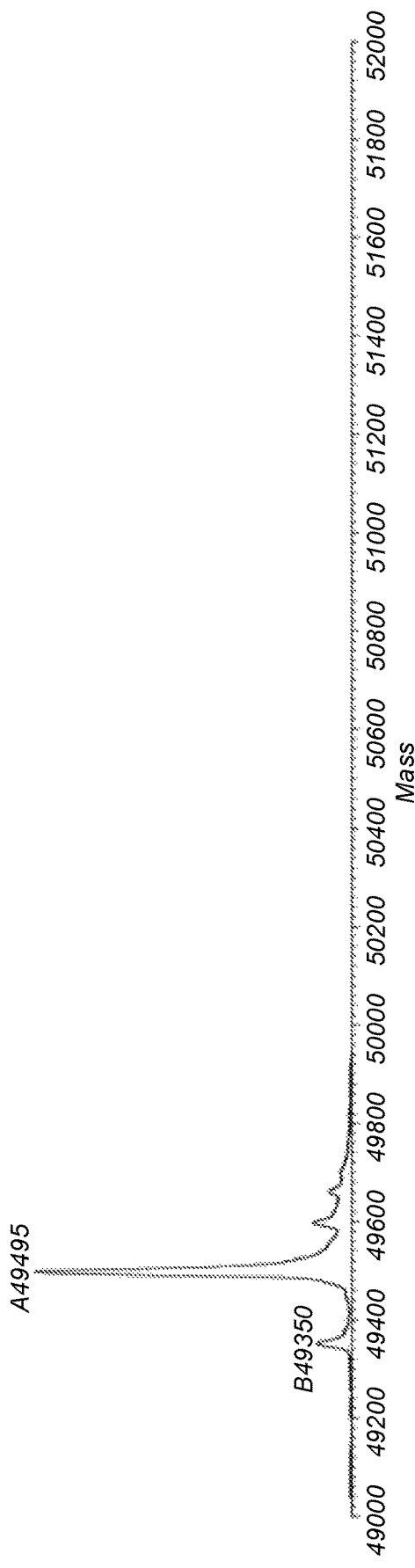

Example 10. Trimming of Trastuzumab (FIG. 15*a*+15*b*)

Trastuzumab was subjected to the trimming protocol above. After deconvolution of peaks, the mass spectrum showed one peak of the light chain and two peaks of the heavy chain. The two peaks of heavy chain belonged to one major product (49496 Da, 90% of total heavy chain), resulting from core GlNAc(Fuc) substituted trastuzumab, and a minor product (49351 Da, ±10% of total heavy chain), resulting from core GlcNac substituted trastuzumab.

Example 11. Trimming of Bevacizumab

Treatment of bevacizumab similar to trastuzumab led to the formation of one major heavy chain product (50062 Da, ±90%) along with a few minor heavy chain products (±10%).

Example 12. Trimming of Cetuximab

Cetuximab differs from trastuzumab in the fact that it contains a second N-glycosylation site at N88. The glycan at N88 is located in the Fab region and has a different constitution from the glycan at N297. Treatment of cetuximab similar to trastuzumab led to the formation of a range of heavy chain products with masses of 51600 Da-52300 Da (major peaks at 51663 Da and 51808 Da), indicating that only one glycan was trimmed by Endo S, presumably at N297.

Example 12-1. Trimming of Rituximab

Treatment of rituximab similar to trastuzumab led to the formation of one major heavy chain product (49408 Da).

Example 12-2. Attempted Trimming of Trastuzumab with Endo H

Trastuzumab was incubated with endoglycosidase H (EndoH) from *Streptomyces picatus* (commercially available from New England BioLabs). Increasing concentrations of endo H (≤115 U/µL) were added to trastuzumab (10 mg/mL) in 50 mM sodium citrate pH 5.5 and incubated for 16 h at 37° C. The mass spectra only showed peaks corresponding to the native glycosylated heavy chain (50589 and 50752 Da corresponding to the G0F and G1F isoforms, respectively), indicating that trastuzumab cannot be trimmed using endo H.

Example 12-3. Attempted Trimming of Trastuzumab with Endo M

Trastuzumab (10 mg/mL) was incubated with increasing concentrations of endo-β-N-acetylglucosaminidase (endo M, ≤231 mU/mL) from *Mucor hiemalis* (commercially available from TCI Europe N.V.) in 50 mM sodium citrate pH 6.0 and incubated for 16 h at 37° C. The mass spectrum showed major peaks corresponding to the native glycosylated heavy chain (50589 and 50752 Da corresponding to the G0F and G1F isoforms, respectively). In addition, a minor product was observed (49347 Da, ±5% of total heavy chain), resulting from the core GlcNac substituted heavy chain. These results show that only trastuzumab glycoforms lacking the core fucose can be trimmed by endo M.

Glycosyltransfer of Galactose Derivative (e.g. Azidosugar) with Gal-T1(Y289L)

Enzymatic introduction of galactose derivative (e.g. azido-containing sugar) onto IgG was effected with a mutant of bovine β(1,4)-galactosyltransferase [β(1,4)-Gal-T1 (Y289L)]. The deglycosylated IgG (prepared as described above, 10 mg/mL) was incubated with a modified UDP-galactose derivative (e.g. an azido-modified sugar-UDP derivative) (0.4 mM) and β(1,4)-Gal-T1(Y289L) (1 mg/mL) in 10 mM $MnCl_2$ and 25 mM Tris-HCl pH 8.0 for 16 hours at 30° C.

The functionalized IgG (e.g. azido-functionalized IgG) was incubated with protein A agarose (40 µL per mg IgG) for 2 hours at 4° C. The protein A agarose was washed three times with PBS and the IgG was eluted with 100 mM glycine-HCl pH 2.7. The eluted IgG was neutralized with 1 M Tris-HCl pH 8.0 and concentrated and washed with PBS using an Amicon Ultra-0.5, Ultracel-10 Membrane (Millipore) to a concentration of 15-20 mg/mL.

Figure 15C:
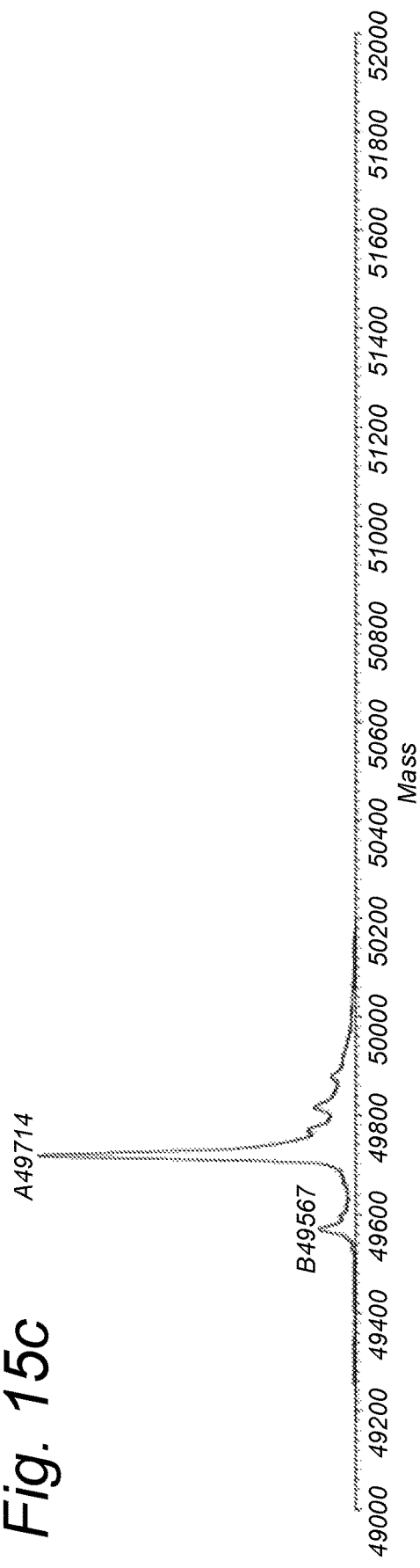
Figure 15D:
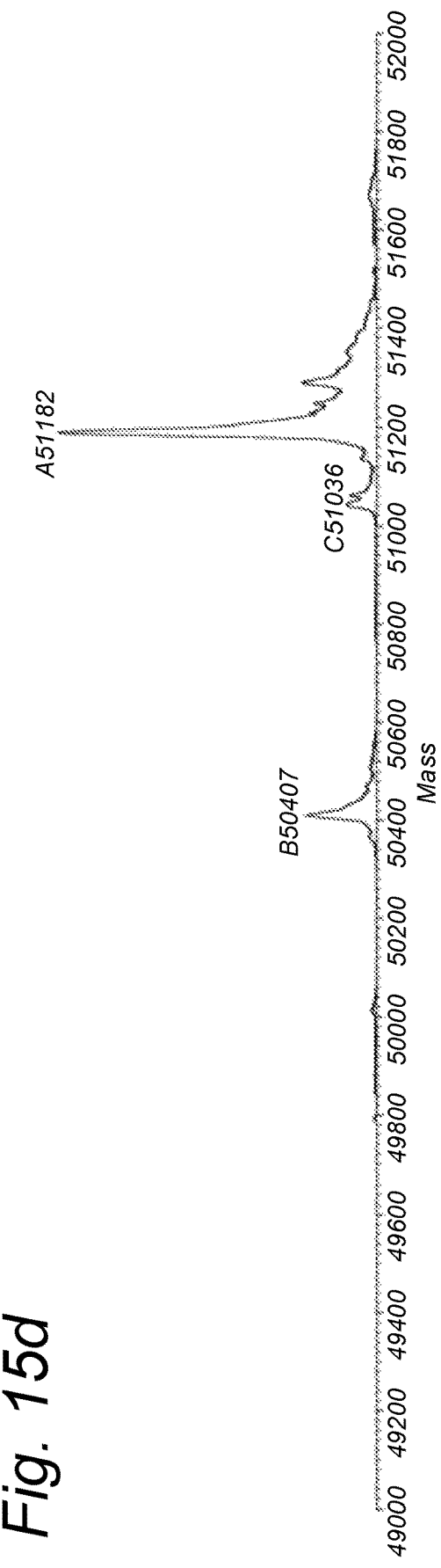
Figure 16A:
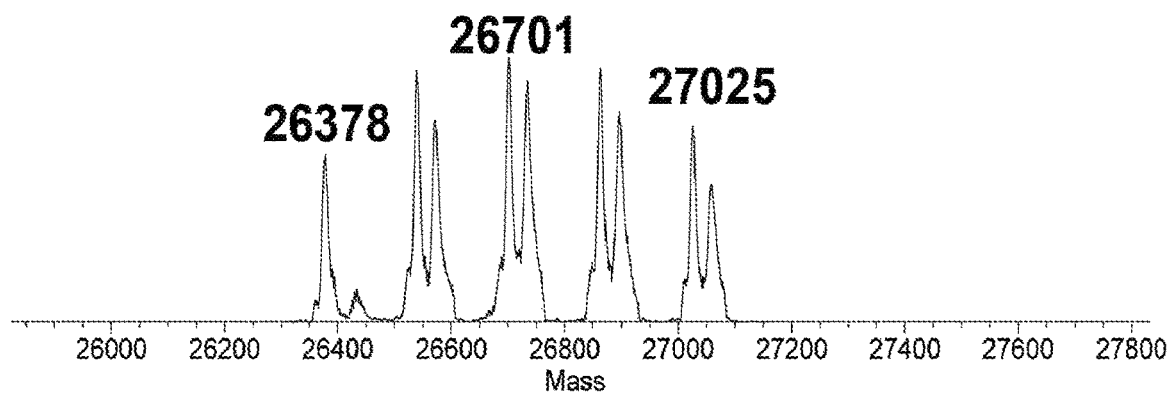
FIG. 16 shows the MS profile of pooled plasma IgG (A), after trimming with endo S (B) and after galactosyltransferase with UDP-GalNAz 52 (C).
Figure 16B:
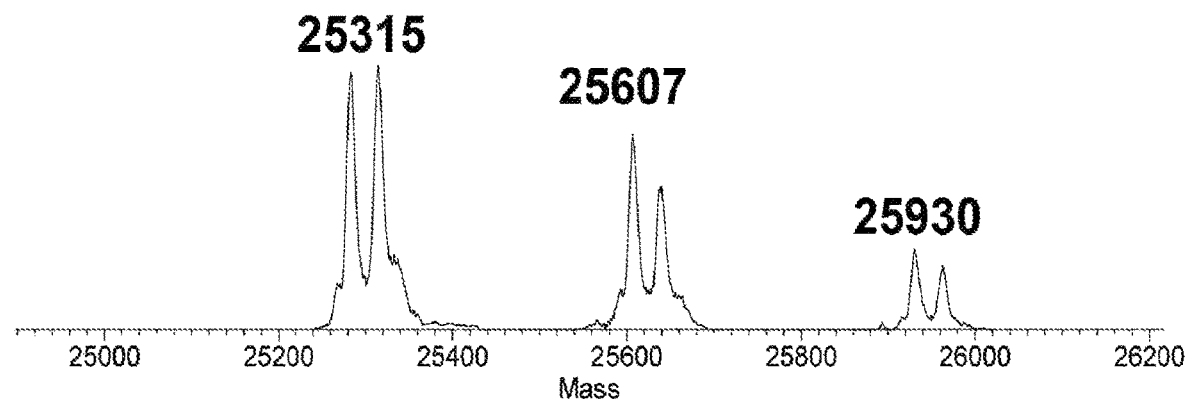
Figure 16C:
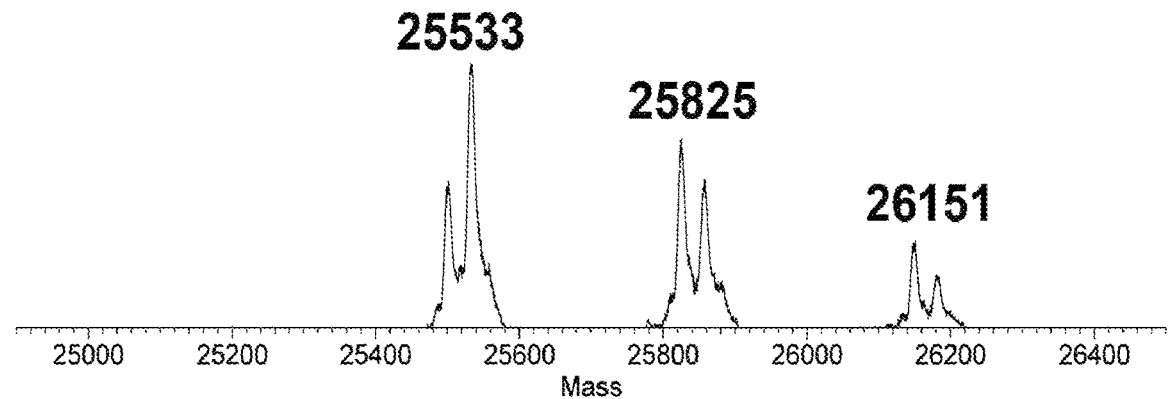

Example 13. Trastuzumab(GalNAz)$_2$ (FIG. 15*c*)

Trastuzumab was subjected to the glycosyltransfer protocol with UDP-N-azidoacetylgalactosamine 52 (UDP-GalNAz). After protein A affinity purification, mass spectral analysis indicated the formation of a one major product of (49713 Da, 90% of total heavy chain), resulting from GalNAz transfer to core GlcNAc(Fuc) substituted trastuzumab, and a minor product (49566 Da, ±10% of total heavy chain), resulting from GalNAz transfer to core GlcNAc substituted trastuzumab.

Example 14. Bevacizumab(GalNAz)$_2$

Bevacizumab (7.5 mg, 10 mg/mL) was trimmed with Endo S according to the general protocol. The trimmed bevacizumab (10 mg/mL) was incubated with UDP-GalNAz 52 (65 µL, 10 mM) and β(1,4)-GalT1(Y289L) (75 µL, 2 mg/mL) in 10 mM $MnCl_2$ and 25 mM Tris-HCl pH 8.0 for 16 hours at 30° C. Purification with ProtA gave the modified bevacizumab (3.2 mg). AccuTOF analysis showed the formation of one major heavy chain product (50282 Da, ±95%).

Example 15. Cetuximab(GalNAz)$_2$

Cetuximab (7.5 mg, 10 mg/mL) was trimmed with endo S according to the general protocol. The trimmed cetuximab (10 mg/mL) was incubated with UDP-GalNAz 52 (65 µL, 10 mM) and β(1,4)-GalT1(Y289L) (75 µL, 2 mg/mL) in 10 mM MnCl$_2$ and 25 mM Tris-HCl pH 8.0 for 16 hours at 30° C. Purification with ProtA gave the modified cetuximab (3.2 mg). AccuTOF analysis showed the formation of two major heavy chain products (51884 Da and 52029 Da), according to trimming of the N297 glycan, but not the Fab glycan.

Example 15-1. Rituximab(GalNAz)$_2$

Rituximab (7.5 mg, 10 mg/mL) was trimmed with Endo S according to the general protocol. The trimmed rituximab (10 mg/mL) was incubated with UDP-GalNAz 52 (65 µL, 10 mM) and β(1,4)-GalT1(Y289L) (75 µL, 2 mg/mL) in 10 mM MnCl$_2$ and 25 mM Tris-HCl pH 8.0 for 16 hours at 30° C. Purification with ProtA gave the modified rituximab (3.2 mg). AccuTOF analysis showed complete conversion to the desired product (mass 49625, expected mass 49627).

Example 15-2. Girentuximab(GalNAz)$_2$

Girentuximab was trimmed using endo S according to the general protocol described above, leading to the formation of one major heavy chain product (49427 Da). The trimmed girentuximab was subsequently incubated with UDP-GalNAz and β(1,4)-Gal-T1(Y289L) as described above, which led to the formation of one major heavy chain product (49643 Da).

Example 15-3. Trastuzumab(GalNAc-yne)$_2$

Trimmed trastuzumab (100 µL, 10 mg/mL, 6.6 nmol), obtained by endo S treatment of trastuzumab according to the general protocol, was incubated with UDP-GalNAc-yne (53) (5 µL, 10 mM) and β(1,4)-Gal-T1(Y289L) (5 µL, 2 mg/mL) in 10 mM MnCl$_2$ and 25 mM Tris-HCl pH 8.0 for 16 hours at 30° C. The crude mixture was purified with ProtA to afford trast-(GalNAc-yne)$_2$ (0.43 mg). AccuTOF analysis showed 90% conversion to the desired product (mass 49735, expected mass 49736), 10% byproduct (mass 50379) was observed.

Example 15-4. Trastuzumab(GalNLev)$_2$

Trimmed trastuzumab (100 µL, 10 mg/mL, 6.6 nmol), obtained by endo S treatment of trastuzumab according to the general protocol, was incubated with UDP-GalNLev (54) (10 µL, 10 mM) and β(1,4)-Gal-T1(Y289L) (7.5 µL, 2 mg/mL) in 10 mM MnCl$_2$ and 25 mM Tris-HCl pH 8.0 for 16 hours at 30° C. The crude mixture was purified with ProtA to give trast-(GalNLev)$_2$ (0.53 mg). AccuTOF analysis showed 95% conversion to the desired product (mass 49753, expected mass 49754), 5% byproduct (mass 50417) was observed.

Trimming of +GalNAz-Transfer to Pooled Plasma IgG

Example 15-5. Mass Spectrometric Analysis of Plasma IgG

To the reaction mixture containing 0.5 mg pooled plasma IgG (Lee Biosolutions, Inc) was added PBS (220 µL) and digestion buffer (250 µL, 0.1 mg/mL papain, 0.02 M cysteine, 0.02 M EDTA in PBS) followed by incubation for 1 h at 37° C. Subsequent protein A slurry (100 µL) was added and the mixture was rotated end-over-end for 1 h. The protein A was washed with PBS (3×1 mL) followed by elution with glycine.HCl buffer (pH 2.7, 0.1 M, 300 The elution buffer was neutralized with Tris-HCl (pH 8.0, 1 M, 80 µL) and subsequent a sample was taken for mass analysis according to the standard protocol (FIG. 14a).

Example 15-6. Trimming of Pooled Plasma IgG

Pooled plasma IgG (170 µL, 14 mg/mL) was trimmed with endo S (16 µL, 20 U/µL) in 98 µL Tris-HCl (25 mM, pH 8.0) for 16 hours at 37° C. Analysis was performed according to the analysis protocol. AccuTOF measurements showed complete conversion.

The above Examples 15-5 and 15-6 are schematically depicted in Scheme 16.

Example 15-7. GalNAz-Transfer to Plasma IgG

The trimmed plasma IgG (46 µL, 10.8 mg/mL, 3.3 nmol) was incubated with UDP-GalNAz 52 (3.3 µL, 10 mM) and β1,4-Gal-T1(Y289L) (2.5 µL, 2 mg/mL) in 10 mM MnCl$_2$ and 25 mM Tris-HCl pH 8.0 for 16 hours at 30° C. Analysis was performed according the analysis protocol plasma IgG and AccuTOF measurements showed complete conversion. Conjugation of Azido-Modified IgG by Cycloaddition with a Cyclooctyne Probe A covalently linked BCN- or DIBAC-functionalized molecule (in DMSO) was diluted in PBS. The purified IgG containing azides (100 µL of 10 mg/mL) was added and the reaction mixture was rotated end-over-end for 12 to 72 hours at 4° C. The resulting IgG conjugate was concentrated and washed with PBS using an Amicon Ultra-0.5, Ultracel-10 Membrane (Millipore) to a final concentration of 10 mg/mL. Conjugation Reactions of Azido-Modified IgG by Strain Promoted Cycloaddition with a Cyclooctyne Probe After protein A purification, the azido-containing IgG (100 µM or 15 mg/mL) was added to 0.01 volume of a 40 mM stock solution of a covalently linked cyclooctyne-functionalized molecule (4 equivalents) in DMSO or DMF, mixed immediately and rotated end-over-end for 12 to 24 hours at room temperature. If required, this procedure was repeated to obtain complete conversion.

The resulting IgG conjugate was concentrated and washed with PBS using an Amicon Ultra-0.5, Ultracel-10 Membrane (Millipore) to a final concentration of 10 mg/mL. In case of ADC's, this step was replaced by purification via size-exclusion chromatography on a Superdex200 column.

Example 16. Conjugation of BCN-Biotin to Trastuzumab(GalNAz)$_2$

BCN-biotin conjugate 25 (2 µL 100 mM in DMSO) was diluted in PBS (98 µL) and 5 µL of this solution was subjected to trastuzumab(GalNAz)$_2$ (5 µL 10 mg/ml in PBS). Washing and concentration, followed by mass spectral analysis indicated the presence of one major product (50294 Da, 90% of total heavy chain) and a minor product (50148 Da, ±10% of total heavy chain).

Example 17. Conjugation of DIBAC-Biotin to Trastuzumab(GalNAz)$_2$

DIBAC-biotin conjugate 30 (2 µL 100 mM in DMSO) was diluted in PBS (98 µL) and 5 µL of this solution was subjected to trastuzumab(GalNAz)$_2$ (5 µL 10 mg/ml in PBS). Washing and concentration, followed by mass spectral analysis indicated the presence of one major product (50247 Da, 90% of total heavy chain) and a minor product (50101 Da, ±10% of total heavy chain).

Example 17-1. Conjugation of DIBAC-vc-PABA-MMAF 41 to Trastuzumab(GalNAz)$_2$ After 1 day according to AccuTOF analysis full conversion. Observed mass 51248, expected mass 51248.

Example 18. Conjugation of BCN-Doxorubicin 28a to Trastuzumab(GalNAz)$_2$

BCN-doxorubicin 28a (4 µL of 50 mM solution in DMSO) was diluted in PBS (896 µL) and subjected to trastuzumab(GalNAz)$_2$ as described in the general procedure. Washing and concentration, followed by mass spectral analysis indicated the presence of one major product (50708 Da, 90% of total heavy chain) and a minor product (50294 Da, ±10% of total heavy chain).

Example 19. Conjugation of BCN-Doxorubicin 35 to Trastuzumab(GalNAz)$_2$

BCN-doxorubicin 35 (4 µL 50 mM in DMSO) was diluted in PBS (896 µL) and subjected to trastuzumab(GalNAz)$_2$ as described in the general procedure. Washing and concentration, followed by mass spectral analysis indicated the presence of the conjugate of trastuzumab(GalNAz)$_2$ and BCN-doxorubicin 35 (51114 Da).

Example 20. Conjugation of BCN-PEG$_8$-Doxorubicin 28b to Trastuzumab(GalNAz)$_2$ Incubation of BCN-PEG$_8$-doxorubicin (400 µM, 4 eq) with trastuzumab(GalNAz)$_2$ (100 µM) in PBS for 16 hrs led to a complete conversion into trastuzumab(PEG$_8$-doxorubicin)$_2$ (heavy chain products between 50467 and 51134 Da with major peak of 50881 Da corresponding to heavy chain with core GalNAzGlcNac(Fuc) conjugated to BCN-PEG$_8$-doxorubicin).

Example 21. Conjugation of BCN-vc-PABA-Doxorubicin 33 to Trastuzumab(GalNAz)$_2$ BCN-doxorubicin 33 (4 µL of 50 mM solution in DMSO) was diluted in PBS (896 µL) and subjected to trastuzumab (GalNAz)$_2$ as described in the general procedure. Washing and concentration, followed by mass spectral analysis indicated the presence of the conjugate of trastuzumab(GalNAz)$_2$ and BCN-vc-PABA-doxorubicin 33 (51114 Da).

Example 22. Conjugation of BCN-vc-PABA-MMAE 37a to Trastuzumab(GalNAz)$_2$

Incubation of BCN-vc-PABA-MMAE 37a (125 µM, 5 eq) with trastuzumab(GalNAz)$_2$ (25 µM) in PBS for 16 hrs led to a complete conversion into trastuzumab(vc-PABA-MMAE)$_2$ (heavy chain products between 51137 and 51600 Da with major peak of 51283 Da corresponding to heavy chain with core GalNAzGlcNac(Fuc) conjugated to BCN-vc-MMAE, ±95% of total heavy chain, and a minor peak at 50520 Da due to fragmentation of the PABA linker during mass spectrometry, ±5% of total heavy chain).

Example 23. Conjugation of BCN-Vc-PABA-MMAF 37b to Trastuzumab(GalNAz)$_2$

Incubation of BCN-vc-PABA-MMAF 37b (600 µM, 4+2 eq) with trastuzumab(GalNAz)$_2$ (100 µM) in PBS for approximately 16 hrs led to a complete conversion into trastuzumab(vc-PABA-MMAF)$_2$ (heavy chain products between 51032 and 51500 Da with major peak of 51181 Da corresponding to heavy chain with core GalNazGlcNac (Fuc) conjugated to BCN-vc-PABA-MMAF, ±95% of total heavy chain, and a minor peak at 50407 Da due to fragmentation of the PABA linker during mass spectrometry, ±5% of total heavy chain).

Example 24. Conjugation of BCN-MMAF 38 to Trastuzumab(GalNAz)$_2$

Trastuzumab(MMAF)$_2$:
Incubation of BCN-MMAF 38 with trastuzumab(GalNAz)$_2$ (100 µM) in PBS for approximately 16 hrs led to a complete conversion into Trastuzumab(MMAF)$_2$ (heavy chain products between 50636 and 51100 Da with major peak of 50783 Da corresponding to heavy chain with core GalNazGlcNac(Fuc) conjugated to BCN-MMAF).

Example 24-2. Conjugation of BCN-MMAF 57 to Trastuzumab(GalNAz)$_2$

Figure 10A:
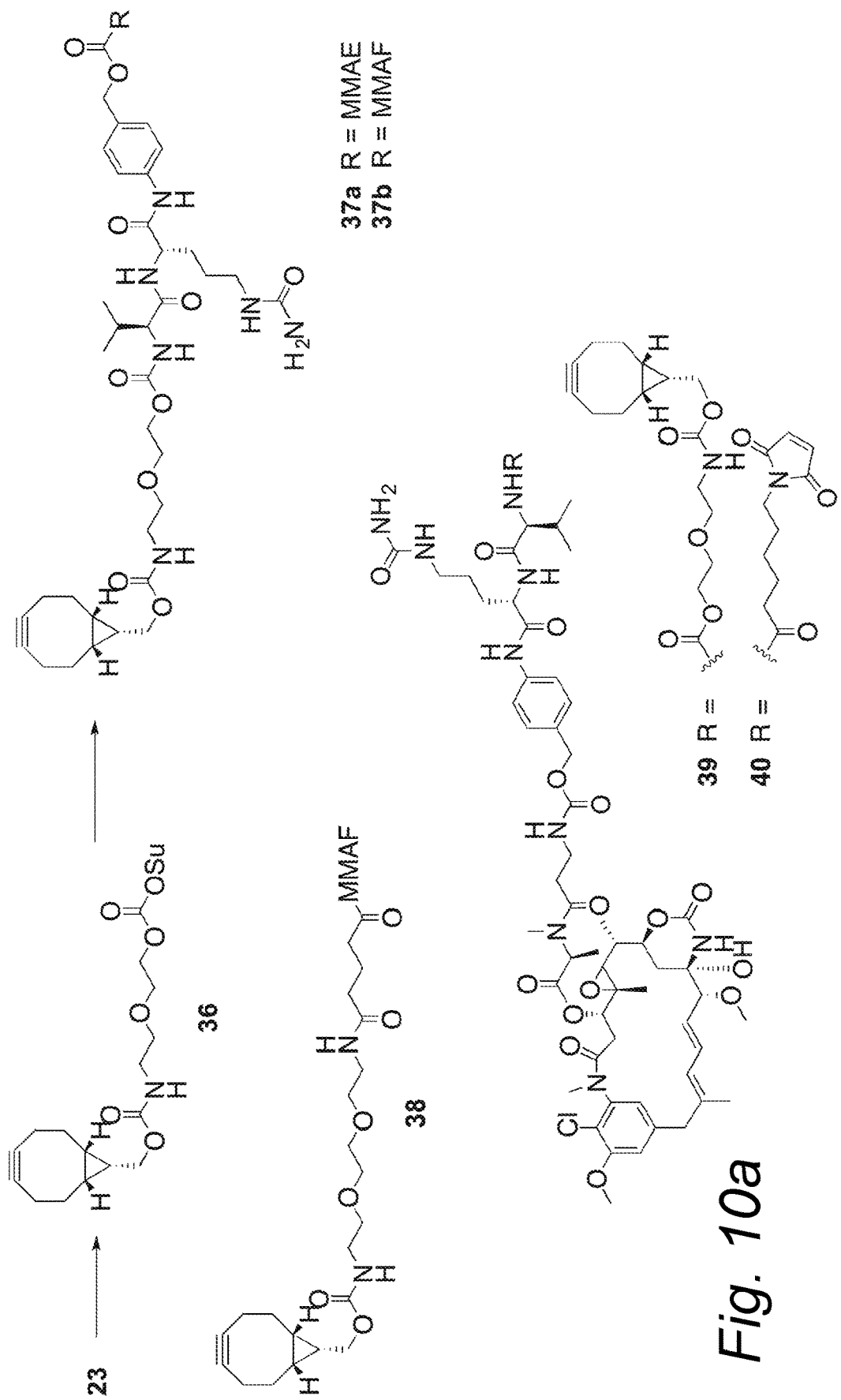
FIG. 10a shows the reaction scheme for the synthesis of cleavable BCN-conjugates to vc-PABA-MMAE (37a), vc-PABA-MMAF (37b), non-cleavable BCN-MMAF conjugate (38), cleavable BCN-vc-PABA-maytansinoid conjugate (38) and maleimide-vc-PABA-maytansinoid conjugate (40).
Figure 12:
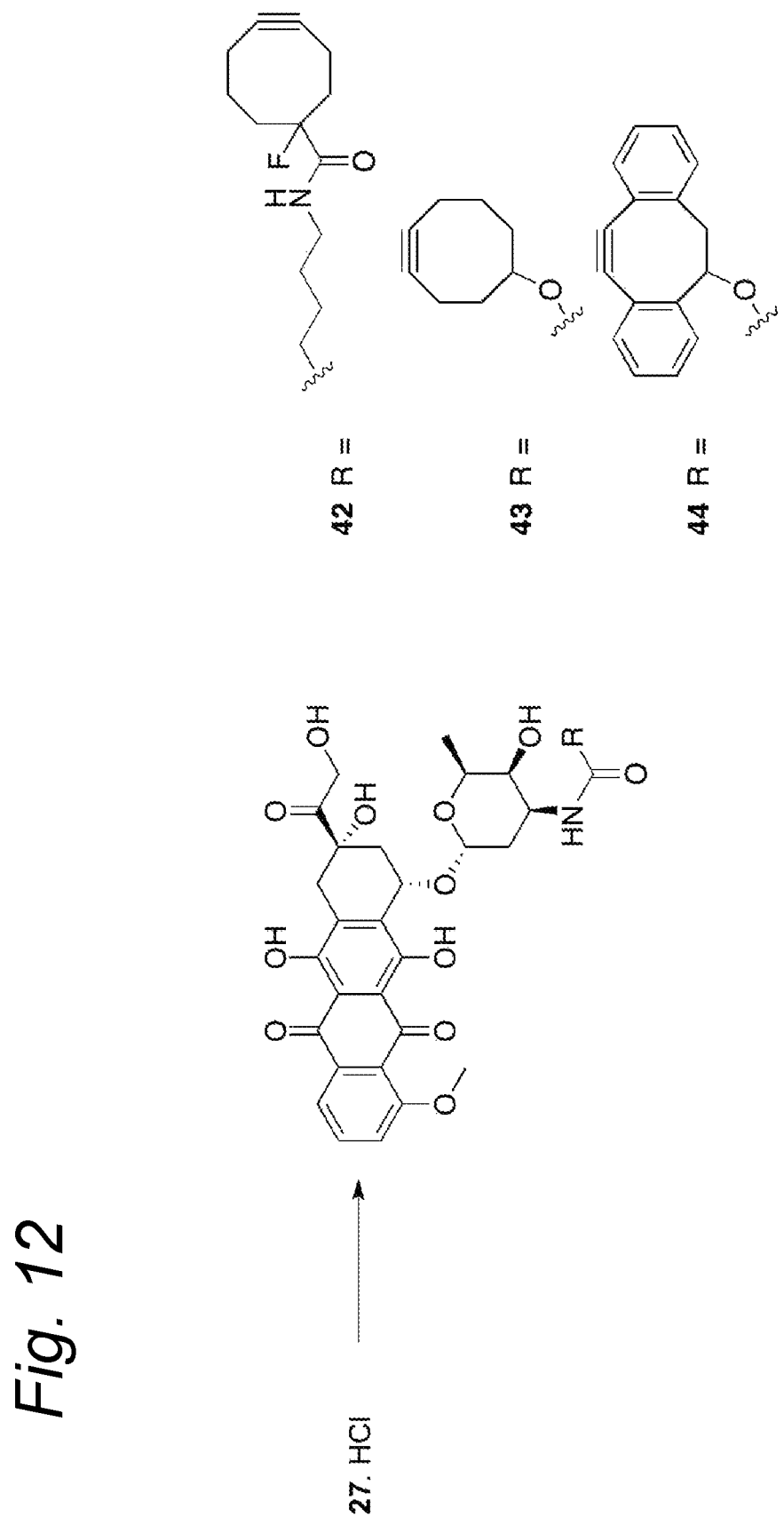
FIG. 12 shows the reaction scheme for the synthesis of three cyclooctyne-doxorubicin conjugates 42-44.

Trastuzumab(MMAF)$_2$:
Incubation of BCN-MMAF (57, FIG. 10b) with trastuzumab(GalNAz)$_2$ (100 µM) in PBS for approximately 16 hrs led to a complete conversion into Trastuzumab(MMAF)$_2$ (heavy chain products between 50636 and 51100 Da with major peak of 50783 Da corresponding to heavy chain with core GalNAzGlcNAc(Fuc) conjugated to BCN-MMAF 57).

Example 25. Conjugation of BCN-vc-PABA-Maytansinoid 39 to Trastuzumab(GalNAz)$_2$ Incubation of BCN-vc-PABA-maytansinoid (39) (800 µM, 2×4 eq) with trastuzumab(GalNAz)$_2$ (100 µM) in PBS for approximately 40 hrs led to a complete conversion into trastuzumab(vc-PABA-maytansinoid)$_2$ (heavy chain products between 50781 and 51600 Da with major peak of 51172 Da corresponding to heavy chain with core GalNAzGlcNac (Fuc) conjugated to BCN-vc-PABA-maytansinoid, ±95% of total heavy chain).

Conjugation of Cyclooctyne-Doxorubicin Conjugates 42-44 to Trastuzumab(GalNAz)$_2$ by Strain Promoted Cycloaddition To a solution of trastuzumab-(GalNAz)$_2$ (7.5 µL, 20 mg/ml, 1 nmol) in PBS was added a solution of cyclooctyne (2.5 µL, 2.4 mM 5% DMF in MiliQ, 6 nmol). The reaction was rotated end-over-end followed by AccuTOF analysis.

Example 26. Conjugation of MCFO-Doxorubicin 42 to Trast(GalNAz)$_2$

After 5 days according to AccuTOF analysis 80% conversion. Observed mass 50548, expected mass 50550.

Example 27. Conjugation of DIBO-Doxorubicin 43 to Trast(GalNAz)$_2$

After 5 days according to AccuTOF analysis 30% conversion. Observed mass 50530, expected mass 50544.

Example 28. Conjugation of Cyclooctyne-Doxorubicin 44 to Trast(GalNAz)$_2$

After 5 days according to AccuTOF analysis 50% conversion. Observed mass 50434, expected mass 50449.

Example 29. CuAAC of Trastuzumab-(N$_3$)$_2$ with Alkyne-Biotin 45

Figure 17:
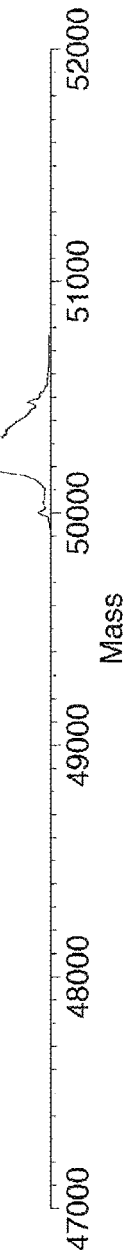
FIG. 17 shows the MS profile of endo S-trimmed trastuzumab, then galactosyltransferase with UDP-GalNAz 52 and finally by copper-catalyzed conjugation with alkyne-biotin 45.

To a solution of trast-(GalNAz)$_2$ (10 µL, 9.6 mg/ml, 0.64 nmol) (derived from 52) in PBS was added a solution of biotin-alkyne (45, 1 µL, 10 mM, 10 nmol) and a stock premix (1 µL, 10 mM CuSO$_4$, 10 mM sodium ascorbate, 10 mM tris((1-((O-ethyl)carboxymethyl)-(1,2,3-triazole-4-yl)) methylamine in 20% MeCN in miliQ). The reaction was rotated end-over-end overnight, after which time AccuTOF analysis showed complete formation of the desired product (observed mass 50195), as indicated in FIG. 17.

Example 30. CuAAC of Trastuzumab-Yne$_2$ with Azido-Biotin 46

Figure 18A:
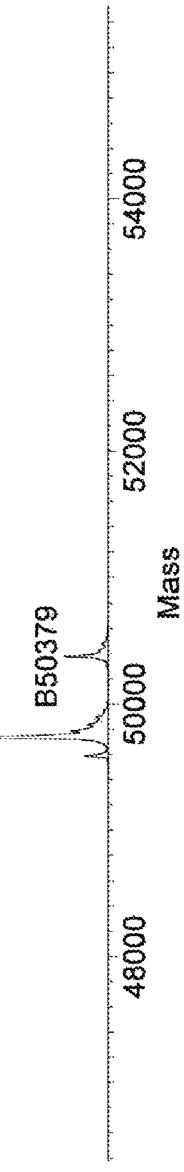
FIG. 18 shows the MS profile of endo S-trimmed trastuzumab, (A) after galactosyltransferase with UDP-GalNAcyne 53 and (B) after copper-catalyzed conjugation with azido-biotin 46, leading to 50% conversion.
Figure 18B:
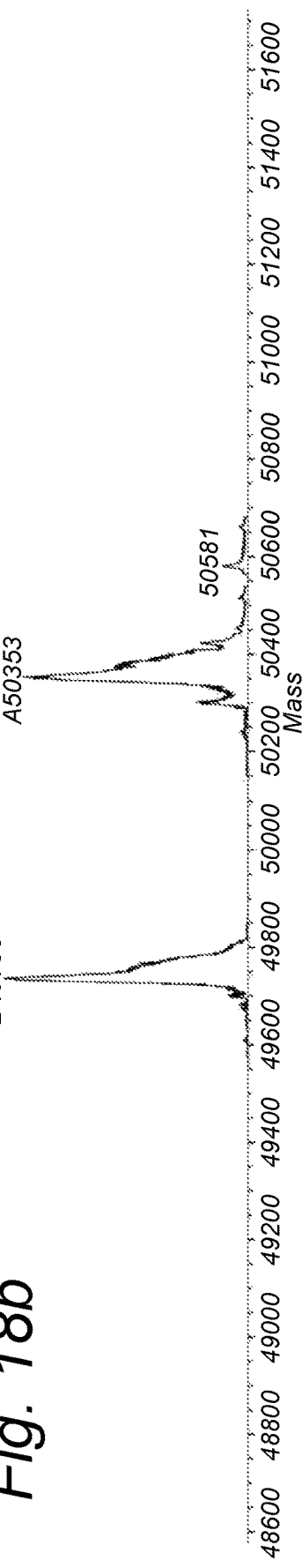
Figure 19A:
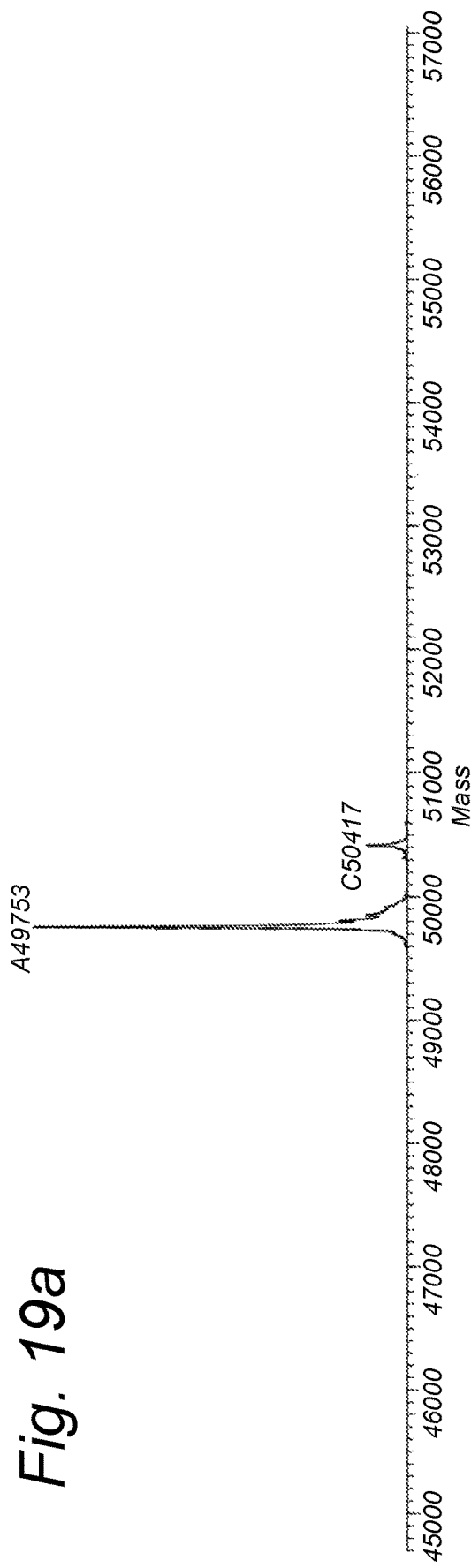
FIG. 19 shows the MS profile of endo S-trimmed trastuzumab, (A) after galactosyltransferase with UDP-GalNLev 55 and (B) after oxime conjugation with hydroxylamine-biotin 47.
Figure 19B:
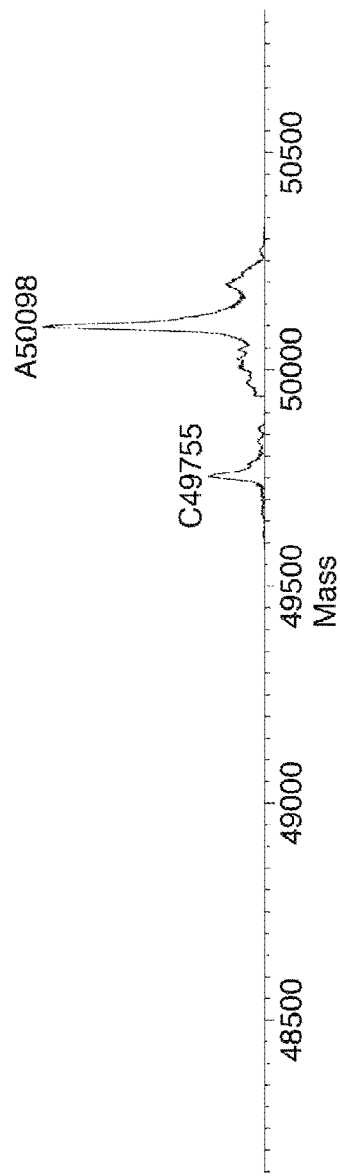
Figure 20:
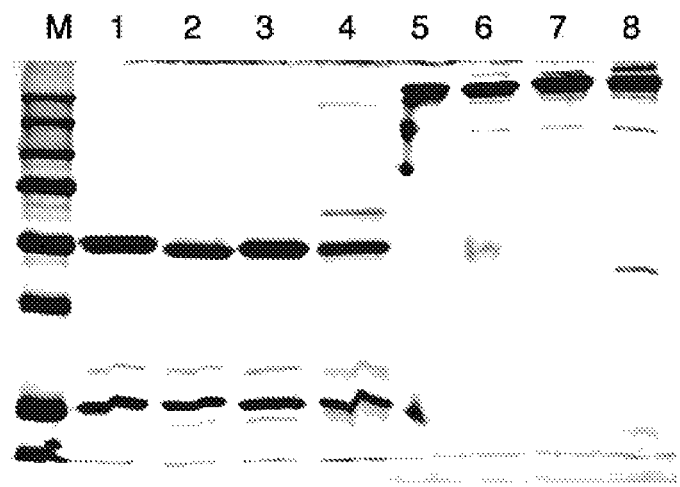
FIG. 20 shows the SDS-PAGE under reducing conditions (lane 1-4) or non-reducing conditions (lane 5-8) of trastuzumab (lane 1 and 5), trastuzumab after trimming and galactosyltransferase with UDP-GalNAz 52 (lane 2 and 6), trastuzumab conjugate obtained by treatment of trast(GalNAz)$_2$ with BCN-biotin 25 (lane 3 and 7) and trastuzumab conjugate obtained by treatment of trast(GalNAz)$_2$ with alkyne-biotin 45 upon Cu(I)-catalyzed click reaction (lane 4 and 8). Several bands in lane 4 and 8 indicate the formation of covalent and/or reduced fragments formed, as well as aggregation, resulting from the copper-catalyzed click conjugation, which are all absent from the strain-promoted conjugation in lane 3 and 7.
Figure 21:
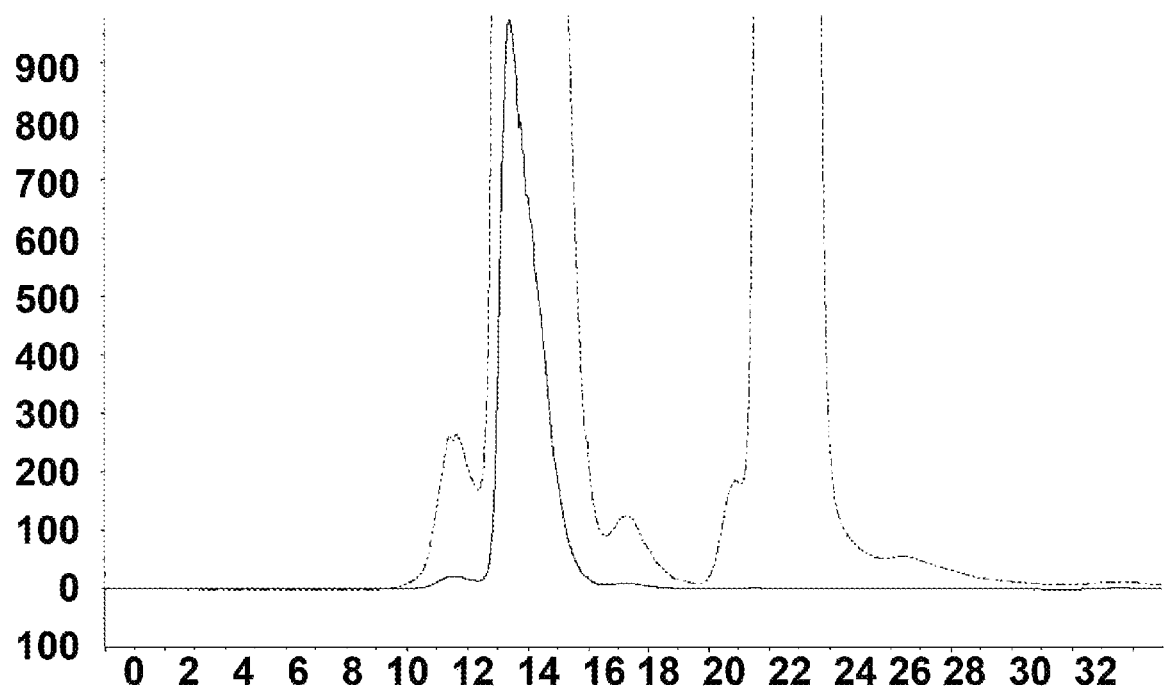
FIG. 21 shows the size-exclusion chromatogram of trastuzumab(MMAF)$_2$ conjugate derived from trastuzumab (GalNAz)$_2$ and BCN-MMAF 37b.
Figure 22:
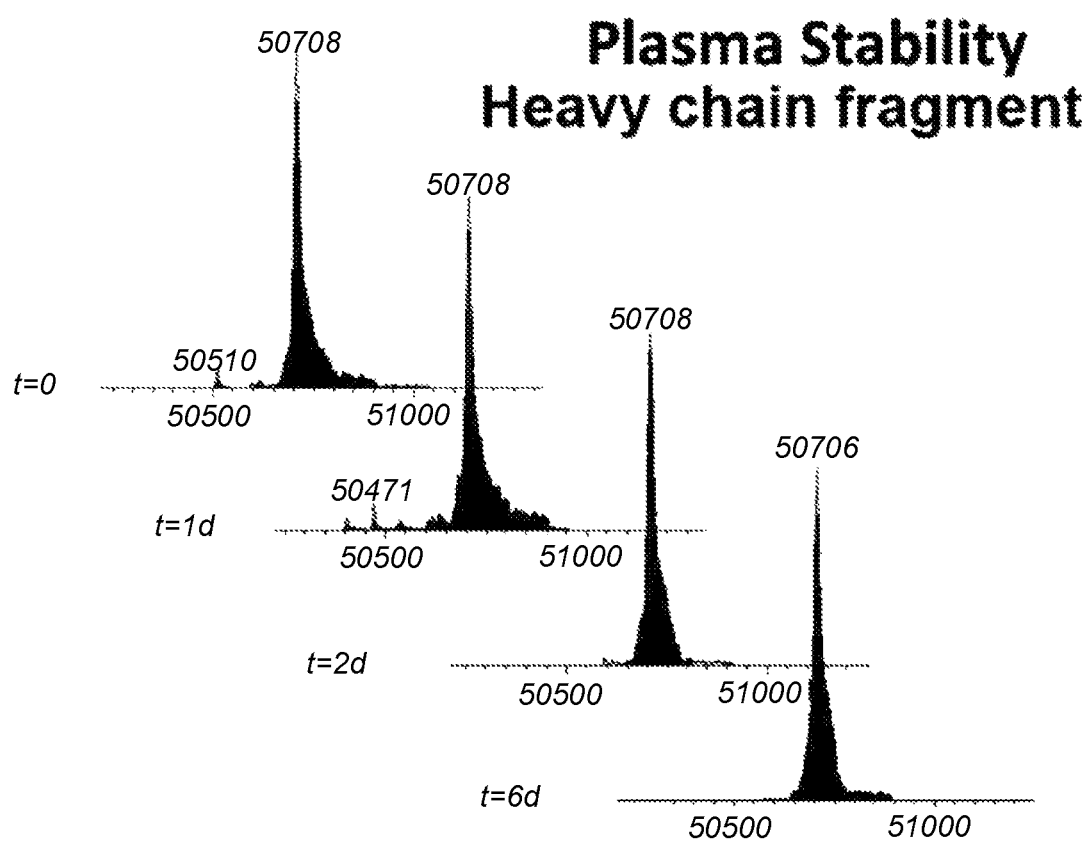
FIG. 22 shows the time-dependent MS profile of trastuzumab(doxorubicin)$_2$ derived from 28a, in IgG-depleted human plasma.
Figure 23:
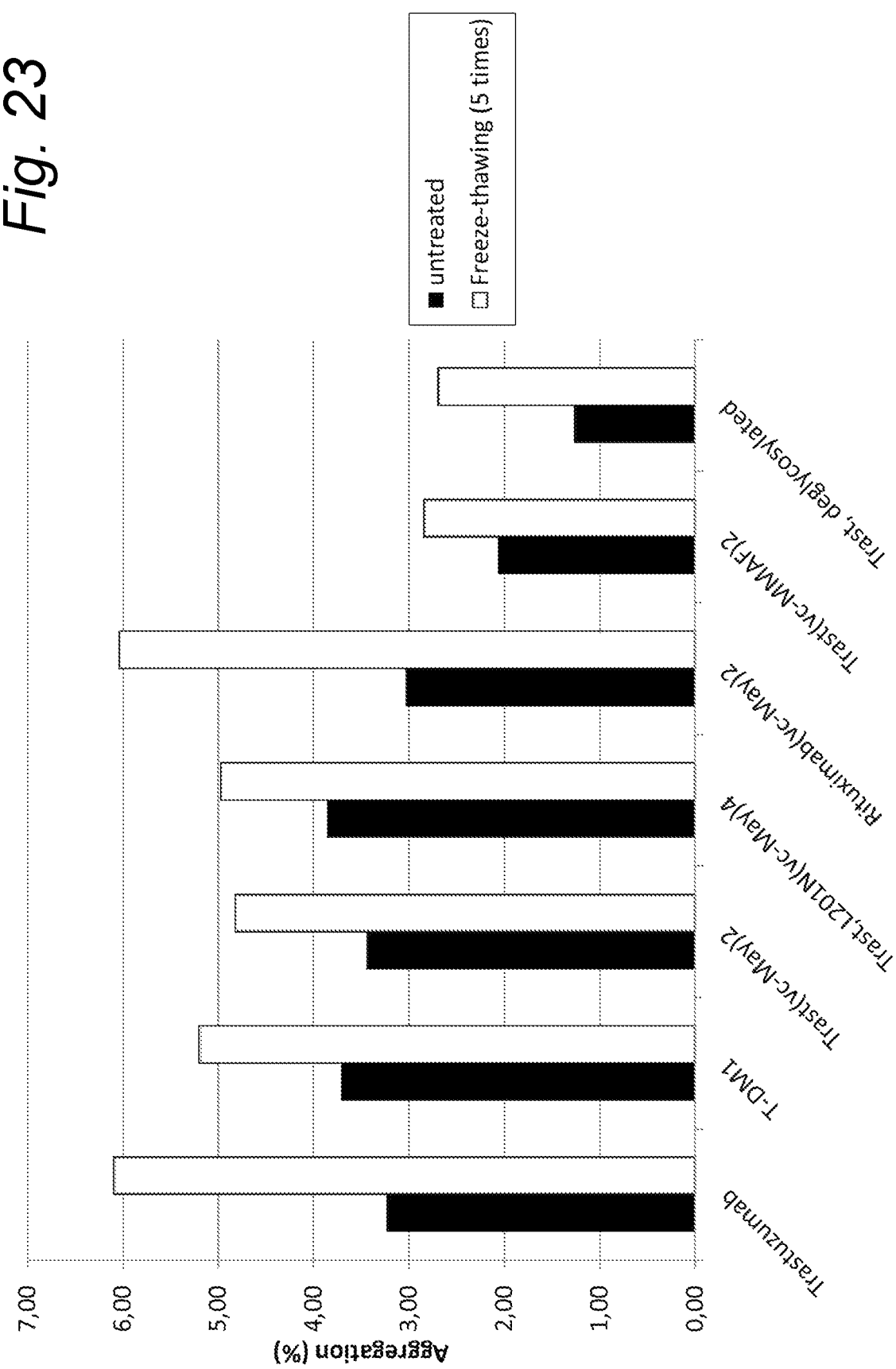
FIG. 23 shows the aggregation level of different mAbs or ADCs untreated or upon 5 freeze-thawing cycles.

To a solution of trast-(GalNAc-yne)$_2$ derived from 53 (10 µL, 9.6 mg/ml, 0.64 nmol) in PBS was added a solution of biotin-N$_3$ 46 (1 µL, 10 mM, 10 nmol) and a stock premix (1 µL, 10 mM CuSO$_4$, 10 mM sodium ascorbate, 10 mM tris((1(O-ethyl)carboxymethyl)-(1,2,3-triazole-4-yl))methylamine in 20% MeCN in miliQ). The reaction was rotated end-over-end overnight and subsequent AccuTOF analysis showed 50% conversion (mass 50353, expected mass 50351), as indicated in FIG. 18.

Example 31. Conjugation of Maleimide-vc-PABA-Maytansinoid 40 to Trastuzumab(N297C)

Trastuzumab(N297C) (4 mg, 10 mg/mL) was incubated with DTT (10 eq) in PBS pH 7.4 for 2 hours at 22° C. The excess of DTT was removed by spin-filter purification and the reduced IgG (10 mg/mL) was incubated with dehydroascorbic acid (20 eq) for 3 hours at 22° C. maleimide-vc-PABA-maytansinoid 40 (3 eq) was added and the reaction mixture was incubated at room temperature for 1 hour, after which the excess of maleimide-vc-PABA-maytansinoid 40 was removed by spinfilter purification. AccuTOF analysis showed the formation of three heavy chain products, which correspond to the unmodified heavy chain (49133 Da, ±10% of total heavy chain), the heavy chain conjugated to 1 maytansinoid (50454 Da, ±85% of total heavy chain) and the heavy chain conjugated to 2 maytansinoids (50774 Da, ±5% of total heavy chain). No conjugation to the light chain was detected.

Example 32. In Vitro Plasma Stability Assay

Human plasma (prepared using heparin) was centrifuged at 200 g for 10 minutes at 4° C. and the supernatant was incubated with protein A agarose (Kem-En-Tec) for 1 hour at 4° C. to deplete for IgG. The depleted plasma was filter sterilized using a 0.22 µm filter (Whatman). The trastuzumab-doxorubicin conjugate derived from 28a was added to the sterile human plasma to a final concentration of 100 µg/ml and incubated at 37° C. in a CO$_2$ incubator to keep plasma pH levels close to the physiological pH of 7.2. Samples were taken at 0, 24, 48 and 144 hours and stored at −80° C. The trastuzumab conjugate was purified with protein A agarose followed by MS analysis. Human plasma samples were incubated with protein A agarose for 1 hour at 4° C., washed three times with phosphate-buffered saline (PBS) and the trastuzumab conjugate was eluted with 100 mM glycine-HCl pH 2.7 followed by neutralization with 1 M Tris-HCl pH 8.0. MS analysis showed that the peak corresponding to the trastuzumab-doxorubicin conjugate (50708 Da) did not decrease in time. In addition, no peaks corresponding to degradation products could be detected, proving that the conjugate is stable for at least 144 hours in human plasma.

Example 33. In Vitro Efficacy

SK-Br-3 (Her2+), SK-OV-3 (Her2+) and MDA-MB-231 (Her2−) cells were plated in 96-well plates (5000 cells/well) in RPMI 1640 GlutaMAX (Invitrogen) supplemented with 10% fetal calf serum (FCS) (Invitrogen, 200 µL/well) and incubated overnight at 37° C. and 5% CO$_2$. A three-fold dilution series (ranging from ±0.002 to 100 nM) of the sterile-filtered compounds was prepared in RPMI 1640 GlutaMAX supplemented with 10% FCS. After removal of the culture medium, the concentration series were added in quadruplo and incubated for three days at 37° C. and 5% CO$_2$. The culture medium was replaced by 0.01 mg/mL resazurin (Sigma Aldrich) in RPMI 1640 GlutaMAX supplemented with 10% FCS. After 4 to 6 hours at 37° C. and 5% CO$_2$ fluorescence was detected with a fluorescence plate reader (Tecan Infinite 200) at 540 nm excitation and 590 nm emission. The relative fluorescent units (RFU) were normalized to cell viability percentage by setting wells without cells at 0% viability and wells with lowest dose of compound at 100% viability. For each conditions the average cell viability percentage±sem is shown.

The in vitro cytotoxicity of trastuzumab-(vc-PABA-MMAE)$_2$ (derived from 37a), trastuzumab-(vc-PABA-MMAF)$_2$ (derived from 37b), trastuzumab-(vc-PABA-maytansinoid)$_2$ (derived from 39), trastuzumab-(maytansinoid)$_2$ and trastuzumab(N297C)-(vc-PABA-maytansinoid)$_2$ (derived from 40) were compared to T-DM1 as a positive control and trastuzumab and rituximab-(vc-PABA-maytansinoid)$_2$ as negative controls. All trastuzumab-based ADCs affect the viability of the Her2-positive cell lines SK-Br-3 and SK-OV-3, but not of the Her2-negative cell line MDA-MB-231, which shows that these ADCs specifically target Her2 positive cells. In the Her2 negative cell line MDA-MB-231, only T-DM1 shows a slight decrease in cell viability at the highest concentration (100 nM).

Example 34. DTPA Conjugation, Radio-Labeling and Determination of IRE

Trastuzumab(MMAF)$_2$ (derived from conjugation of trast (GalNAz)$_2$ and 37b) and trastuzumab(maytansinoid)$_2$ (derived from conjugation of trast(GalNAz)$_2$ and 39), deglycosylated trastuzumab (obtained from treatment of trastuzumab and endo S) and native trastuzumab were conjugated with isothiocyanate-DTPA (Macrocyclics, Houston, Tex.) and labeled with $^{111}$In (Covidien, Petten). For the animal experiments, all constructs were labeled at specific activity between 2.7 and 3.4 MBq/µg.

Example 35. PK/Biodistribution Studies

BALB/c nude mice (n=15) were inoculated subcutaneously with 5×106 SK-OV-3 cells (injection volume: 200 μl) in the right flank. At 14 days after tumor induction, groups of five mice were injected i.v. with 15-20 MBq of $^{111}$In-labeled antibody, labeled at a protein dose of 25 μg. To assess the in vivo stability and pharmacokinetics of the conjugates, 50 μl blood samples were taken via submandibular bleeding at 0.5, 1, 30 min, 1, 2 and 4 hours, and 1, 2, 5, 7, 9, 13, 16 and 21 days after injection of the radiolabeled antibody preparations.

Example 36. Biodistribution

One week after injection (3 d p.i.) mice were euthanized and dissected to determine the biodistribution of the radiolabeling in relevant tissues. Tissue distribution of trastuzumab(MMAF)$_2$ (derived from 37b), trastuzumab(maytansinoid)$_2$ (derived from 39) and deglycosylated trastuzumab is comparable with that of the native trastuzumab.

Example 37. In Vivo Efficacy

Female SHO mice (Crl: SHO-Prkdcscid Hrhr, 6- to 9-week-old at the beginning of the experimental phase, obtained from Charles River Laboratories, L'Arbresles, France) were anaesthetized with ketamine/xylazine, the skin was aseptized with a chlorhexidine solution, incised at the level of the interscapular region, a 20 mm$^3$ tumor fragment (HBCx-13B breast cancer patient-derived xenograft model) was placed in the subcutaneous tissue and the skin was closed with clips. When the tumor volume was in the range of 60 to 200 mm$^3$, groups of four mice were injected i.v. with either vehicle, trastuzumab-(vc-PABA-maytansinoid)$_2$ (derived from 39, at 3 mg/kg and 9 mg/kg), trastuzumab-(vc-PABA-MMAF)$_2$ (derived from 37b, at 3 mg/kg and 9 mg/kg), and T-DM1 (9 mg/kg).

Detailed Mass Spectrometric Analysis of Trastuzumab and Derivatives

Native trastuzumab, trastuzumab(GalNAz)$_2$, and biotin conjugates prepared from trastuzumab(GalNAz)$_2$ by copper-catalyzed click chemistry (conjugation with 46 according to the protocol described in example 29) or by strain-promoted click chemistry (conjugation with 25 as described in example 16) were subjected to detailed mass spectral analysis of intact protein species (nanoLC-MS) using nanoLC coupled to ultra high resolution QTOF MS (maXis 4G).

Example 38. Intact Protein Analysis

Sample Preparation

Protein reduction was performed for 30 minutes in 10 mM DTT at 56° C. Samples were diluted 1:1 in 2% formic acid prior to analysis.

Liquid Chromatography-Mass Spectrometry

Protein separations were performed using a UHPLC nanoflow liquid chromatography (Bruker Daltonics nano advance) coupled online to an ultra high resolution quadrupole time-of-flight mass spectrometer (Bruker Daltonics maXis 4G ETD) via an axial desolvation vacuum assisted electrospray source (Bruker Daltonics captive sprayer). Proteins were loaded on the trap column (Dionex PepSwift, 0.2×5 mm) in 3 minutes at a flowrate of 5000 nL/min using 0.1% formic acid. Proteins were separated on a 0.2×150 mm monolithic particle column (Michrom 8 μm 4000 Å PLRP-S) at 50° C. using a linear gradient of 20 to 50% acetonitrile and 0.1% formic acid at a flowrate of 1000 nl/min. Desolvation and ionization of peptides eluting from the column was performed using 6 L/min nitrogen gas at 180° C. and 1600 V capillary voltage. The mass spectrometer was calibrated externally using Agilent tuning mix (G1969-85000) and used lockmass calibration at 1221.9906 m/z (Agilent G1982-85001). The mass spectrometer was programmed to acquired spectra in the range of 500-4200 m/z at 1 Hz with the following settings: 400 Vpp Funnel RF, 10 eV isCID, 400 Vpp Multipole RF, 8 eV Quadrupole ion energy, 510 m/z Low mass, 10 eV Collision cell energy, 3500 Vpp Collision RF, 110 μs Transfer time, 450 Vpp Ion cooler RF and 18 μs Pre pulse storage.

Data Processing

All data were processed in Data Analysis software. After lock mass calibration, both the light- and heavy-chain MS spectra were averaged over each chromatographic peak, respectively. Averaged spectra were deconvoluted using the maximum entropy algorithm in combination with the SNAP peak picking algorithm for the light chain spectrum or Sum peak picking for the heavy chain spectrum.

Example 39. Proteolytical Peptide Analysis

Sample Preparation

From each sample, five microgram of protein was subjected to in-solution tryptic digestion. Briefly, reduction was performed in 10 mM DTT for 30 minutes at 56° C. Alkylation of reduced cysteines (carbamidomethylation) was performed using 50 mM chloroacetamide. Protein digestion was first performed by addition of 0.5 μg LysC peptidase and incubation for 3 hours at 37° C. Next, 800 ng trypsin was added to the sample and incubated O/N at 37° C. Resulting proteolytical peptides were concentrated and desalted using stop-and-go elution tips.

Liquid Chromatography—Tandem Mass Spectrometry

Peptide separations were performed using a UHPLC nanoflow liquid chromatograph (Bruker Daltonics nano advance) coupled online to a high capacity ion trap (Bruker Daltonics amaZon speed ETD) via an axial desolvation vacuum assisted electrospray source (Bruker Daltonics captive sprayer). Peptides were loaded onto the trap column (Dionex PepSwift, 0.2×5 mm) in 3 minutes at a flowrate of 5000 nL/min using 0.1% formic acid. Peptides were separated on a 0.1×250 mm monolithic column (Dionex PepSwift) at 60° C. using a linear gradient of 5 to 25% acetonitrile and 0.1% formic acid at a flowrate of 800 nL/min. Desolvation and ionization of peptides eluting from the column was performed using 3 L/min nitrogen gas at 150° C. and 1300V capillary voltage. The mass spectrometer was programmed to acquire a single survey spectrum (MS) with subsequent data dependent fragmentation analysis (MS/MS) of the top 6 most abundant ions. Survey spectra were acquired at enhanced resolution mode and used the following instrument settings: 50 ms maximum accumulation time, 500.000 ICC target, tune at 1000 m/z, 5 spectra averages. Fragmentation spectra were acquired in extreme scan mode with autoselect fragmentation mode enabled which switches between collision induced dissociation (CID) and electron transfer dissociation (ETD) fragmentation methods based on the mass-to-charge ratio and chargestate of the precursor ion. The following instrument settings were used for fragmentation scans: 500.000 ICC target, 200 ms maximum accumulation time, SPS enabled, 70% CID energy and 0.2 min dynamic exclusion.

Database Searches

Acquired raw mass spectrometry data were processed by Data Analysis software (Bruker Daltonics, v4.1) to generate Mascot compatible input files (GMF format). GMF files were loaded into ProteinScape software (Bruker Daltonics, V3.1) and searched against a sequence database using the Mascot database search software. The fasta sequence database contained the trastuzumab light- and heavy-chain protein sequences with added contaminant protein sequences (e.g. LysC, Trypsin and keratins). Searches were performed using the following settings: 0.35 Da precursor mass tolerance, 0.35 Da fragment ion mass tolerance, tryptic specificity with a maximum of 2 missed cleavages, carbamidomethylation (C) as fixed modification. The following variable modifications were specified: oxidation (MHW), deamidation (NQ), carbamylation (K+N-terminus) and acetylation (protein N-terminus). Peptides with Mascot ion scores above identity score threshold were accepted as valid identifications (peptide false discovery rate<1%).

Relative Quantitation

For the trastuzumab heavy chain protein, a single peptide with histidine oxidation (sequence K.FNWYVDGVEVH*NAK.T, with oxidized H11) was exclusively identified in trastuzumab-conjugate obtained by copper-catalyzed conjugation of 46, but none was detected in the other samples. Extracted ion current (EIC) chromatograms for the peptide with and without oxidized histidine (EIC: 847.46±0.5 m/z and EIC: 839.97±0.5 m/z, respectively) were generated in DataAnalysis software. In addition, EIC chromatograms for the following two peptides were used for normalization purposes: -.EVQLVESGGGLVQPGGSLR.L (EIC: 941.6±0.5 m/z) and K.GPSVFPLAPSSK.S (EIC: 593.95±0.5 m/z). Integrated peak areas from three replicate measurements were averaged and expressed relative to native trastuzumab, indicating that the above fragment with oxidized histidine amounts to 69% of total of that particular fragment (31% unmodified fragment).

For the trastuzumab light chain protein, a single peptide with methionine oxidation (sequence -.DIQM*TQSPSSLSASVGDR.V, with oxidized M4) was exclusively identified in trastuzumab-conjugate obtained by copper-catalyzed conjugation of 46, but none was detected in the other samples.

Example 40. Cloning and Expression of GalT Mutants Y289N, Y289F, Y289M, Y289V, Y289A and Y289G and Y289I The GalT mutant genes were amplified from a construct containing the sequence encoding the catalytic domain of GalT consisting of 130-402 aa residues, by the overlap extension PCR method. The wild type enzyme is represented by SEQ ID NO: 17. For Y289N mutant (represented by SEQ ID NO: 18), the first DNA fragment was amplified with a pair of primers: Oligo38_GalT_External_Fw (CAG CGA CATATG TCG CTG ACC GCA TGC CCT GAG GAG TCC represented by SEQ ID NO: 1) and Oligo19_GalT_Y289N_Rw (GAC ACC TCC AAA GTT CTG CAC GTA AGG TAG GCT AAA represented by SEQ ID NO: 2). The NdeI restriction site is underlined, while the mutation site is highlighted in bold. The second fragment was amplified with a pair of primers: Oligo29_GalT_External_Rw (CTG ATG GAT GGATCC CTA GCT CGG CGT CCC GAT GTC CAC represented by SEQ ID NO: 3) and Oligo18_GalT_Y289N_Fw (CCT TAC GTG CAG AAC TTT GGA GGT GTC TCT GCT CTA represented by SEQ ID NO: 4). The BamHI restriction site is underlined, while the mutation site is highlighted in bold. The two fragments generated in the first round of PCR were fused in the second round using Oligo38_GalT_External_Fw and Oligo29_GalT_External_Rw primers. After digestion with NdeI and BamHI. This fragment was ligated into the pET16b vector cleaved with the same restriction enzymes. The newly constructed expression vector contained the gene encoding Y289N mutant and the sequence encoding for the His-tag from pET16b vector, which was confirmed by DNA sequencing results. For the construction of Y289F (represented by SEQ ID NO: 19), Y289M (represented by SEQ ID NO: 20), Y289I (represented by SEQ ID NO: 21), Y289V (represented by SEQ ID NO: 22), Y289A (represented by SEQ ID NO: 23) and Y289G (represented by SEQ ID NO: 24) mutants the same procedure was used, with the mutation sites changed to TTT, ATG, ATT, GTG, GCG or GGC triplets encoding for phenylalanine, methionine, isoleucine, valine, alanine or glycine, respectively. More specifically, for the construction of Y289F the first DNA fragment was amplified with a pair of primers defined herein as SEQ ID NO: 1 and SEQ ID NO: 5 and the second fragment was amplified with a pair of primers defined herein as SEQ ID NO: 3 and SEQ ID NO: 6 (be referred to Table 1 for the related sequences). Furthermore, for the construction of Y289M the first DNA fragment was amplified with a pair of primers defined herein as SEQ ID NO: 1 and SEQ ID NO: 7 and the second fragment was amplified with a pair of primers defined herein as SEQ ID NO: 3 and SEQ ID NO: 8 (be referred to Table 1 for the related sequences). GalT mutants were expressed, isolated and refolded from inclusion bodies according to the reported procedure by Qasba et al. (*Prot. Expr. Pur.* 2003, 30, 219-229). After refolding, the precipitate was removed and the soluble and folded protein was isolated using a Ni-NTA column (HisTrap excel 1 mL column, GE Healthcare). After elution with 25 mM Tris-HCl pH 8.0, 300 mM NaCl and 200 mM imidazole, the protein was dialyzed against 25 mM Tris-HCl pH 8.0 and concentrated to 2 mg/mL using a spinfilter (Amicon Ultra-15 Centrifugal Filter Unit with Ultracel-10 membrane, Merck Millipore).

TABLE 1

Sequence identification of the primers used

| SEQ ID NO | Nucleotide sequence |
| --- | --- |
| SEQ ID NO: 1 | CAG CGA <u>CAT ATG</u> TCG CTG ACC GCA TG CCT GAG GAG TCC |
| SEQ ID NO: 2 | GAC ACC TCC AAA GTT CTG CAC GTA AGG TAG GCT AAA |
| SEQ ID NO: 3 | CTG ATG GAT <u>GGA TCC</u> CTA GCT CGG CGT CCC GAT GTC CAC |
| SEQ ID NO: 4 | CCT TAC GTG CAG AAC TTT GGA GGT GTC TCT GCT CTA |
| SEQ ID NO: 5 | GAC ACC TCC AAA AAA CTG CAC GTA AGG TAG GCT AAA |
| SEQ ID NO: 6 | CCT TAC GTG CAG TTT TTT GGA GGT GTC TCT GCT CTA |
| SEQ ID NO: 7 | GAC ACC TCC AAA CAT CTG CAC GTA AGG TAG GCT AAA |
| SEQ ID NO: 8 | CCT TAC GTG CAG ATG TTT GGA GGT GTC TCT GCT CTA |

TABLE 1 -continued

Sequence identification of the primers used

| SEQ ID NO | Nucleotide sequence |
|---|---|
| SEQ ID NO: 9 | GAC ACC TCC AAA AAT CTG CAC GTA AGG TAG GCT AAA |
| SEQ ID NO: 10 | CCT TAC GTG CAG ATT TTT GGA GGT GTC TCT GCT CTA |
| SEQ ID NO: 11 | GAC ACC TCC AAA CAC CTG CAC GTA AGG TAG GCT AAA |
| SEQ ID NO: 12 | CCT TAC GTG CAG GTG TTT GGA GGT GTC TCT GCT CTA |
| SEQ ID NO: 13 | GAC ACC TCC AAA CGC CTG CAC GTA AGG TAG GCT AAA |
| SEQ ID NO: 14 | CCT TAC GTG CAG GCG TTT GGA GGT GTC TCT GCT CTA |
| SEQ ID NO: 15 | GAC ACC TCC AAA GCC CTG CAC GTA AGG TAG GCT AAA |

TABLE 1 -continued

Sequence identification of the primers used

| SEQ ID NO | Nucleotide sequence |
|---|---|
| SEQ ID NO: 16 | CCT TAC GTG CAG GGC TTT GGA GGT GTC TCT GCT CTA |

Example 41. Transfer of UDP-GalNAz with GalT Mutants Y289N, Y289F and Y289M

Enzymatic introduction of galactose derivative onto trastuzumab was effected with one of the β(1,4)-Gal-T1 mutants Y289N, Y289F or Y289M. Thus, the deglycosylated trastuzumab (prepared as described above, 10 mg/mL) was incubated with UDP-N-azidoacetylgalactosamine 52 (UDP-GalNAz) (1 mM) and the respective β(1,4)-Gal-T1 mutant (0.1 mg/mL) in 10 mM $MnCl_2$ and 25 mM Tris-HCl pH 8.0 for 16 hours at 30° C.

For all three mutants Y289N, Y289F or Y289M, mass spectral analysis of the crude mixture indicated the clean conversion of core GlcNAc(Fuc)-substituted trastuzumab into trastuzumab(GalNAz)$_2$ (49713 Da, 90% of total heavy chain).

The invention claimed is:

1. An antibody-conjugate, obtainable by a process comprising the steps of:
   (i) reacting an antibody comprising a core N-acetylglucosamine (GlcNAc) substituent with a compound of the formula $S(A)_x$-P in the presence of a suitable catalyst, wherein:
      the core N-acetylglucosamine substituent is present at an N-glycosylation site of the antibody and is optionally fucosylated,
      $S(A)_x$-P is a substrate for the catalyst,
         wherein:
         S is selected from the group consisting of galactose, mannose, N-acetylglucosamine, glucose, N-acetylgalactosamine, glucuronic acid, fucose, and N-acetylneuraminic acid, comprising x functional groups A,
         A is an azido group,
         x is 1 or 2, and
         P is selected from the group consisting of uridine diphosphate (UDP), guanosine diphosphate (GDP), and cytidine diphosphate (CDP),
   to obtain a modified antibody, defined as an antibody comprising a GlcNAc-$S(A)_x$ substituent bonded to the antibody via C1 of the N-acetylglucosamine of the GlcNAc-$S(A)_x$ substituent, according to Formula (4):

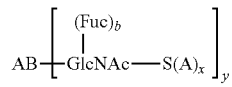

(4)

wherein:
      AB represents an antibody;
      GlcNAc is N-acetylglucosamine;
      Fuc is fucose;
      b is 0 or 1; and
      y is 1 to 4; and
   (ii) reacting the modified antibody with a modified active substance, wherein the modified active substance has the Formula (15), (16), (17), or (19):

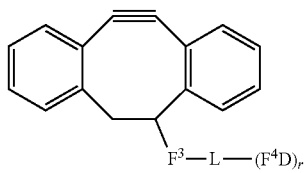

15

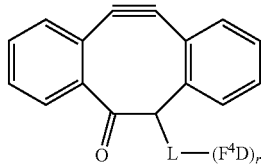

16

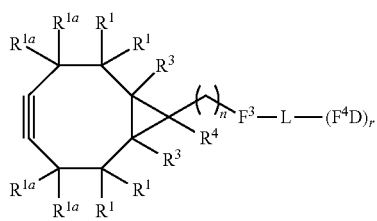

17

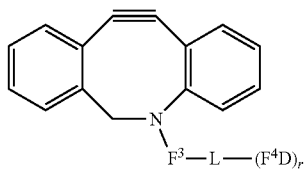

19 wherein:
F³ is selected from the group consisting of —[C(R⁵)₂C(R⁵)₂O]_q—, —X—, —NR⁵—, —C(X)NR⁵—, —C(R⁵)₂X—, —C(X)—, —C(X)X—, —S(O)—, —S(O)₂—, —S(O)₂O—, —S(O)NR⁵—, —S(O)₂NR⁵—, —OS(O)—, —OS(O)₂—, —OS(O)O—, —OS(O)₂O—, —P(O)(R⁵)(O)—, —P(O)(OR⁵)—, —OP(O)(OR⁵)—, —Si(R⁵)₂—, —XC(X)—, —XC(X)X—, —XC(X)N(R⁵)—, —N(R⁵)C(X)—, —N(R⁵)C(X)X—, —N(R⁵)C(X)N(R⁵)—, and combinations of two or more thereof;

L is selected from the group consisting of selected from the group consisting of linear or branched C₁-C₂₀₀ alkylene groups, C₂-C₂₀₀ alkenylene groups, C₂-C₂₀₀ alkynylene groups, C₃-C₂₀₀ cycloalkylene groups, C₅-C₂₀₀ cycloalkenylene groups, C₈-C₂₀₀ cycloalkynylene groups, C₇-C₂₀₀ alkylarylene groups, C₇-C₂₀₀ arylalkylene groups, C₈-C₂₀₀ arylalkenylene groups, and C₉-C₂₀₀ arylalkynylene groups, wherein the groups are optionally substituted with an oxo group and/or interrupted by one or more heteroatoms selected from N and O:

F⁴ is selected from the group consisting of —[C(R⁵)₂C(R⁵)₂O]_q—, —X—, —NR⁵—, —C(X)NR⁵—, —C(R⁵)₂X—, —C(X)—, —C(X)X—, —S(O)—, —S(O)₂—, —S(O)₂O—, —S(O)NR⁵—, —S(O)₂NR⁵—, —OS(O)—, —OS(O)₂—, —OS(O)O—, —OS(O)₂O—, —P(O)(R)(O)—, —P(O)(OR⁵)—, —OP(O)(OR⁵)—, —Si(R⁵)₂—, —XC(X)—, —XC(X)X—, —XC(X)N(R⁵)—, —N(R⁵)C(X)—, —N(R)C(X)X—, —N(R⁵)C(X)N(R⁵)—, cleavable linker, and combinations of two or more thereof;

wherein:
g is in the range of 1 to 200;
X is independently oxygen or sulphur; and
R⁵ is independently selected from the group consisting of hydrogen, C₁-C₂₄ alkyl groups, C₆-C₂₄ (hetero)aryl groups, C₇-C₂₄ alkyl(hetero)aryl groups and C₇-C₂₄ (hetero)arylalkyl groups;
provided that together F³-L-F⁴ comprise at least one —[C(R⁵)₂C(R⁵)₂O]_q— group;
R¹ᵃ, R¹, and R³ are each hydrogen;
R⁴ is selected from the group consisting of hydrogen, —F³-L-(F⁴-D)_r, —(CH₂)_n—F³-L-(F⁴-D)_r, and halogen;
D is an active substance, wherein an active substance is a substance that is biologically and/or pharmaceutically active;
a is 0, 1, or 2;
a' is 0, 1, or 2;
r is an integer from 1 to 8; and
n is 1, 2, 3, 4, 5, 6, 7, 8, 9 or 10.

2. The antibody-conjugate according to claim 1, wherein the antibody is a whole antibody, and wherein x is 1 and y is 2.

3. The antibody-conjugate according to claim 1, wherein the modified active substance has the Formula (17):

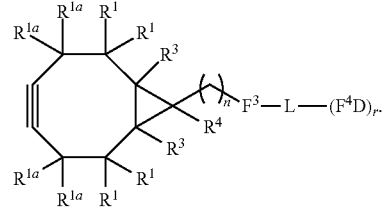

17

4. The antibody-conjugate according to claim 1, wherein the modified active substance has the Formula (19):

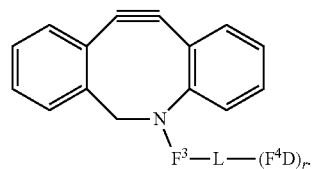

19

5. The antibody-conjugate according to claim 1, wherein the modified active substance has the Formula (15):

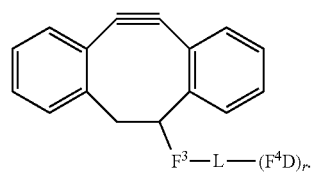

15 wherein: r is an integer from 1 to 4.

6. The antibody-conjugate according to claim 1, wherein the modified active substance has the Formula (16):

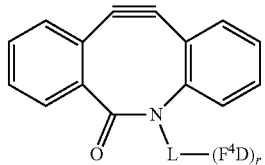

16 wherein: r is an integer from 1 to 4.

7. The antibody-conjugate according to claim 1, wherein $F^4$ comprise at least one vc-PABC group.

8. The antibody-conjugate according to claim 1, wherein n is 1, 2, 3, 4, or 5.

9. The antibody-conjugate according to claim 3, wherein r is an integer from 1 to 4.

10. The antibody-conjugate according to claim 4, wherein r is an integer from 1 to 4.

11. The antibody-conjugate according to claim 5, wherein r is an integer from 1 to 4.

12. The antibody-conjugate according to claim 6, wherein r is an integer from 1 to 4.

13. An antibody-conjugate according to the Formula (15b), (15c), (16b), (16c), (21), (22), or (22b):

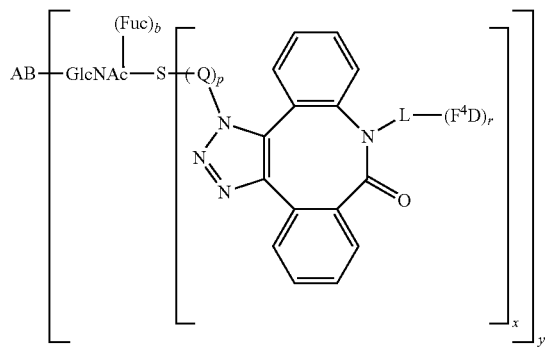

16b

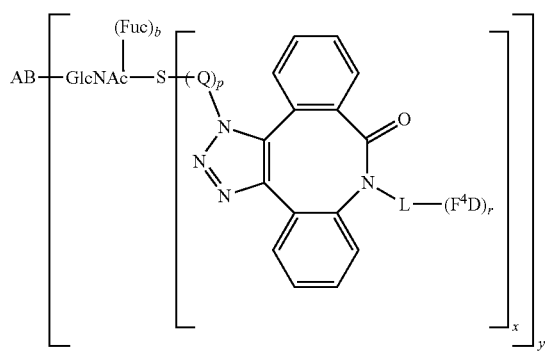

16c

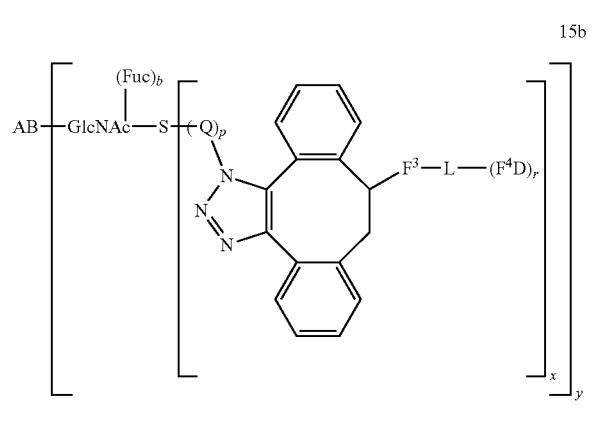

15b

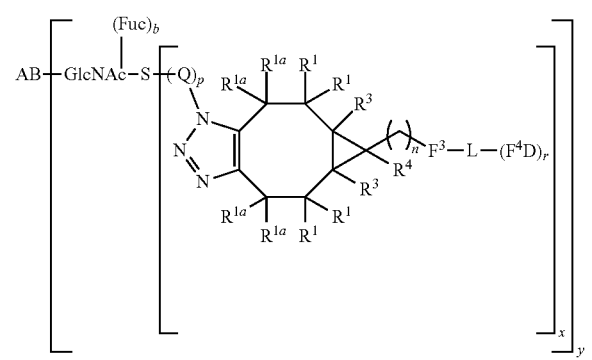

21

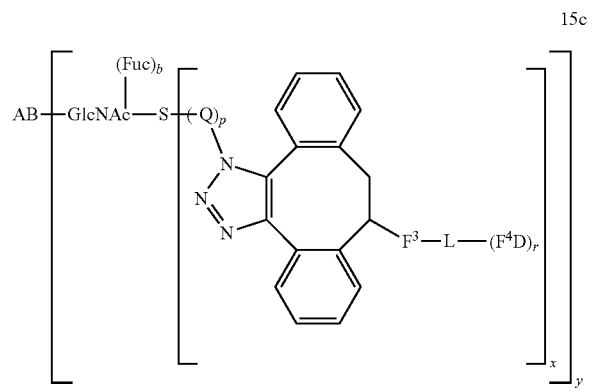

15c

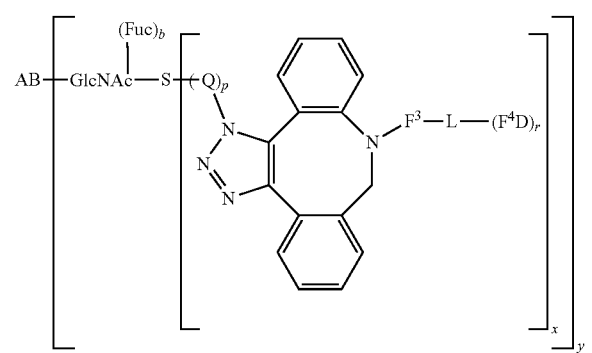

22

-continued

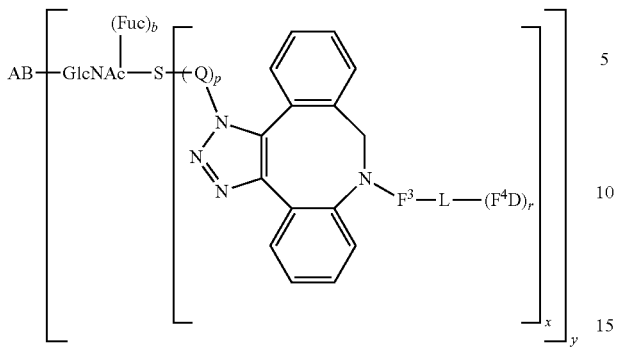

wherein:
b is 0 or 1;
p is 0 or 1;
Q is —N(H)C(O)CH$_2$— or —CH$_2$—;
x is 1 or 2;
y is 1-4;
AB is an antibody;
S is selected from the group consisting of galactose, mannose, N-acetylglucosamine, glucose, N-acetylgalactosamine, glucuronic acid, fucose, and N-acetylneuraminic acid;
GlcNAc is N-acetylglucosamine and is present at an N-glycosylation site of the antibody;
Fuc is fucose;
F$^3$ is selected from the group consisting of —[C(R$^5$)$_2$C(R$^5$)$_2$O]$_q$—, —X—, —NR$^5$—, —C(X)NR$^5$—, —C(R$^5$)$_2$X—, —C(X)—, —C(X)X—, —S(O)—, —S(O)$_2$—, —S(O)$_2$O—, —S(O)NR$^5$—, —S(O)$_2$NR$^5$—, —OS(O)—, —OS(O)$_2$—, —OS(O)O—, —OS(O)$_2$O—, —P(O)(R$^5$)(O)—, —P(O)(OR$^5$)—, —OP(O)(OR$^5$)—, —Si(R$^5$)$_2$—, —XC(X)—, —XC(X)X—, —XC(X)N(R$^5$)—, —N(R$^5$)C(X)—, —N(R$^5$)C(X)X—, —N(R$^5$)C(X)N(R$^5$)—, and combinations of two or more thereof;
L is selected from the group consisting of selected from the group consisting of linear or branched C$_1$-C$_{200}$ alkylene groups, C$_2$-C$_{200}$ alkenylene groups, C$_2$-C$_{200}$ alkynylene groups, C$_3$-C$_{200}$ cycloalkylene groups, C$_5$-C$_{200}$ cycloalkenylene groups, C$_8$-C$_{200}$ cycloalkynylene groups, C$_7$-C$_{200}$ alkylarylene groups, C$_7$-C$_{200}$ arylalkylene groups, C$_8$-C$_{200}$ arylalkenylene groups, and C$_9$-C$_{200}$ arylalkynylene groups, wherein the groups are optionally substituted with an oxo group and/or interrupted by one or more heteroatoms selected from N and O;
F$^4$ is selected from the group consisting of —[C(R$^5$)$_2$C(R$^5$)$_2$O]$_q$—, —X—, —NR$^5$—, —C(X)NR$^5$—, —C(R$^5$)$_2$X—, —C(X)—, —C(X)X—, —S(O)—, —S(O)$_2$—, —S(O)$_2$O—, —S(O)NR$^5$—, —S(O)$_2$NR$^5$—, —OS(O)—, —OS(O)$_2$—, —OS(O)O—, —OS(O)$_2$O—, —P(O)(R$^5$)(O)—, —P(O)(OR$^5$)—, —OP(O)(OR$^5$)—, —Si(R$^5$)$_2$—, —XC(X)—, —XC(X)X—, —XC(X)N(R$^5$)—, —N(R$^5$)C(X)—, —N(R$^5$)C(X)X—, —N(R$^5$)C(X)N(R$^5$)—, cleavable linker, and combinations of two or more thereof;
wherein:
q is in the range of 1 to 200;
X is independently oxygen or sulphur; and
R$^5$ is independently selected from the group consisting of hydrogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups;
provided that together F$^3$-L-F$^4$ comprise at least one —[C(R$^5$)$_2$C(R$^5$)$_2$O]$_q$— group;
R$^{1a}$, R$^1$, and R$^3$ are each hydrogen;
R$^4$ is selected from the group consisting of hydrogen, —F$^3$-L-(F$^4$-D)$_r$, —(CH$_2$)$_n$—F$^3$-L-(F$^4$-D)$_r$, and halogen;
D is an active substance, wherein an active substance is a substance that is biologically and/or pharmaceutically active;
a is 0, 1, or 2;
a' is 0, 1, or 2
r is an integer from 1 to 8; and
n is 1, 2, 3, 4, 5, 6, 7, 8, 9 or 10.

14. The antibody-conjugate according to claim 13, wherein the antibody-conjugate has the Formula (21):

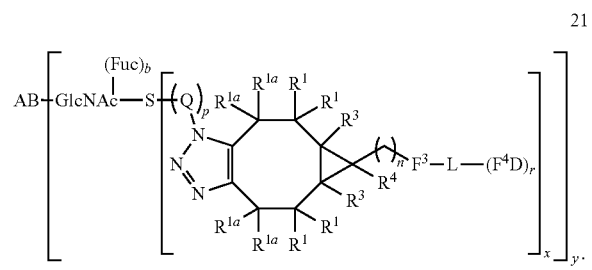

15. The antibody-conjugate according to claim 14, wherein n is 1, 2, 3, 4, or 5.

16. The antibody-conjugate according to claim 13, wherein the antibody-conjugate is of the Formula (15b), (15c), (22), or (22b):

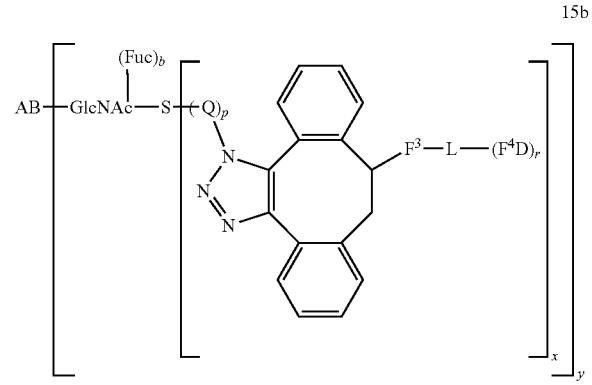

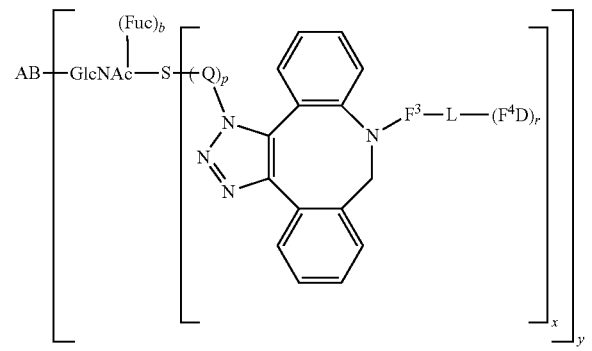

15c

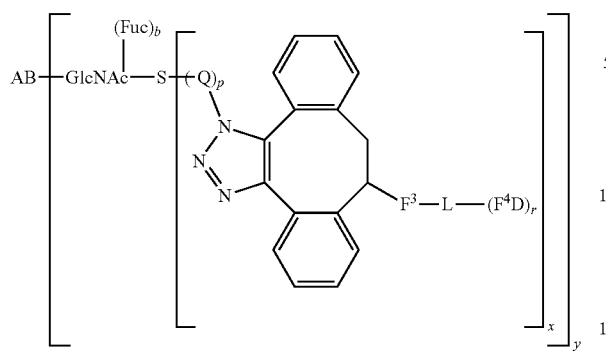

22b

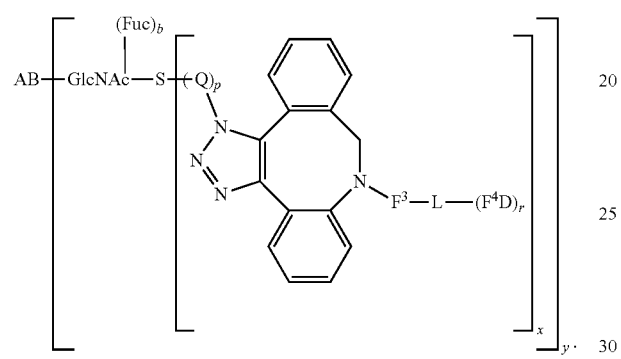

17. The antibody-conjugate according to claim 13, wherein the antibody-conjugate is of the Formula (16b) or (16c):

16b

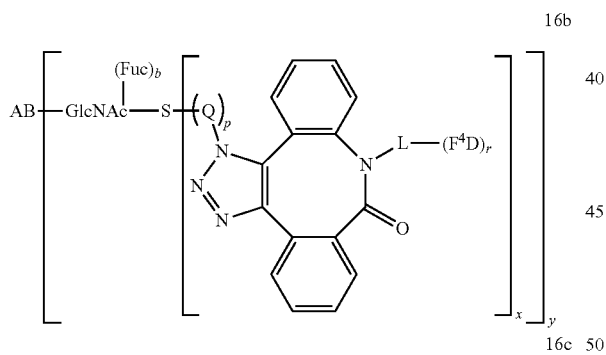

16c

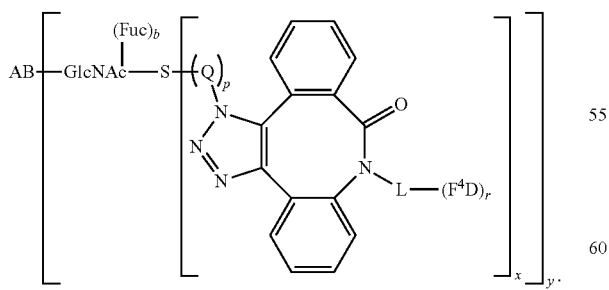

18. The antibody-conjugate according to claim 13, wherein the molecule of interest (D) is selected from the group consisting of an active substance and a reporter molecule.

19. The antibody-conjugate according to claim 13, wherein GlcNAc is present at a N297 N-glycosylation site of the antibody.

20. The antibody-conjugate according to claim 13, wherein $F^4$ comprise at least one vc-PABC group.

21. The antibody-conjugate according to claim 13, wherein n is 1, 2, 3, 4, or 5.

22. The antibody-conjugate according to claim 14, wherein r is an integer from 1 to 4.

23. The antibody-conjugate according to claim 15, wherein r is an integer from 1 to 4.

24. The antibody-conjugate according to claim 16, wherein r is an integer from 1 to 4.

25. The antibody-conjugate according to claim 17, wherein r is an integer from 1 to 4.

26. A process for the preparation of an antibody-conjugate comprising reacting a modified antibody with a modified active substance, wherein:

the modified antibody has the Formula (4):

4

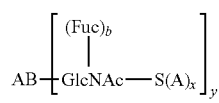

wherein:
the GlcNAc-S(A)$_x$ substituent is bonded to the antibody via C1 of the N-acetylglucosamine of the GlcNAc-S(A)x substituent;
S is selected from the group consisting of galactose, mannose, N-acetylglucosamine, glucose, N-acetylgalactosamine, glucuronic acid, fucose, and N-acetylneuraminic acid, comprising x functional groups A,
A is an azido group,
x is 1 or 2,
AB represents an antibody;
GlcNAc is N-acetylglucosamine and is present at an N-glycosylation site of the antibody;
Fuc is fucose;
b is 0 or 1; and
y is 1 to 4;

the modified active substance has the Formula (15), (16), (17), or (19):

15

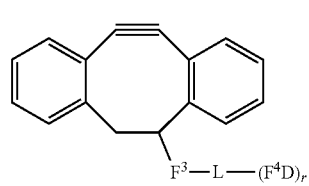

16

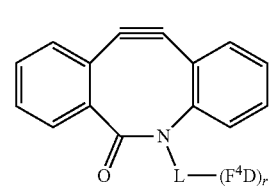

-continued

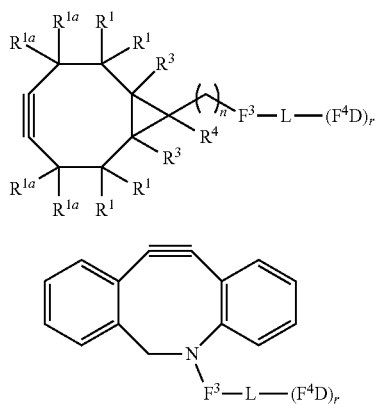

wherein:

F³ is selected from the group consisting of —[C(R⁵)₂C(R⁵)₂O]_q—, —X—, —NR⁵—, —C(X)NR⁵—, —C(R⁵)₂X—, —C(X)—, —C(X)X—, —S(O)—, —S(O)₂—, —S(O)₂O—, —S(O)NR⁵—, —S(O)₂NR⁵—, —OS(O)—, —OS(O)₂—, —OS(O)O—, —OS(O)₂O—, —P(O)(R⁵)(O)—, —P(O)(OR⁵)—, —OP(O)(OR⁵)—, —Si(R⁵)₂—, —XC(X)—, —XC(X)X—, —XC(X)N(R⁵)—, —N(R⁵)C(X)—, —N(R⁵)C(X)X—, —N(R⁵)C(X)N(R⁵)—, and combinations of two or more thereof;

L is selected from the group consisting of selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, and $C_9$-$C_{200}$ arylalkynylene groups, wherein the groups are optionally substituted with an oxo group and/or interrupted by one or more heteroatoms selected from N and O;

F⁴ is selected from the group consisting of —[C(R⁵)₂C(R⁵)₂O]_q—, —X—, —NR⁵—, —C(X)NR⁵—, —C(R⁵)₂X—, —C(X)—, —C(X)X—, —S(O)—, —S(O)₂—, —S(O)₂O—, —S(O)NR⁵—, —S(O)₂NR⁵—, —OS(O)—, —OS(O)₂—, —OS(O)O—, —OS(O)₂O—, —P(O)(R⁵)(O)—, —P(O)(OR⁵)—, —OP(O)(OR⁵)—, —Si(R⁵)₂—, —XC(X)—, —XC(X)X—, —XC(X)N(R⁵)—, —N(R⁵)C(X)—, —N(R⁵)C(X)X—, —N(R⁵)C(X)N(R⁵)—, cleavable linker, and combinations of two or more thereof;

wherein:

q is in the range of 1 to 200;

X is independently oxygen or sulphur; and

R⁵ is independently selected from the group consisting of hydrogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;

provided that together F³-L-F⁴ comprise at least one —[C(R⁵)₂C(R⁵)₂O]_q— group;

R¹ᵃ, R¹, and R³ are each hydrogen;

R⁴ is selected from the group consisting of hydrogen, —F³-L-(F⁴-D)_r, —(CH₂)_n—F³-L-(F⁴-D)_r, and halogen;

D is an active substance, wherein an active substance is a substance that is biologically and/or pharmaceutically active;

a is 0, 1, or 2;

a' is 0, 1, or 2;

r is an integer from 1 to 8; and n is 1, 2, 3, 4, 5, 6, 7, 8, 9 or 10; and the antibody-conjugate has the Formula (15b), (15c), (16b), (16c), (21), (22), or (22b):

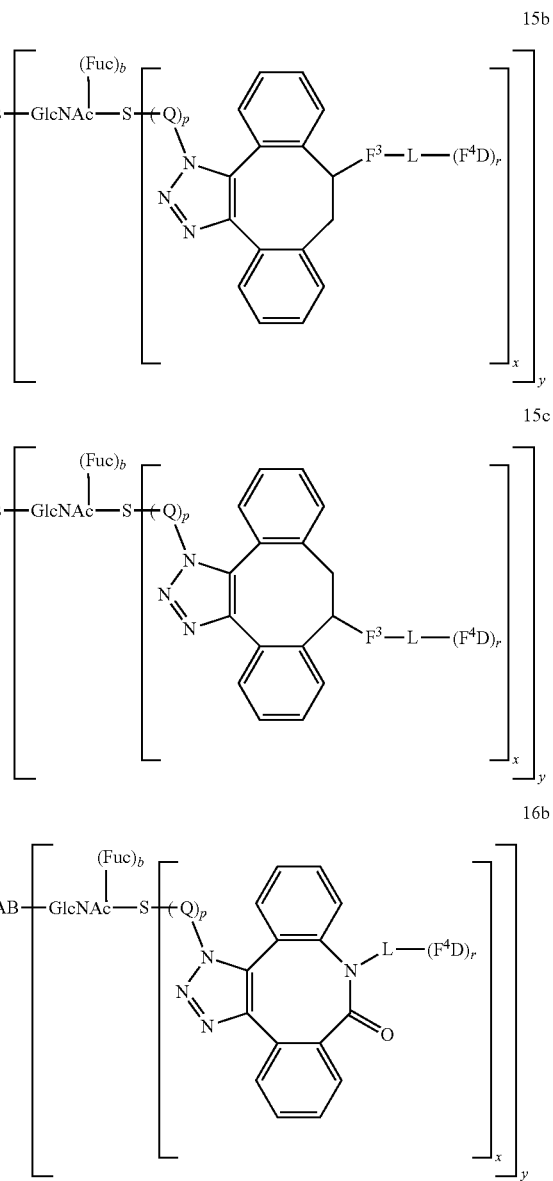

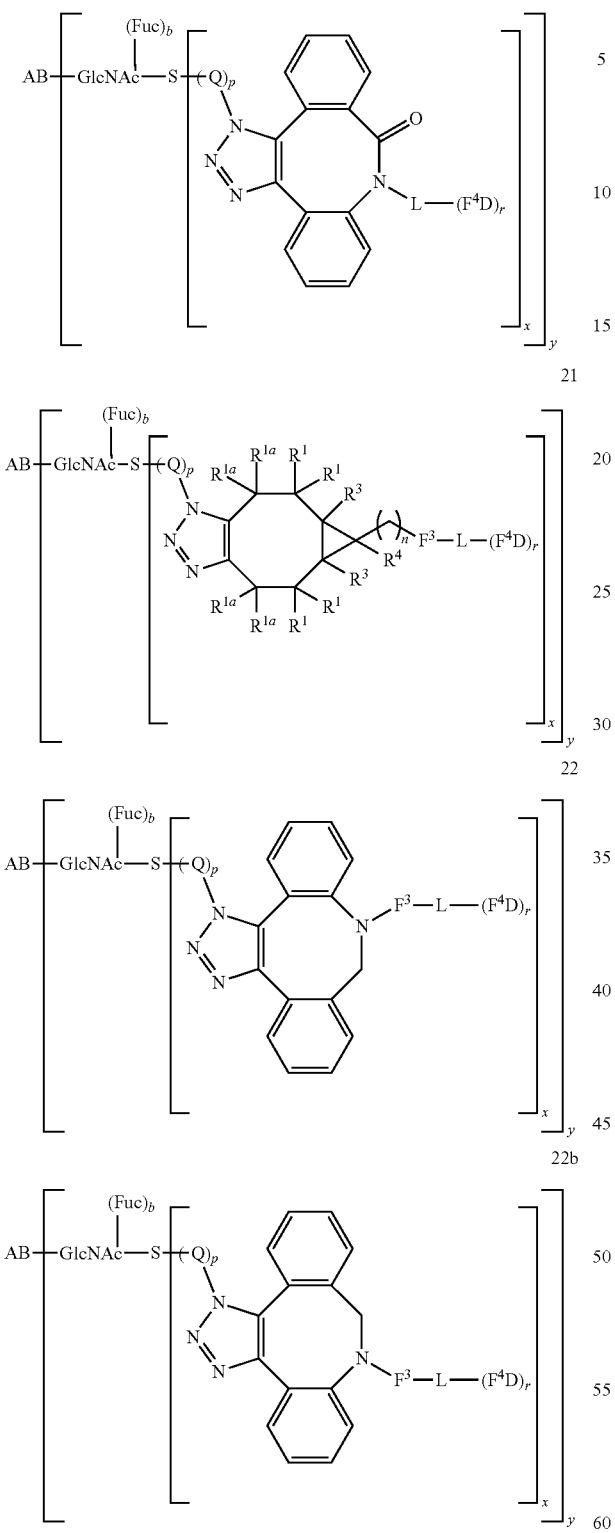

wherein:

p is 0 or 1; and

Q is —N(H)C(O)CH$_2$— or —CH$_2$—.

27. The process according to claim 26 further comprising:
reacting an antibody comprising a core N-acetylglucosamine (GlcNAc) substituent with a compound of the formula S(A)$_x$-P in the presence of a catalyst,
wherein:
the core N-acetylglucosamine substituent is present at an N-glycosylation site of the antibody and is optionally fucosylated,
S(A)$_x$-P is a substrate for the catalyst,
wherein P is selected from the group consisting of uridine diphosphate (UDP), guanosine diphosphate (GDP), and cytidine diphosphate (CDP); and
the catalyst is selected from the group consisting of GalT Y289L, GalT Y289N, GalT Y289I, GalT Y289F, GalT Y289M, GalT Y289V, GalT Y289G, GalT Y289I, and GalT Y289A;
to obtain the modified antibody.

28. The process according to claim 26, wherein the modified active substance has the Formula (17):

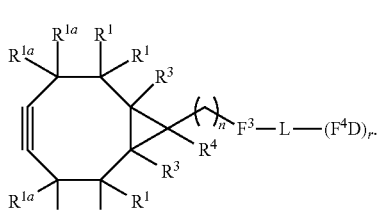

29. The process according to claim 26, wherein the modified active substance has the Formula (15) or (19):

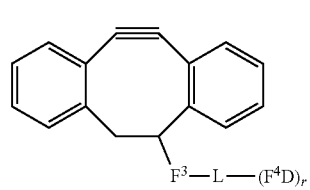

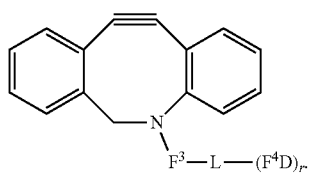

30. The process according to claim 9, wherein the modified active substance has the Formula (16)

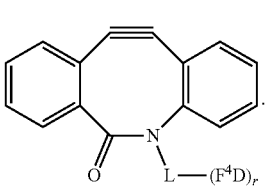

31. The antibody-conjugate according to claim 26, wherein F$^4$ comprise at least one vc-PABC group.

32. The antibody-conjugate according to claim 26, wherein n is 1, 2, 3, 4, or 5.

33. The antibody-conjugate according to claim 28, wherein r is an integer from 1 to 4.

34. The antibody-conjugate according to claim 29, wherein r is an integer from 1 to 4.

35. The antibody-conjugate according to claim 30, wherein r is an integer from 1 to 4.

* * * * *

SEQUENCE LISTING

```
<160> NUMBER OF SEQ ID NOS: 24

<210> SEQ ID NO 1
<211> LENGTH: 39
<212> TYPE: DNA
<213> ORGANISM: artificial
<220> FEATURE:
<223> OTHER INFORMATION: primer sequence

<400> SEQUENCE: 1
cagcgacata tgtcgctgac cgcatgccct gaggagtcc                      39

<210> SEQ ID NO 2
<211> LENGTH: 36
<212> TYPE: DNA
<213> ORGANISM: artificial
<220> FEATURE:
<223> OTHER INFORMATION: primer sequence

<400> SEQUENCE: 2
gacacctcca aagttctgca cgtaaggtag gctaaa                         36

<210> SEQ ID NO 3
<211> LENGTH: 39
<212> TYPE: DNA
<213> ORGANISM: artificial
<220> FEATURE:
<223> OTHER INFORMATION: primer sequence

<400> SEQUENCE: 3
ctgatggatg gatccctagc tcggcgtccc gatgtccac                      39

<210> SEQ ID NO 4
<211> LENGTH: 36
<212> TYPE: DNA
<213> ORGANISM: artificial
<220> FEATURE:
<223> OTHER INFORMATION: primer sequence

<400> SEQUENCE: 4
```
ccttacgtgc agaactttgg aggtgtctct gctcta                                    36

<210> SEQ ID NO 5
<211> LENGTH: 36
<212> TYPE: DNA
<213> ORGANISM: artificial
<220> FEATURE:
<223> OTHER INFORMATION: primer sequence

<400> SEQUENCE: 5
gacacctcca aaaaactgca cgtaaggtag gctaaa                                    36

<210> SEQ ID NO 6
<211> LENGTH: 36
<212> TYPE: DNA
<213> ORGANISM: artificial
<220> FEATURE:
<223> OTHER INFORMATION: primer sequence

<400> SEQUENCE: 6
ccttacgtgc agttttttgg aggtgtctct gctcta                                    36

<210> SEQ ID NO 7
<211> LENGTH: 36
<212> TYPE: DNA
<213> ORGANISM: artificial
<220> FEATURE:
<223> OTHER INFORMATION: primer sequence

<400> SEQUENCE: 7
gacacctcca aacatctgca cgtaaggtag gctaaa                                    36

<210> SEQ ID NO 8
<211> LENGTH: 36
<212> TYPE: DNA
<213> ORGANISM: artificial
<220> FEATURE:
<223> OTHER INFORMATION: primer sequence

<400> SEQUENCE: 8
ccttacgtgc agatgtttgg aggtgtctct gctcta                                    36

<210> SEQ ID NO 9
<211> LENGTH: 36
<212> TYPE: DNA
<213> ORGANISM: artificial
<220> FEATURE:
<223> OTHER INFORMATION: primer sequence

<400> SEQUENCE: 9
gacacctcca aaaatctgca cgtaaggtag gctaaa                                    36

<210> SEQ ID NO 10
<211> LENGTH: 36
<212> TYPE: DNA
<213> ORGANISM: artificial
<220> FEATURE:
<223> OTHER INFORMATION: primer sequence

<400> SEQUENCE: 10
ccttacgtgc agattttgg aggtgtctct gctcta                                     36

<210> SEQ ID NO 11
<211> LENGTH: 36
<212> TYPE: DNA
<213> ORGANISM: artificial

```
<220> FEATURE:
<223> OTHER INFORMATION: primer sequence

<400> SEQUENCE: 11
gacacctcca aacacctgca cgtaaggtag gctaaa                              36

<210> SEQ ID NO 12
<211> LENGTH: 36
<212> TYPE: DNA
<213> ORGANISM: artificial
<220> FEATURE:
<223> OTHER INFORMATION: primer sequence

<400> SEQUENCE: 12
ccttacgtgc aggtgtttgg aggtgtctct gctcta                              36

<210> SEQ ID NO 13
<211> LENGTH: 36
<212> TYPE: DNA
<213> ORGANISM: artificial
<220> FEATURE:
<223> OTHER INFORMATION: primer sequence

<400> SEQUENCE: 13
gacacctcca aacgcctgca cgtaaggtag gctaaa                              36

<210> SEQ ID NO 14
<211> LENGTH: 36
<212> TYPE: DNA
<213> ORGANISM: artificial
<220> FEATURE:
<223> OTHER INFORMATION: primer sequence

<400> SEQUENCE: 14
ccttacgtgc aggcgtttgg aggtgtctct gctcta                              36

<210> SEQ ID NO 15
<211> LENGTH: 36
<212> TYPE: DNA
<213> ORGANISM: artificial
<220> FEATURE:
<223> OTHER INFORMATION: primer sequence

<400> SEQUENCE: 15
gacacctcca aagccctgca cgtaaggtag gctaaa                              36

<210> SEQ ID NO 16
<211> LENGTH: 36
<212> TYPE: DNA
<213> ORGANISM: artificial
<220> FEATURE:
<223> OTHER INFORMATION: primer sequence

<400> SEQUENCE: 16
ccttacgtgc agggctttgg aggtgtctct gctcta                              36

<210> SEQ ID NO 17
<211> LENGTH: 402
<212> TYPE: PRT
<213> ORGANISM: Bos taurus

<400> SEQUENCE: 17

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
```

```
                    20                  25                  30
His Leu Gly Val Thr Leu Val Tyr Tyr Leu Ala Gly Arg Asp Leu Arg
             35                  40                  45
Arg Leu Pro Gln Leu Val Gly Val His Pro Pro Leu Gln Gly Ser Ser
 50                  55                  60
His Gly Ala Ala Ala Ile Gly Gln Pro Ser Gly Glu Leu Arg Leu Arg
 65                  70                  75                  80
Gly Val Ala Pro Pro Pro Leu Gln Asn Ser Ser Lys Pro Arg Ser
                 85                  90                  95
Arg Ala Pro Ser Asn Leu Asp Ala Tyr Ser His Pro Gly Pro Gly Pro
             100                 105                 110
Gly Pro Gly Ser Asn Leu Thr Ser Ala Pro Val Pro Ser Thr Thr Thr
         115                 120                 125
Arg Ser Leu Thr Ala Cys Pro Glu Glu Ser Pro Leu Leu Val Gly Pro
     130                 135                 140
Met Leu Ile Glu Phe Asn Ile Pro Val Asp Leu Lys Leu Ile Glu Gln
145                 150                 155                 160
Gln Asn Pro Lys Val Lys Leu Gly Gly Arg Tyr Thr Pro Met Asp Cys
                 165                 170                 175
Ile Ser Pro His Lys Val Ala Ile Ile Leu Phe Arg Asn Arg Gln
             180                 185                 190
Glu His Leu Lys Tyr Trp Leu Tyr Tyr Leu His Pro Met Val Gln Arg
         195                 200                 205
Gln Gln Leu Asp Tyr Gly Ile Tyr Val Ile Asn Gln Ala Gly Glu Ser
     210                 215                 220
Met Phe Asn Arg Ala Lys Leu Leu Asn Val Gly Phe Lys Glu Ala Leu
225                 230                 235                 240
Lys Asp Tyr Asp Tyr Asn Cys Phe Val Phe Ser Asp Val Asp Leu Ile
                 245                 250                 255
Pro Met Asn Asp His Asn Thr Tyr Arg Cys Phe Ser Gln Pro Arg His
             260                 265                 270
Ile Ser Val Ala Met Asp Lys Phe Gly Phe Ser Leu Pro Tyr Val Gln
         275                 280                 285
Tyr Phe Gly Gly Val Ser Ala Leu Ser Lys Gln Gln Phe Leu Ser Ile
     290                 295                 300
Asn Gly Phe Pro Asn Asn Tyr Trp Gly Trp Gly Gly Glu Asp Asp Asp
305                 310                 315                 320
Ile Tyr Asn Arg Leu Ala Phe Arg Gly Met Ser Val Ser Arg Pro Asn
                 325                 330                 335
Ala Val Ile Gly Lys Cys Arg Met Ile Arg His Ser Arg Asp Lys Lys
             340                 345                 350
Asn Glu Pro Asn Pro Gln Arg Phe Asp Arg Ile Ala His Thr Lys Glu
         355                 360                 365
Thr Met Leu Ser Asp Gly Leu Asn Ser Leu Thr Tyr Met Val Leu Glu
     370                 375                 380
Val Gln Arg Tyr Pro Leu Tyr Thr Lys Ile Thr Val Asp Ile Gly Thr
385                 390                 395                 400

Pro Ser

<210> SEQ ID NO 18
<211> LENGTH: 402
<212> TYPE: PRT
<213> ORGANISM: artificial
<220> FEATURE:
```

<223> OTHER INFORMATION: bos taurus GalT Y289N

<400> SEQUENCE: 18

```
Met Lys Phe Arg Glu Pro Leu Leu Gly Gly Ser Ala Ala Met Pro Gly
 1               5                  10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
            115                 120                 125

Arg Ser Leu Thr Ala Cys Pro Glu Glu Ser Pro Leu Leu Val Gly Pro
130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Asn Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400
```

Pro Ser

<210> SEQ ID NO 19
<211> LENGTH: 402
<212> TYPE: PRT
<213> ORGANISM: artificial
<220> FEATURE:
<223> OTHER INFORMATION: bos taurus GalT Y289F

<400> SEQUENCE: 19

```
Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Phe Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
```

```
                355                 360                 365
Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 20
<211> LENGTH: 402
<212> TYPE: PRT
<213> ORGANISM: artificial
<220> FEATURE:
<223> OTHER INFORMATION: bos taurus GalT Y289M

<400> SEQUENCE: 20

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Met Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320
```

```
Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser
```

<210> SEQ ID NO 21
<211> LENGTH: 402
<212> TYPE: PRT
<213> ORGANISM: artificial
<220> FEATURE:
<223> OTHER INFORMATION: bos taurus GalT Y289I

<400> SEQUENCE: 21

```
Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
            115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
                180                 185                 190

Glu His Leu Lys Tyr Trp Leu Tyr Tyr Leu His Pro Met Val Gln Arg
            195                 200                 205

Gln Gln Leu Asp Tyr Gly Ile Tyr Val Ile Asn Gln Ala Gly Glu Ser
        210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
                260                 265                 270
```

```
Ile Ser Val Ala Met Asp Lys Phe Gly Phe Ser Leu Pro Tyr Val Gln
            275                 280                 285

Ile Phe Gly Gly Val Ser Ala Leu Ser Lys Gln Gln Phe Leu Ser Ile
        290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Tyr Met Val Leu Glu
370                 375                 380

Val Gln Arg Tyr Pro Leu Tyr Thr Lys Ile Thr Val Asp Ile Gly Thr
385                 390                 395                 400

Pro Ser

<210> SEQ ID NO 22
<211> LENGTH: 402
<212> TYPE: PRT
<213> ORGANISM: artificial
<220> FEATURE:
<223> OTHER INFORMATION: bos taurus GalT Y289V

<400> SEQUENCE: 22

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Pro Leu Gln Gly Ser Ser
50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
            115                 120                 125

Arg Ser Leu Thr Ala Cys Pro Glu Glu Ser Pro Leu Leu Val Gly Pro
130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
```

```
225                 230                 235                 240
Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285

Val Phe Gly Gly Val Ser Ala Leu Ser Lys Gln Gln Phe Leu Ser Ile
    290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
        355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser

<210> SEQ ID NO 23
<211> LENGTH: 402
<212> TYPE: PRT
<213> ORGANISM: artificial
<220> FEATURE:
<223> OTHER INFORMATION: bos taurus GalT Y289A

<400> SEQUENCE: 23

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Arg
        35                  40                  45

Arg Leu Pro Gln Leu Val Gly Val His Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser
                85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Ile Leu Phe Arg Asn Arg Gln
            180                 185                 190
```

Glu His Leu Lys Tyr Trp Leu Tyr Tyr Leu His Pro Met Val Gln Arg
    195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
                260                 265                 270

Ile Ser Val Ala Met Asp Lys Phe Gly Phe Ser Leu Pro Tyr Val Gln
                275                 280                 285

Ala Phe Gly Gly Val Ser Ala Leu Ser Lys Gln Gln Phe Leu Ser Ile
                290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
                340                 345                 350

Asn Glu Pro Asn Pro Gln Arg Phe Asp Arg Ile Ala His Thr Lys Glu
                355                 360                 365

Thr Met Leu Ser Asp Gly Leu Asn Ser Leu Thr Tyr Met Val Leu Glu
                370                 375                 380

Val Gln Arg Tyr Pro Leu Tyr Thr Lys Ile Thr Val Asp Ile Gly Thr
385                 390                 395                 400

Pro Ser

<210> SEQ ID NO 24
<211> LENGTH: 402
<212> TYPE: PRT
<213> ORGANISM: artificial
<220> FEATURE:
<223> OTHER INFORMATION: bos taurus GalT Y289G

<400> SEQUENCE: 24

Met Lys Phe Arg Glu Pro Leu Leu Gly Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Arg
                35                  40                  45

Arg Leu Pro Gln Leu Val Gly Val His Pro Pro Leu Gln Gly Ser Ser
    50                  55                  60

His Gly Ala Ala Ala Ile Gly Gln Pro Ser Gly Glu Leu Arg Leu Arg
65                  70                  75                  80

Gly Val Ala Pro Pro Pro Leu Gln Asn Ser Ser Lys Pro Arg Ser Arg
                85                  90                  95

Arg Ala Pro Ser Asn Leu Asp Ala Tyr Ser His Pro Gly Pro Gly Pro
                100                 105                 110

Gly Pro Gly Ser Asn Leu Thr Ser Ala Pro Val Pro Ser Thr Thr Thr
                115                 120                 125

Arg Ser Leu Thr Ala Cys Pro Glu Glu Ser Pro Leu Leu Val Gly Pro
                130                 135                 140

```
Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
            165                 170                 175

Ile Ser Pro His Lys Val Ala Ile Ile Ile Leu Phe Arg Asn Arg Gln
                180                 185                 190

Glu His Leu Lys Tyr Trp Leu Tyr Tyr Leu His Pro Met Val Gln Arg
            195                 200                 205

Gln Gln Leu Asp Tyr Gly Ile Tyr Val Ile Asn Gln Ala Gly Glu Ser
        210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
                260                 265                 270

Ile Ser Val Ala Met Asp Lys Phe Gly Phe Ser Leu Pro Tyr Val Gln
        275                 280                 285

Gly Phe Gly Gly Val Ser Ala Leu Ser Lys Gln Gln Phe Leu Ser Ile
290                 295                 300

Asn Gly Phe Pro Asn Asn Tyr Trp Gly Trp Gly Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
            340                 345                 350

Asn Glu Pro Asn Pro Gln Arg Phe Asp Arg Ile Ala His Thr Lys Glu
            355                 360                 365

Thr Met Leu Ser Asp Gly Leu Asn Ser Leu Thr Tyr Met Val Leu Glu
        370                 375                 380

Val Gln Arg Tyr Pro Leu Tyr Thr Lys Ile Thr Val Asp Ile Gly Thr
385                 390                 395                 400

Pro Ser
```